(12) United States Patent
Cawood et al.

(10) Patent No.: US 12,410,443 B2
(45) Date of Patent: Sep. 9, 2025

(54) INDUCIBLE AAV SYSTEM COMPRISING CUMATE OPERATOR SEQUENCES

(71) Applicant: Oxford Genetics Limited, Oxford (GB)

(72) Inventors: Ryan Cawood, Oxford (GB); Tom Payne, Oxford (GB); Alissa Bray, Oxford (GB)

(73) Assignee: Oxford Genetics, Oxfordshire (GB)

( * ) Notice: Subject to any disclaimer, the term of this patent is extended or adjusted under 35 U.S.C. 154(b) by 802 days.

(21) Appl. No.: 17/427,551

(22) PCT Filed: Feb. 5, 2020

(86) PCT No.: PCT/GB2020/050252
§ 371 (c)(1),
(2) Date: Jul. 30, 2021

(87) PCT Pub. No.: WO2020/161484
PCT Pub. Date: Aug. 13, 2020

(65) Prior Publication Data
US 2022/0162636 A1    May 26, 2022

(30) Foreign Application Priority Data
Feb. 5, 2019  (GB) .................................. 1901571

(51) Int. Cl.
*C12N 15/86* (2006.01)

(52) U.S. Cl.
CPC .... *C12N 15/86* (2013.01); *C12N 2750/14143* (2013.01); *C12N 2750/14152* (2013.01); *C12N 2830/002* (2013.01); *C12N 2840/203* (2013.01)

(58) Field of Classification Search
CPC .......... C12N 15/86; C12N 2750/14143; C12N 2750/14152; C12N 2830/002
See application file for complete search history.

(56) References Cited

U.S. PATENT DOCUMENTS

| | | | |
|---|---|---|---|
| 5,622,856 | A | 4/1997 | Natsoulis |
| 7,115,391 | B1 | 10/2006 | Chen et al. |
| 10,533,188 | B2 | 1/2020 | Hermens et al. |
| 10,647,999 | B2 | 5/2020 | Cawood et al. |
| 10,858,631 | B2 | 12/2020 | Vink |
| 2002/0098572 | A1 | 7/2002 | Einerhand et al. |
| 2002/0102714 | A1 | 8/2002 | Wilson et al. |
| 2003/0040101 | A1 | 2/2003 | Wilson et al. |
| 2003/0225260 | A1 | 12/2003 | Snyder |
| 2004/0014031 | A1 | 1/2004 | Salvetti et al. |
| 2005/0112765 | A1 | 5/2005 | Li et al. |
| 2007/0202587 | A1 | 8/2007 | Hwang et al. |
| 2008/0044855 | A1 | 2/2008 | Xu et al. |
| 2014/0349374 | A1 * | 11/2014 | Galibert .................. C12N 15/86 435/235.1 |
| 2018/0127470 | A1 | 5/2018 | Cawood |
| 2018/0155740 | A1 | 6/2018 | Wu et al. |
| 2018/0327722 | A1 | 11/2018 | Vink |
| 2020/0072820 | A1 | 3/2020 | Cawood et al. |
| 2020/0157567 | A1 | 5/2020 | Cawood et al. |
| 2020/0239909 | A1 | 7/2020 | Cawood et al. |
| 2020/0277629 | A1 | 9/2020 | Cawood et al. |
| 2021/0163987 | A1 | 6/2021 | Cawood et al. |
| 2022/0154174 | A1 | 5/2022 | Lopez-Anton et al. |
| 2022/0162636 | A1 | 5/2022 | Cawood et al. |
| 2023/0076955 | A1 | 3/2023 | Cawood et al. |
| 2023/0183750 | A1 | 6/2023 | Cawood et al. |
| 2023/0183751 | A1 | 6/2023 | Cawood et al. |
| 2023/0257831 | A1 | 8/2023 | Cawood et al. |
| 2023/0313228 | A1 | 10/2023 | Cawood |
| 2023/0357794 | A1 | 11/2023 | Cawood et al. |

FOREIGN PATENT DOCUMENTS

| | | | |
|---|---|---|---|
| CN | 103189507 | A | 7/2013 |
| EP | 1385946 | B1 | 12/2009 |
| EP | 1797186 | B1 | 5/2016 |
| GB | 2566572 | A | 3/2019 |
| NZ | 528942 | A | 3/2005 |
| WO | 97/20943 | A1 | 6/1997 |
| WO | 98/46728 | A1 | 10/1998 |
| WO | 99/07833 | A1 | 2/1999 |
| WO | 99/18227 | A1 | 4/1999 |
| WO | 1999/41399 | A1 | 8/1999 |
| WO | 0017377 | A2 | 3/2000 |
| WO | WO-02088346 | A2 * | 11/2002 ......... C07K 14/4705 |
| WO | 03/061582 | A2 | 7/2003 |
| WO | 2007127264 | A2 | 11/2007 |

(Continued)

OTHER PUBLICATIONS

Chejanovsky et al., Virology (1989)173: 120-128 (Year: 1989).*
Bray, A., et al., "Reconfiguration of AAV Rep-Cap Coding Sequences Significantly Increase Viral Vector Yield and Enables Inducible AAV Production in HEK293 Cells", Poster presented at European Society of Gene Cell Therapy Annual Conference, Oct. 16-19, 2018.
Chahal, P., et al., "Key Rep-Proteins Necessary for the Adeno-Associated Virus Production by Transient Transfection in HEK293 Cells in Suspension and Serum-Free Medium", Molecular Therapy, May 1, 2018, vol. 26(5), Supplement 1, p. 328, (Abstract only).
Mullick, A., et al., "The Cumate Gene-Switch: A System for Regulated Expression in Mammalian Cells ", BMC Biotechnology, Nov. 3, 2006, vol. 6(1), p. 43.
International Search Report and Written Opinion from the International Searching Authority, for International Patent Application No. PCT/GB2020/050252, dated Mar. 18, 2020, pp. 1-17.

(Continued)

*Primary Examiner* — Evelyn Y Pyla
*Assistant Examiner* — Katherine R Small
(74) *Attorney, Agent, or Firm* — McDonnell Boehnen Hulbert & Berghoff LLP

(57) ABSTRACT

The invention relates to nucleic acid molecules, vectors and plasmids comprising AAV cap genes and rep genes, wherein the cap and rep genes are both operably-associated with an inducible promoter which comprises one or more cumate operator (CuO) sequences. The invention further relates to producer and packaging cell lines which are useful in the production of Adeno-Associated Virus (AAV) particles.

19 Claims, 15 Drawing Sheets

Specification includes a Sequence Listing.

(56) References Cited

FOREIGN PATENT DOCUMENTS

| WO | 2008063802 A2 | 5/2008 |
|---|---|---|
| WO | 2011123088 A1 | 10/2011 |
| WO | 2007148971 A2 | 9/2015 |
| WO | 2015137802 A1 | 9/2015 |
| WO | 2016/189326 A1 | 12/2016 |
| WO | 2017/049759 A1 | 3/2017 |
| WO | 2017/149292 A1 | 9/2017 |
| WO | 2018/167481 A1 | 9/2018 |
| WO | 2018/189535 A1 | 10/2018 |
| WO | 2019/020992 A1 | 1/2019 |
| WO | 2019/058108 A1 | 3/2019 |
| WO | 2019/141993 A1 | 7/2019 |
| WO | 2020/161484 A1 | 8/2020 |
| WO | 2020/183133 A1 | 9/2020 |
| WO | 2021/156609 A1 | 8/2021 |
| WO | 2021/156611 A1 | 8/2021 |
| WO | 2021/234388 A1 | 11/2021 |
| WO | 2021/234389 A1 | 11/2021 |
| WO | 2022/038367 A1 | 2/2022 |
| WO | 2022/038368 A1 | 2/2022 |
| WO | 2022/038369 A1 | 2/2022 |
| WO | 2022/129905 A1 | 6/2022 |
| WO | 2022/223954 A1 | 10/2022 |

OTHER PUBLICATIONS

UK Search Report from the UK Intellectual Property Office, for GB1901571.8, dated Oct. 3, 2019, pp. 1-4.
"Introduction to Adeno-Associated Virus (AAV)", Vector Biolabs, article downloaded on Jan. 3, 2023 from https://www.vectorbiolabs.com/intro-to-aav/, 9 pages.
Office Action dated Nov. 29, 2022 for Indian Patent Application No. 202047021768.
Alissa Bray et al., "Reconfiguration of AAV Rep-Cap Coding Sequences Significantly Increases Viral Vector Yield and Enables Inducible AAV Production in HEK293 Cells," European Society of Gene and Cell Therapy Annual Congress, Oct. 16-19, 2018.
Long-Sheng Chang et al., "The Adenovirus DNA-Binding Protein Stimulates the Rate of Transcription Directed by Adenovirus and Adeno-Associated Virus Promoters," J. Virology, vol. 64(5), pp. 2103-2109.
Green, M.R. and Sambrook, J., "Molecular Cloning: A Laboratory Manual", Fourth Edition, 2012, vol. 1, pp. 1-34.
Clonetech—Helper Free System, 2016, pp. 1-22. [Retrieved from the Internet on Jun. 8, 2020: <URL: www.clonetech.com/GB/Products/Viral_Transduction/AAV_Vector_Systems/Helper_Free_Expression_System?sitex=10030:22372:US>].
Altschul, et al., "Gapped BLAST and PSI-BLAST: A New Generation of Protein Database Search Programs", Nucleic Acids Res., 1997, vol. 25(17), pp. 3389-3402.
Boussif, O., et al., "A Versatile Vector for Gene and Oligonucleotide Transfer Into Cells in Culture and in Vivo: Polyethylenimine", Proc. Natl. Acad. Sci. USA, Aug. 1, 1995, vol. 92(16), pp. 7297-7301.
Ma, B., et al., "PatternHunter: Faster and More Sensitive Homology Search", Bioinformatics, Mar. 2002, vol. 18(3), pp. 440-445.
Ogasawara, Y., et al., "Efficient Production of Adeno-associated Virus Vectors Using Split-type Helper Plasmids", Japanese Journal of Cancer Research, Apr. 1999, vol. 90(4), pp. 476-483.
Sitaraman, V., et al., "Computationally Designed Adeno-Associated Virus (AAV) Rep 78 is Efficiently Maintained Within an Adenovirus Vector", Proc. Natl. Acad. Sci. USA, Aug. 23, 2011, vol. 108(34), pp. 14294-14299.
Whiteway, A., et al., "Construction of Adeno-associated Virus Packaging Plasmids and Cells that Directly Select for AAV Helper Functions", Journal of Virological Methods, 2003, vol. 114(1), pp. 1-10.
Basic Local Alignment Search Tool. [Retrieved from the internet Mar. 4, 2017:<URL:http://www.ncbi.nlm.nih.gov/BLAST>].
"Searching the Trace Archive with Discontiguous MegaBlast". [Retrieved from the internet Mar. 4, 2019:<URL:www.ncbi.nlm.nih.gov/Web/Newsltr/FallWinter02/blastlab.html>].
International Search Report and Written Opinion, for International Application No. PCT/GB2019/050134, dated Mar. 21, 2009, pp. 1-15.
Search Report from the UK Intellectual Property Office, for Application No. GB1800903.5, dated Oct. 15, 2018, pp. 1-4.
Notification of the First OA dated Dec. 28, 2022 issued in Chinese Patent Application No. 201980006731.8 and English Translation of Notification.
Gaillet, B., et al., "High-Level Recombinant Protein Production in CHO Cells Using Lentiviral Vectors and the Cumate Gene-Switch", Biotechnology and Bioengineering, Feb. 2010, vol. 106(2), pp. 203-215.
Altschul, S.F., et al., "Gapped BLAST and PSI-BLAST: A New Generation of Protein Database Search Programs", Nucleic Acids Research, 1997, vol. 25(17), pp. 3389-3402.
Boussif, O., et al., "A Versatile Vector for Gene and Oligonucleotide Transfer into Cells in Culture and in vivo: Polyethylenimine", Proc. Natl. Acad. Sci., Aug. 1995, vol. 92, pp. 7297-7301.
Green, M.R. and Sambrook, J., "Molecular Cloning: A Laboratory Manual", 4th Edition, Cold Spring Harbor Laboratory Press, 2012, vol. 1, pp. 1-34.
Hörner, M. and Weber, W., "Molecular Switches in Animal Cells", FEBS Letters, 2012, vol. 586, pp. 2084-2096.
Ma, B., et al., "PatternHunter: Faster and More Sensitive Homology Search", Bioinformatics, 2002, vol. 18(3), pp. 440-445.
BLAST Lab, "Searching the Trace Archive with Discontiguous MegaBlast", [Retrieved from the internet Sep. 8, 2021: <URL:https://www.ncbi.nlm.nih.gov/Web/Newsltr/FallWinter02/blastlab.html>].
"BLAST: Basic Local Alignment Search Tool", Feb. 3, 2020. [Retrieved from the internet Sep. 8, 2021:<URL:https://blast.ncbi.nlm.nih.gov/Blast.cgi>].

* cited by examiner

Figures 3A and 3B

SEQUENCE LISTING

<160> NUMBER OF SEQ ID NOS: 24

<210> SEQ ID NO 1
<211> LENGTH: 1866
<212> TYPE: DNA
<213> ORGANISM: adeno-associated virus 2

<400> SEQUENCE: 1
atgccggggt tttacgagat tgtgattaag gtccccagcg accttgacga gcatctgccc        60
ggcatttctg acagctttgt gaactgggtg gccgagaagg aatgggagtt gccgccagat       120
tctgacatgg atctgaatct gattgagcag gcacccctga ccgtggccga gaagctgcag       180
cgcgactttc tgacggaatg cgcgcgtgtg agtaaggccc cggaggccct tttctttgtg       240
caatttgaga agggagagag ctacttccac atgcacgtgc tcgtggaaac caccggggtg       300
aaatccatgg ttttgggacg tttcctgagt cagattcgcg aaaaactgat tcagagaatt       360
taccgcggga tcgagccgac tttgccaaac tggttcgcgg tcacaaagac cagaaatggc       420 gccgaggcg ggaacaaggt ggtggatgag tgctacatcc ccaattactt gctccccaaa        480
acccagcctg agctccagtg ggcgtggact aatatggaac agtatttaag cgcctgtttg       540
aatctcacgg agcgtaaacg gttggtggcg cagcatctga cgcacgtgtc gcagacgcag       600
gagcagaaca aagagaatca gaatcccaat tctgatgcgc cggtgatcag atcaaaaact       660
tcagccaggt acatggagct ggtcgggtgg ctcgtggaca aggggattac ctcggagaag       720
cagtggatcc aggaggacca ggcctcatac atctccttca tgcgcctc caactcgcgg       780 tcccaaatca aggctgcctt ggacaatgcg ggaaagatta tgagcctgac taaaaccgcc       840
cccgactacc tggtgggcca gcagcccgtg gaggacattt ccagcaatcg gatttataaa       900
attttggaac taaacgggta cgatccccaa tatgcggctt ccgtctttct gggatgggcc       960
acgaaaaagt tcggcaagag gaacaccatc tggctgtttg gcctgcaac taccggggaag       1020 accaacatcg cggaggccat gcccacact gtgcccttct acgggtgcgt aaactggacc       1080
aatgagaact ttcccttcaa cgactgtgtc gacaagatgg tgatctggtg ggaggagggg       1140
aagatgaccg ccaaggtcgt ggagtcggcc aaagccattc tcggaggaag caaggtgcgc       1200

```
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caatag                                                               1866
```

<210> SEQ ID NO 2
<211> LENGTH: 621
<212> TYPE: PRT
<213> ORGANISM: adeno-associated virus 2

<400> SEQUENCE: 2

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
```

```
            245                 250                 255
Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
            485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
            565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
            610                 615                 620

<210> SEQ ID NO 3
<211> LENGTH: 528
<212> TYPE: PRT
<213> ORGANISM: adeno-associated virus 2

<400> SEQUENCE: 3
```

```
Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
```

```
                    420             425             430
Thr Thr Phe Glu His Gln Gln Pro Leu Gln Asp Arg Met Phe Lys Phe
            435             440             445

Glu Leu Thr Arg Arg Leu Asp His Asp Phe Gly Lys Val Thr Lys Gln
        450             455             460

Glu Val Lys Asp Phe Phe Arg Trp Ala Lys Asp His Val Val Glu Val
465             470             475             480

Glu His Glu Phe Tyr Val Lys Lys Gly Gly Ala Lys Lys Arg Pro Ala
            485             490             495

Pro Ser Asp Ala Asp Ile Ser Glu Pro Lys Arg Val Arg Glu Ser Val
        500             505             510

Ala Gln Pro Ser Thr Ser Asp Ala Glu Ala Ser Ile Asn Tyr Ala Asp
        515             520             525

<210> SEQ ID NO 4
<211> LENGTH: 397
<212> TYPE: PRT
<213> ORGANISM: adeno-associated virus 2

<400> SEQUENCE: 4

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270
```

```
Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
370                 375                 380

Leu Val Asn Val Asp Leu Asp Asp Cys Ile Phe Glu Gln
385                 390                 395

<210> SEQ ID NO 5
<211> LENGTH: 312
<212> TYPE: PRT
<213> ORGANISM: adeno-associated virus 2

<400> SEQUENCE: 5

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255
```

Glu His Glu Phe Tyr Val Lys Lys Gly Gly Ala Lys Lys Arg Pro Ala
        260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
        290                 295                 300

Arg Leu Ala Arg Gly His Ser Leu
305                 310

<210> SEQ ID NO 6
<211> LENGTH: 1866
<212> TYPE: DNA
<213> ORGANISM: adeno-associated virus 2

<400> SEQUENCE: 6

| | |
|---|---|
| atgccggggt tttacgagat tgtgattaag gtccccagcg accttgacgg gcatctgccc | 60 |
| ggcatttctg acagctttgt gaactgggtg gccgagaagg aatgggagtt gccgccagat | 120 |
| tctgacatgg atctgaatct gattgagcag gcaccctga ccgtggccga aagctgcag | 180 |
| cgcgactttc tgacggaatg cgccgtgtg agtaaggccc cggaggccct tttctttgtg | 240 |
| caatttgaga agggagagag ctacttccac atgcacgtgc tcgtggaaac caccggggtg | 300 |
| aaatccatgg ttttgggacg tttcctgagt cagattcgcg aaaaactgat tcagagaatt | 360 |
| taccgcggga tcgagccgac tttgccaaac tggttcgcgg tcacaaagac cagaaatggc | 420 |
| gccggaggcg ggaacaaggt ggtggatgag tgctacatcc ccaattactt gctccccaaa | 480 |
| acccagcctg agctccagtg gcgtggact aatatggaac agtacctcag cgcctgtttg | 540 |
| aatctcacgg agcgtaaacg gttggtggcg cagcatctga cgcacgtgtc gcagacgcag | 600 |
| gagcagaaca aagagaatca gaatcccaat tctgatgcgc cggtgatcag atcaaaaact | 660 |
| tcagccaggt acatggagct ggtcgggtgg ctcgtggaca agggattac ctcggagaag | 720 |
| cagtggatcc aggaggacca ggcctcatac atctccttca tgcggcctc caactcgcgg | 780 |
| tcccaaatca aggctgcctt ggacaatgcg ggaaagatta tgagcctgac taaaaccgcc | 840 |
| cccgactacc tggtgggcca gcagcccgtg gaggacattt ccagcaatcg gatttataaa | 900 |
| attttggaac taaacgggta cgatccccaa tatgcggctt ccgtctttct gggatgggcc | 960 |
| acgaaaaagt tcggcaagag gaacaccatc tggctgtttg gcctgcaac taccgggaag | 1020 |
| accaacatcg cggaggccat agcccacact gtgcccttct acgggtgcgt aaactggacc | 1080 |
| aatgagaact ttcccttcaa cgactgtgtc gacaagatgg tgatctggtg ggaggagggg | 1140 |
| aagatgaccg ccaaggtcgt ggagtcggcc aaagccattc tcggaggaag caaggtgcgc | 1200 |
| gtggaccaga atgcaagtc ctcggcccag atagacccga ctcccgtgat cgtcacctcc | 1260 |
| aacaccaaca tgtgcgccgt gattgacggg aactcaacga ccttcgaaca ccagcagccg | 1320 |
| ttgcaagacc ggatgttcaa atttgaactc acccgccgtc tggatcatga ctttgggaag | 1380 |
| gtcaccaagc aggaagtcaa agacttttt cggtgggcaa aggatcacgt ggttgaggtg | 1440 |
| gagcatgaat tctacgtcaa aaagggtgga gccaagaaaa gacccgcccc cagtgacgca | 1500 |
| gatataagtg agcccaaacg ggtgcgcgag tcagttgcgc agccatcgac gtcagacgcg | 1560 |
| gaagcttcga tcaactacgc agacaggtac caaaacaaat gttctcgtca cgtgggcatg | 1620 |
| aatctgatgt gtttccctg cagacaatgc gagagaatga atcagaattc aaatatctgc | 1680 |
| ttcactcacg gacagaaaga ctgtttagag tgctttcccg tgtcagaatc tcaacccgtt | 1740 |

```
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caatag                                                               1866

<210> SEQ ID NO 7
<211> LENGTH: 1589
<212> TYPE: DNA
<213> ORGANISM: adeno-associated virus 2

<400> SEQUENCE: 7
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcacccctga ccgtggccga gaagctgcag     180
cgcgactttc tgacggaatg cgccgtgtg agtaaggccc cggaggccct tttctttgtg      240
caatttgaga agggagagag ctacttccac atgcacgtgc tcgtggaaac caccggggtg     300
aaatccatgg ttttgggacg tttcctgagt cagattcgcg aaaaactgat tcagagaatt     360
taccgcggga tcgagccgac tttgccaaac tggttcgcgg tcacaaagac cagaaatggc     420 gccgaggcg ggaacaaggt ggtggatgag tgctacatcc ccaattactt gctccccaaa      480
acccagcctg agctccagtg ggcgtggact aatatggaac agtacctcag cgcctgtttg     540
aatctcacgg agcgtaaacg gttggtggcg cagcatctga cgcacgtgtc gcagacgcag     600
gagcagaaca agagaatca gaatcccaat tctgatgcgc cggtgatcag atcaaaaact     660
tcagccaggt acatggagct ggtcgggtgg ctcgtggaca gggggattac ctcggagaag     720
cagtggatcc aggaggacca ggcctcatac atctccttca atgcggcctc caactcgcgg     780
tcccaaatca aggctgcctt ggacaatgcg ggaaagatta tgagcctgac taaaaccgcc     840
cccgactacc tggtgggcca gcagcccgtg gaggacattt ccagcaatcg gatttataaa     900
attttggaac taaacgggta cgatcccaa tatgcggctt ccgtctttct gggatgggcc     960
acgaaaaagt tcggcaagag gaacaccatc tggctgtttg gcctgcaac taccgggaag    1020 accaacatcg cggaggccat agcccacact gtgcccttct acgggtgcgt aaactggacc    1080
aatgagaact ttccccttcaa cgactgtgtc gacaagatgg tgatctggtg ggaggagggg    1140
aagatgaccg ccaaggtcgt ggagtcggcc aaagccattc tcggaggaag caaggtcgcg    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacagtag                                     1589

<210> SEQ ID NO 8
<211> LENGTH: 1195
<212> TYPE: DNA
<213> ORGANISM: adeno-associated virus 2

<400> SEQUENCE: 8
catggagctg gtcgggtggc tcgtggacaa ggggattacc tcggagaagc agtggatcca      60
ggaggaccag gcctcataca tctccttcaa tgcggcctcc aactcgcggt cccaaatcaa     120
```

```
ggctgccttg gacaatgcgg gaaagattat gagcctgact aaaaccgccc ccgactacct    180
ggtgggccag cagcccgtgg aggacatttc cagcaatcgg atttataaaa ttttggaact    240
aaacgggtac gatccccaat atgcggcttc cgtctttctg ggatgggcca cgaaaaagtt    300
cggcaagagg aacaccatct ggctgtttgg gcctgcaact accgggaaga ccaacatcgc    360
ggaggccata gcccacactg tgccttcta  cgggtgcgta aactggacca atgagaactt    420
tcccttcaac gactgtgtcg acaagatggt gatctggtgg gaggagggga agatgaccgc    480
caaggtcgtg gagtcggcca agccattct  cggaggaagc aaggtgcgcg tggaccagaa    540
atgcaagtcc tcggcccaga tagacccgac tcccgtgatc gtcacctcca acaccaacat    600
gtgcgccgtg attgacggga actcaacgac cttcgaacac cagcagccgt gcaagaccg    660 gatgttcaaa tttgaactca cccgccgtct ggatcatgac tttgggaagg tcaccaagca    720
ggaagtcaaa gactttttcc ggtgggcaaa ggatcacgtg gttgaggtgg agcatgaatt    780
ctacgtcaaa aagggtggag ccaagaaaag acccgccccc agtgacgcag atataagtga    840
gcccaaacgg gtgcgcgagt cagttgcgca ccatcgacg  tcagacgcgg aagcttcgat    900
caactacgca gacaggtacc aaaacaaatg ttctcgtcac gtgggcatga atctgatgct    960
gtttccctgc agacaatgcg agagaatgaa tcagaattca aatatctgct tcactcacgg   1020
acagaaagac tgtttagagt gctttcccgt gtcagaatct caaccccgttt ctgtcgtcaa   1080 aaaggcgtat cagaaactgt gctacattca tcatatcatg ggaaaggtgc cagacgcttg   1140
cactgcctgc gatctggtca atgtggattt ggatgactgc atctttgaac aatag         1195
```

<210> SEQ ID NO 9  
<211> LENGTH: 939  
<212> TYPE: DNA  
<213> ORGANISM: adeno-associated virus 2

<400> SEQUENCE: 9

```
atggagctgg tcgggtggct cgtggacaag gggattacct cggagaagca gtggatccag     60
gaggaccagg cctcatacat ctccttcaat gcggcctcca actcgcggtc ccaaatcaag    120
gctgccttgg acaatgcggg aaagattatg agcctgacta aaaccgcccc cgactacctg    180
gtgggccagc agcccgtgga ggacatttcc agcaatcgga tttataaaat tttggaacta    240
aacgggtacg atccccaata tgcggcttcc gtctttctgg gatgggccac gaaaaagttc    300
ggcaagagga acaccatctg gctgtttggg cctgcaacta ccgggaagac caacatcgcg    360
gaggccatag cccacactgt gcccttctac gggtgcgtaa actggaccaa tgagaacttt    420
cccttcaacg actgtgtcga caagatggtg atctggtggg aggaggggaa gatgaccgcc    480
aaggtcgtga gtcggccaa  agccattctc ggaggaagca aggtgcgcgt ggaccagaaa    540
tgcaagtcct cggcccagat agacccgact cccgtgatcg tcacctccaa caccaacatg    600
tgcgccgtga ttgacgggaa ctcaacgacc ttcgaacacc agcagccgtt gcaagaccgg    660
atgttcaaat ttgaactcac ccgccgtctg gatcatgact ttgggaaggt caccaagcag    720
gaagtcaaag acttttttccg gtgggcaaag gatcacgtgg ttgaggtgga gcatgaattc    780
tacgtcaaaa agggtggagc caagaaaaga cccgccccca gtgacgcaga tataagtgag    840
cccaaacggg tgcgcgagtc agttgcgcag ccatcgacgt cagacgcgga agcttcgatc    900
aactacgcag acagattggc tcgaggacac tctctctag                             939
```

<210> SEQ ID NO 10

```
<211> LENGTH: 2559
<212> TYPE: DNA
<213> ORGANISM: adeno-associated virus 2

<400> SEQUENCE: 10
cagttgcgca gccatcgacg tcagacgcgg aagcttcgat caactacgca gacaggtacc      60
aaaacaaatg ttctcgtcac gtgggcatga atctgatgct gtttccctgc agacaatgcg     120
agagaatgaa tcagaattca aatatctgct tcactcacgg acagaaagac tgtttagagt     180
gctttcccgt gtcagaatct caacccgttt ctgtcgtcaa aaaggcgtat cagaaactgt     240
gctacattca tcatatcatg ggaaaggtgc cagacgcttg cactgcctgc gatctggtca     300
atgtggattt ggatgactgc atctttgaac aataaatgat ttaaatcagg tatggctgcc     360
gatggttatc ttccagattg gctcgaggac actctctctg aaggaataag acagtggtgg     420
aagctcaaac ctggcccacc accaccaaag cccgcagagc ggcataagga cgacagcagg     480
ggtcttgtgc ttcctgggta caagtacctc ggacccttca cggactcga caagggagag     540 ccggtcaaca ggcagacgc cgcggccctc gagcacgaca agcctacga ccggcagctc      600 gacagcggag acaacccgta cctcaagtac aaccacgccg acgcggagtt tcaggagcgc     660 cttaagaag atacgtcttt tgggggcaac ctcggacgag cagtcttcca ggcgaaaaag     720
agggttcttg aacctctggg cctggttgag gaacctgtta agacggctcc gggaaaaaag     780
aggccggtag agcactctcc tgtggagcca gactcctcct cgggaaccgg aaaggcgggc     840
cagcagcctg caagaaaaag attgaatttt ggtcagactg agacgcaga ctcagtacct     900 gacccccagc ctctcggaca gccaccagca gcccctctg gtctgggaac taatacgatg     960
gctacaggca gtggcgcacc aatggcagac aataacgagg gcgccgacgg agtgggtaat    1020 tcctcggaa attggcattg cgattccaca tggatgggcg acagagtcat caccaccagc    1080
acccgaacct gggccctgcc cacctacaac aaccacctct acaaacaaat tccagccaa     1140 tcaggagcct cgaacgacaa tcactacttt ggctacagca ccccttgggg gtattttgac    1200
ttcaacagat tccactgcca cttttcacca cgtgactggc aaagactcat caacaacaac    1260
tggggattcc gacccaagag actcaacttc aagctcttta acattcaagt caaagaggtc    1320
acgcagaatg acggtacgac gacgattgcc aataacctta ccagcacggt tcaggtgttt    1380
actgactcgg agtaccagct cccgtacgtc ctcggctcgg cgcatcaagg atgcctcccg    1440
ccgttcccag cagacgtctt catggtgcca cagtatggat acctcaccct gaacaacggg    1500
agtcaggcag taggacgctc ttcatttac tgcctggagt actttccttc tcagatgctg    1560
cgtaccggaa acaactttac cttcagctac acttttgagg acgttccttt ccacagcagc    1620
tacgctcaca gccagagtct ggaccgtctc atgaatcctc tcatcgacca gtacctgtat    1680
tacttgagca gaacaaacac tccaagtgga accaccacgc agtcaaggct tcagttttct    1740
caggccggag cgagtgacat tcgggaccag tctaggaact ggcttcctgg accctgttac    1800
cgccagcagc gagtatcaaa gacatctgcg gataacaaca cagtgaata ctcgtggact     1860 ggagctacca agtaccacct caatggcaga gactctctgg tgaatccggg cccggccatg    1920
gcaagccaca ggacgatga agaaaagttt tttcctcaga gcggggttct catctttggg    1980
aagcaaggct cagagaaaac aaatgtggac attgaaaagg tcatgattac agacgaagag    2040
gaaatcagga caaccaatcc cgtggctacg gagcagtatg gttctgtatc taccaacctc    2100
cagagaggca acagacaagc agctaccgca gatgtcaaca cacaaggcgt tcttccaggc    2160
atggtctggc aggacagaga tgtgtacctt caggggccca tctgggcaaa gattccacac    2220
```

-continued

```
acggacggac attttcaccc ctctcccctc atgggtggat tcggacttaa acaccctcct    2280
ccacagattc tcatcaagaa cacccggta cctgcgaatc cttcgaccac cttcagtgcg    2340
gcaaagtttg cttccttcat cacacagtac tccacgggac aggtcagcgt ggagatcgag    2400
tgggagctgc agaaggaaaa cagcaaacgc tggaatcccg aaattcagta cacttccaac    2460
tacaacaagt ctgttaatgt ggactttact gtggacacta atggcgtgta ttcagagcct    2520
cgccccattg gcaccagata cctgactcgt aatctgtaa                          2559
```

<210> SEQ ID NO 11
<211> LENGTH: 735
<212> TYPE: PRT
<213> ORGANISM: adeno-associated virus 2

<400> SEQUENCE: 11

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
```

```
            305                 310                 315                 320
Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 12
<211> LENGTH: 26
<212> TYPE: DNA
<213> ORGANISM: Pseudomonas putida

<400> SEQUENCE: 12
agaaacaaac caacctgtct gtatta                                           26

<210> SEQ ID NO 13
<211> LENGTH: 176
<212> TYPE: DNA
<213> ORGANISM: Artificial Sequence
<220> FEATURE:
<223> OTHER INFORMATION: 6 CuO sites from Pseudomonas putida

<400> SEQUENCE: 13
agaaacaaac caacctgtct gtattatcaa agaaacaaac caacctgtct gtattatcaa      60
agaaacaaac caacctgtct gtattatcaa agaaacaaac caacctgtct gtattatcaa     120
agaaacaaac caacctgtct gtattatcaa agaaacaaac caacctgtct gtatta         176

<210> SEQ ID NO 14
<211> LENGTH: 519
<212> TYPE: DNA
<213> ORGANISM: Encephalomyocarditis virus

<400> SEQUENCE: 14
cgttactggc cgaagccgct tggaataagg ccggtgtgcg tttgtctata tgttattttc 60
caccatattg ccgtcttttg gcaatgtgag ggcccggaaa cctggccctg tcttcttgac 120
gagcattcct aggggtcttt cccctctcgc caaaggaatg caaggtctgt tgaatgtcgt 180
gaaggaagca gttcctctgg aagcttcttg aagacaaaca acgtctgtag cgaccctttg 240
caggcagcgg aaccccccac ctggcgacag gtgcctctgc ggccaaaagc cacgtgtata 300
agatacacct gcaaaggcgg cacaacccca gtgccacgtt gtgagttgga tagttgtgga 360
aagagtcaaa tggctcccct caagcgtatt caacaagggg ctgaaggatg cccagaaggt 420
accccattgt atgggatctg atctggggcc tcggtgcaca tgctttacat gtgtttagtc 480
gaggttaaaa aacgtctagg ccccccgaac cacggggac 519

<210> SEQ ID NO 15
<211> LENGTH: 461
<212> TYPE: DNA
<213> ORGANISM: Foot-and-mouth disease virus

<400> SEQUENCE: 15
agcaggtttc cccaactgac acaaaacgtg caacttgaaa ctccgcctgg tctttccagg 60
tctagagggg taacactttg tactgcgttt ggctccacgc tcgatccact ggcgagtgtt 120
agtaacagca ctgttgcttc gtagcggagc atgacggccg tgggaactcc tccttggtaa 180
caaggaccca cggggccaaa agccacgccc acacgggccc gtcatgtgtg caaccccagc 240
acggcgactt tactgcgaaa cccactttaa agtgacattg aaactggtac ccacacactg 300
gtgacaggct aaggatgccc ttcaggtacc ccgaggtaac acgcgacact cgggatctga 360
gaaggggact ggggcttcta taaaagcgct cggtttaaaa agcttctatg cctgaatagg 420
tgaccggagg tcggcacctt tcctttgcaa ttactgacca c 461

<210> SEQ ID NO 16

<211> LENGTH: 5341
<212> TYPE: DNA
<213> ORGANISM: adeno-associated virus 5

<400> SEQUENCE: 16

```
ggtacccaac tccatgctca acagtcccca ggtacagccc accctgcgtc gcaaccagga      60
acagctctac agcttcctgg agcgccactc gccctacttc cgcagccaca gtgcgcagat     120
taggagcgcc acttcttttt gtcacttgaa aaacatgtaa aaataatgta ctagagacac     180
tttcaataaa ggcaaatgct tttatttgta cactctcggg tgattattta cccccaccct     240
tgccgtctgc gccgtttaaa aatcaaaggg gttctgccgc gcatcgctat gcgccactgg     300
cagggacacg ttgcgatact ggtgtttagt gctccactta aactcaggca caaccatccg     360
cggcagctcg gtgaagtttt cactccacag gctgcgcacc atcaccaacg cgtttagcag     420
gtcgggcgcc gatatcttga agtcgcagtt ggggcctccg ccctgcgcgc gcgagttgcg     480
atacacaggg ttgcagcact ggaacactat cagcgccggg tggtgcacgc tggccagcac     540
gctcttgtcg gagatcagat ccgcgtccag gtcctccgcg ttgctcaggg cgaacggagt     600
caactttggt agctgccttc ccaaaaaggg cgcgtgccca ggctttgagt tgcactcgca     660
ccgtagtggc atcaaaaggt gaccgtgccc ggtctgggcg ttaggataca cgcgcctgca     720
aaaagccttg atctgcttaa aagccacctg agcctttgcg ccttcagaga gaacatgcc      780
gcaagacttg ccggaaaact gattggccgg acaggccgcg tcgtgcacgc agcaccttgc     840
gtcggtgttg agatctgcac ccacatttcg gccccaccgg ttcttcacga tcttggcctt     900
gctagactgc tccttcagcg cgcgctgccc gttttcgctc gtcacatcca tttcaatcac     960
gtgctcctta tttatcataa tgcttccgtg tagacactta agctcgcctt cgatctcagc    1020
gcagcggtga gccacaacg cgcagcccgt gggctcgtga tgcttgtagg tcacctctgc     1080
aaacgactgc aggtacgcct gcaggaatcg ccccatcatc gtcacaaagg tcttgttgct    1140
ggtgaaggtc agctgcaacc cgcggtgctc ctcgttcagc caggtcttgc atacggccgc    1200
cagagcttcc acttggtcag gcagtagttt gaagttcgcc tttagatcgt tatccacgtg    1260
gtacttgtcc atcagcgcgc gcgcagcctc catgcccttc tcccacgcag acacgatcgg    1320
cacactcagc gggttcatca ccgtaatttc actttccgct tcgctgggct cttcctcttc    1380
ctcttgcgtc gcataccac gcgccactgg gtcgtcttca ttcagccgcc gcactgtgcg    1440
cttacctcct ttgccatgct tgattagcac cggtgggttg ctgaaaccca ccatttgtag    1500
cgccacatct tctctttctt cctcgctgtc cacgattacc tctggtgatg gcgggcgctc    1560
gggcttggga gaagggcgct tcttttttctt cttgggcgca atggccaaat ccgccgccga    1620
ggtcgatggc cgcgggctgg gtgtgcgcgg caccagcgcg tcttgtgatg agtcttcctc    1680
gtcctcggac tcgatacgcc gcctcatccg cttttttggg ggcgcccggg gaggcggcgg    1740
cgacggggac gggacgaca cgtcctccat ggttggggga cgtcgcgccg caccgcgtcc     1800
gcgctcgggg gtggtttcgc gctgctcctc ttcccgactg ccatttcct tctcctatag    1860
gcagaaaaag atcatggagt cagtcgagaa gaaggacagc ctaaccgccc cctctgagtt    1920
cgccaccacc gcctccaccg atgccgccaa gcgcctacc accttccccg tcgaggcacc    1980
cccgcttgag gaggaggaag tgattatcga gcaggaccca ggttttgtaa gcgaagacga    2040
cgaggaccgc tcagtaccaa cagaggataa aaagcaagac caggacaacg cagaggcaaa    2100
cgaggaacaa gtcgggcggg gggacgaaag gcatggcgac tacctagatg tgggagacga    2160
cgtgctgttg aagcatctgc agcgccagtg cgccattatc tgcgacgcgt tgcaagagcg    2220
```

```
cagcgatgtg cccctcgcca tagcggatgt cagccttgcc tacgaacgcc acctattctc    2280
accgcgcgta ccccccaaac gccaagaaaa cggcacatgc gagcccaacc cgcgcctcaa    2340
cttctacccc gtatttgccg tgccagaggt gcttgccacc tatcacatct ttttccaaaa    2400
ctgcaagata cccctatcct gccgtgccaa ccgcagccga gcggacaagc agctggcctt    2460
gcggcagggc gctgtcatac ctgatatcgc ctcgctcaac gaagtgccaa aaatctttga    2520
gggtcttgga cgcgacgaga agcgcgcggc aaacgctctg caacaggaaa acagcgaaaa    2580
tgaaagtcac tctggagtgt tggtggaact cgagggtgac aacgcgcgcc tagccgtact    2640
aaaacgcagc atcgaggtca cccactttgc ctacccggca cttaacctac cccccaaggt    2700
catgagcaca gtcatgagtg agctgatcgt gcgccgtgcg cagcccctgg agagggatgc    2760
aaatttgcaa gaacaaacag aggagggcct accgcagtt ggcgacgagc agctagcgcg    2820
ctggcttcaa acgcgcgagc ctgccgactt ggaggagcga cgcaaactaa tgatggccgc    2880
agtgctcgtt accgtggagc ttgagtgcat gcagcggttc tttgctgacc cggagatgca    2940
gcgcaagcta gaggaaacat tgcactacac cttttcgacag ggctacgtac gccaggcctg    3000
caagatctcc aacgtggagc tctgcaacct ggtctcctac cttggaattt tgcacgaaaa    3060
ccgccttggg caaaacgtgc ttcattccac gctcaagggc gaggcgcgcc gcgactacgt    3120
ccgcgactgc gtttacttat ttctatgcta cacctggcag acggccatgg gcgtttggca    3180
gcagtgcttg gaggagtgca acctcaagga gctgcagaaa ctgctaaagc aaaacttgaa    3240
ggacctatgg acggccttca cgagcgctc cgtggccgcg cacctggcgg acatcatttt    3300
ccccgaacgc ctgcttaaaa ccctgcaaca gggtctgcca gacttcacca gtcaaagcat    3360
gttgcagaac tttaggaact ttatcctaga gcgctcagga atcttgcccg ccacctgctg    3420
tgcacttcct agcgactttg tgcccattaa gtaccgcgaa tgccctccgc cgctttgggg    3480
ccactgctac cttctgcagc tagccaacta ccttgcctac cactctgaca taatggaaga    3540
cgtgagcggt gacggtctac tggagtgtca ctgtcgctgc aacctatgca ccccgcaccg    3600
ctccctggtt tgcaattcgc agctgcttaa cgaaagtcaa attatcggta cctttgagct    3660
gcagggtccc tcgcctgacg aaaagtccgc ggctccgggg ttgaaactca ctccggggct    3720
gtggacgtcg gcttaccttc gcaaatttgt acctgaggac taccacgccc acgagattag    3780
gttctacgaa gaccaatccc gcccgcctaa tgcggagctt accgcctgcg tcattacccca    3840
gggccacatt cttggccaat gcaagccat caacaaagcc cgccaagagt ttctgctacg    3900
aaagggacgg ggggtttact tggacccca gtccggcgag gagctcaacc caatcccccc    3960
gccgccgcag ccctatcagc agcagccgcg ggcccttgct tcccaggatg cacccaaaa    4020
agaagctgca gctgccgccg ccacccacgg acgaggagga atactgggac agtcaggcag    4080
aggaggtttt ggacgaggag gaggaggaca tgatggaaga ctgggagagc ctagacgagg    4140
aagcttccga ggtcgaagag gtgtcagacg aaacaccgtc accctcggtc gcattcccct    4200
cgccggcgcc ccagaaatcg gcaaccggtt ccagcatggc tacaacctcc gctcctcagg    4260
cgccgccggc actgcccgtt cgccgaccca accgtagatg ggacaccact ggaaccaggg    4320
ccggtaagtc caagcagccg ccgccgttag cccaagagca acaacagcgc caaggctacc    4380
gctcatggcg cgggcacaag aacgccatag ttgcttgctt gcaagactgt ggggcaaca    4440
tctccttcgc ccgccgcttt cttctctacc atcacgcgt ggccttcccc cgtaacatcc    4500
tgcattacta ccgtcatctc tacagcccat actgcaccgg cggcagcggc agcaacagca    4560
```

```
gcggccacac agaagcaaag gcgaccggat agcaagactc tgacaaagcc caagaaatcc    4620
acagcggcgg cagcagcagg aggaggagcg ctgcgtctgg cgcccaacga acccgtatcg    4680
acccgcgagc ttagaaacag gattttcccc actctgtatg ctatatttca acagagcagg    4740
ggccaagaac aagagctgaa ataaaaaaac aggtctctgc gatccctcac ccgcagctgc    4800
ctgtatcaca aaagcgaaga tcagcttcgg cgcacgctgg aagacgcgga ggctctcttc    4860
agtaaatact gcgcgctgac tcttaaggac tagtttcgcg ccctttctca aatttaagcg    4920
cgaaaactac gtcatctcca gcggccacac ccggcgccag cacctgttgt cagcgccatt    4980
atgagcaagg aaattcccac gccctacatg tggagttacc agccacaaat gggacttgcg    5040
gctggagctg cccaagacta ctcaacccga ataaactaca tgagcgcggg accccacatg    5100
atatcccggg tcaacggaat acgcgcccac cgaaaccgaa ttcccttgga acaggcggct    5160
attaccacca cacctcgtaa taaccttaat ccccgtagtt ggcccgctgc cctggtgtac    5220
caggaaagtc ccgctcccac cactgtggta cttcccagag acgcccaggc cgaagttcag    5280
atgactaact caggggcgca gcttgcgggc ggctttcgtc acagggtgcg gtcgcccggg    5340
c                                                                    5341
```

<210> SEQ ID NO 17
<211> LENGTH: 612
<212> TYPE: DNA
<213> ORGANISM: Pseudomonas putida

<400> SEQUENCE: 17

```
atgagtccaa agagaagaac acaggcagag cgcgcaatgg agacccaggg caagttgatt     60
gcagcggccc tgggggtttt acgggaaaaa ggttacgcgg gattccggat cgcagatgtg    120
cccggtgctg caggtgtctc gagaggagcg cagagccatc atttcccgac aaagcttgag    180
cttctgcttg ccacttttga atggctttac gaacagatca ccgaacgcag tcgggctcga    240
ttagcgaaat tgaagccaga ggatgacgtc atccagcaaa tgctggacga cgccgccgaa    300 ttttttcctcg acgatgactt ctctatcagc cttgatttga ttgtggctgc cgaccgggat    360
ccagcgttac gcgagggtat tcagcgcacg gtagagagga tcggtttgt cgtcgaggat    420 atgtggcttg gtgttctggt gagccgtggt cttttcgcgtg atgatgcaga agatatcctt    480
tggttgatat tcaattcggt gcgtgggctt gctgttcgta gcctatggca aaggacaaa    540 gaacgctttg agcgtgtcag gaactcgaca ctcgaaattg cgcgagagcg gtacgcgaaa    600
ttcaagcgct ag                                                        612
```

<210> SEQ ID NO 18
<211> LENGTH: 203
<212> TYPE: PRT
<213> ORGANISM: Pseudomonas putida

<400> SEQUENCE: 18

```
Met Ser Pro Lys Arg Arg Thr Gln Ala Glu Arg Ala Met Glu Thr Gln
  1               5                  10                  15

Gly Lys Leu Ile Ala Ala Ala Leu Gly Val Leu Arg Glu Lys Gly Tyr
             20                  25                  30

Ala Gly Phe Arg Ile Ala Asp Val Pro Gly Ala Ala Gly Val Ser Arg
         35                  40                  45

Gly Ala Gln Ser His His Phe Pro Thr Lys Leu Glu Leu Leu Leu Ala
     50                  55                  60

Thr Phe Glu Trp Leu Tyr Glu Gln Ile Thr Glu Arg Ser Arg Ala Arg
```

```
                65                  70                  75                  80
Leu Ala Lys Leu Lys Pro Glu Asp Asp Val Ile Gln Gln Met Leu Asp
                    85                  90                  95

Asp Ala Ala Glu Phe Phe Leu Asp Asp Phe Ser Ile Ser Leu Asp
                100                 105                 110

Leu Ile Val Ala Ala Asp Arg Asp Pro Ala Leu Arg Glu Gly Ile Gln
                115                 120                 125

Arg Thr Val Glu Arg Asn Arg Phe Val Val Asp Met Trp Leu Gly
    130                 135                 140

Val Leu Val Ser Arg Gly Leu Ser Arg Asp Asp Ala Glu Asp Ile Leu
145                 150                 155                 160

Trp Leu Ile Phe Asn Ser Val Arg Gly Leu Ala Val Arg Ser Leu Trp
                165                 170                 175

Gln Lys Asp Lys Glu Arg Phe Glu Arg Val Arg Asn Ser Thr Leu Glu
                180                 185                 190

Ile Ala Arg Glu Arg Tyr Ala Lys Phe Lys Arg
                195                 200
```

<210> SEQ ID NO 19
<211> LENGTH: 612
<212> TYPE: DNA
<213> ORGANISM: Artificial Sequence
<220> FEATURE:
<223> OTHER INFORMATION: Mutated CymR sequence from Pseudomonas putida

<400> SEQUENCE: 19

```
atgagtccaa agagaagaac acaggcagag cgcgcaatgg agacccaggg caagttgatt        60
gcagcggccc tgggggtttt acgggaaaaa ggttacgcgg gattccggat cgcagatgtg       120
cccggtgctg caggtgtctc gagaggagcg cagagccatc atttcccgac aaagcttgag       180
cttctgcttg ccacttttga atggctttac gaacagatca ccgaacgcag tcgggctcga       240
ttagcgaaat tgaagccaga ggatgacgtc atccagcaaa tgctggacga cgccgccgaa       300
ttttttcctcg acgatgactt ctctatcagc cttgatttga ttgtggctgc cgaccgggat       360
ccagtcttac gcgagggtat tcagcgcacg gtagagagga tcggtttgt cgtcggcgat       420
atctggcttg tgttctggt gagccgtggt cttttcgcgtg atgatgcaga agatatcctt       480
tggttgatat tcaattcggt gcgtgggctt gctgttcgta gcctatgca aaggacaaa        540
gaacgctttg agcgtgtcag gaactcgaca ctcgaaattg cgcgagagcg gtacgcgaaa       600
ttcaagcgct ag                                                          612
```

<210> SEQ ID NO 20
<211> LENGTH: 203
<212> TYPE: PRT
<213> ORGANISM: Artificial Sequence
<220> FEATURE:
<223> OTHER INFORMATION: Mutated CymR protein from Pseudonomas putida

<400> SEQUENCE: 20

```
Met Ser Pro Lys Arg Arg Thr Gln Ala Glu Arg Ala Met Glu Thr Gln
1               5                   10                  15

Gly Lys Leu Ile Ala Ala Ala Leu Gly Val Leu Arg Glu Lys Gly Tyr
                20                  25                  30

Ala Gly Phe Arg Ile Ala Asp Val Pro Gly Ala Ala Gly Val Ser Arg
            35                  40                  45

Gly Ala Gln Ser His His Phe Pro Thr Lys Leu Glu Leu Leu Leu Ala
        50                  55                  60
```

```
Thr Phe Glu Trp Leu Tyr Glu Gln Ile Thr Glu Arg Ser Arg Ala Arg
 65                  70                  75                  80

Leu Ala Lys Leu Lys Pro Glu Asp Asp Val Ile Gln Gln Met Leu Asp
                 85                  90                  95

Asp Ala Ala Glu Phe Phe Leu Asp Asp Phe Ser Ile Ser Leu Asp
            100                 105                 110

Leu Ile Val Ala Ala Asp Arg Asp Pro Val Leu Arg Glu Gly Ile Gln
            115                 120                 125

Arg Thr Val Glu Arg Asn Arg Phe Val Val Gly Asp Ile Trp Leu Gly
            130                 135                 140

Val Leu Val Ser Arg Gly Leu Ser Arg Asp Asp Ala Glu Asp Ile Leu
145                 150                 155                 160

Trp Leu Ile Phe Asn Ser Val Arg Gly Leu Ala Val Arg Ser Leu Trp
                165                 170                 175

Gln Lys Asp Lys Glu Arg Phe Glu Arg Val Arg Asn Ser Thr Leu Glu
            180                 185                 190

Ile Ala Arg Glu Arg Tyr Ala Lys Phe Lys Arg
            195                 200
```

```
<210> SEQ ID NO 21
<211> LENGTH: 94
<212> TYPE: DNA
<213> ORGANISM: Artificial Sequence
<220> FEATURE:
<223> OTHER INFORMATION: Enhancer

<400> SEQUENCE: 21
ggcgtgtacg gtgggaggtc tataagcca gagctgaaca aacagacaat ctggtctgtt    60
tgtagtttag tgaaccgaga tctttgtcga tcct                               94

<210> SEQ ID NO 22
<211> LENGTH: 194
<212> TYPE: DNA
<213> ORGANISM: Artificial Sequence
<220> FEATURE:
<223> OTHER INFORMATION: Promoter

<400> SEQUENCE: 22
ggcgtgtacg gtgggaggtc tataagcca gagctgaaca aacagacaat ctggtctgtt    60
tgtagtttag tgaaccgaga tctttgtcga tcctaccatc cactcgacac acccgccagc   120
ggccgcaaca aacagacaat ctggtctgtt tgtaagcttc cgagctctcg aattcaaagg   180
aggtacccac catg                                                    194

<210> SEQ ID NO 23
<211> LENGTH: 94
<212> TYPE: DNA
<213> ORGANISM: Artificial Sequence
<220> FEATURE:
<223> OTHER INFORMATION: Enhancer

<400> SEQUENCE: 23
aggatcgaca aagatctcgg ttcactaaac tacaaacaga ccagattgtc tgtttgttca    60
gctctgctta tatagacctc ccaccgtaca cgcc                               94

<210> SEQ ID NO 24
<211> LENGTH: 194
<212> TYPE: DNA
<213> ORGANISM: Artificial Sequence
```

```
<220> FEATURE:
<223> OTHER INFORMATION: Promoter

<400> SEQUENCE: 24
catggtgggt acctcctttg aattcgagag ctcggaagct tacaaacaga ccagattgtc    60
tgtttgttgc ggccgctggc gggtgtgtcg agtggatggt aggatcgaca aagatctcgg   120
ttcactaaac tacaaacaga ccagattgtc tgtttgttca gctctgctta tatagacctc   180
ccaccgtaca cgcc                                                     194
```

INDUCIBLE AAV SYSTEM COMPRISING CUMATE OPERATOR SEQUENCES

CROSS-REFERENCE

This application is a 371 U.S. national phase of PCT/GB2020/050252, filed Feb. 5, 2020, which claims priority from GB 1901571.8, filed Feb. 5, 2019, both which are incorporated by reference in its entirety.

SEQUENCE LISTING STATEMENT

This application includes an electronically submitted Sequence Listing in text format. The text file contains a sequence listing entitled "21-0965-WO-US_Sequence-Listing_ST25.txt" created on Jan. 5, 2022 and is 52 kilobytes in size. The Sequence Listing contained in this text file is part of the specification and is hereby incorporated by reference herein in its entirety.

FIELD OF THE INVENTION

The invention relates to nucleic acid molecules, vectors and plasmids comprising AAV cap genes and rep genes, wherein the cap and rep genes are both operably-associated with an inducible promoter which comprises one or more cumate operator (CuO) sequences. The invention further relates to producer and packaging cell lines which are useful in the production of Adeno-Associated Virus (AAV) particles.

BACKGROUND OF THE INVENTION

AAV vectors are single-stranded DNA viruses that belong to the Parvoviridae family. This virus is capable of infecting a broad range of host cells, including both dividing and non-dividing cells. In addition, it is a non-pathogenic virus that generates only a limited immune response in most patients.

The native AAV genome comprises two genes each encoding multiple open reading frames (ORFs): the rep gene encodes non-structural proteins that are required for the AAV life-cycle and site-specific integration of the viral genome; and the cap gene encodes the structural capsid proteins.

In addition, these two genes are flanked by inverted terminal repeat (ITR) sequences consisting of 145 bases that have the ability to form hairpin structures. These hairpin sequences are required for the primase-independent synthesis of a second DNA strand and the integration of the viral DNA into the host cell genome.

In order to eliminate any integrative capacity of the virus, recombinant AAV vectors remove rep and cap from the DNA of the viral genome. To produce such vectors, the desired transgene(s), together with a promoter(s) to drive transcription of the transgene(s), is inserted between the inverted terminal repeats (ITRs); and the rep and cap genes are provided in trans in a second plasmid. A third plasmid, providing helper genes such as adenovirus E4, E2a and VA genes, is also used. All three plasmids are then transfected into cultured mammalian cells, such as HEK293.

Over the last few years, AAV vectors have emerged as an extremely useful and promising mode of gene delivery. This is owing to the following properties of these vectors:

AAVs are small, non-enveloped viruses and they have only two native genes (rep and cap). Thus they can be easily manipulated to develop vectors for different gene therapies.

AAV particles are not easily degraded by shear forces, enzymes or solvents. This facilitates easy purification and final formulation of these viral vectors.

AAVs are non-pathogenic and have a low immunogenicity. The use of these vectors further reduces the risk of adverse inflammatory reactions. Unlike other viral vectors, such as lentivirus, herpes virus and adenovirus, AAVs are harmless and are not thought to be responsible for causing any human disease.

Genetic sequences up to approximately 4500 bp can be delivered into a patient using AAV vectors.

Whilst wild-type AAV vectors have been shown to sometimes insert genetic material into human chromosome 19, this property is generally eliminated from most AAV vectors by removing rep and cap genes from the viral genome. In such cases, the virus remains in an episomal form within the host cells. These episomes remain intact in non-dividing cells, while in dividing cells they are lost during cell division.

In addition to being involved in AAV DNA replication and gene regulation, the Rep proteins are known to have cytostatic and cytotoxic effects on cells which express them.

HEK293 cell lines expressing Rep proteins typically grow more slowly, with colony-forming efficiency reduced by over 90% when cell lines express Rep 78. The cells look morphologically typical, but are increasingly found in S-phase, suggesting they do not introduce a cell cycle block but slow or inhibit the cell cycle.

The cytostatic and cytopathic effects of the large Rep proteins have the potential to be deleterious to a stable cell line expressing AAV packaging genes if expressed constitutively. In the native configuration, the large Rep proteins are expressed from the p5 promoter, which is itself activated by the large Rep proteins and adenoviral helper genes. The small Rep proteins, Rep 52 and Rep 40, are expressed from the p19 promoter, which is found within the rep gene and is activated by the larger Rep proteins.

SUMMARY OF THE INVENTION

The invention relates to nucleic acid molecules, vectors and plasmids comprising AAV cap genes and rep genes, wherein the cap and rep genes are both operably-associated with an inducible promoter which comprises one or more cumate operator (CuO) sequences. The invention further relates to producer and packaging cell lines which are useful in the production of Adeno-Associated Virus (AAV) particles.

The inventors have recognised that constitutive expression of the rep genes in cell lines is undesirable and that it would be advantageous to control expression of the rep genes from an inducible promoter. Furthermore, induction should allow sufficient rep gene expression to allow for the production of high titres of AAV.

A very wide variety of methods exist to regulate gene expression in mammalian cells using inducible systems. Examples include the Tet and lac operon-based systems, riboswitches, Cre-loxP/FLP-FRT (and conditional variants) and light and temperature sensitive regulators. Transcriptional activators may also be constructed using modified forms of gene editing technologies such as CRIPSR/Cas9, Zinc-Fingers, and other nuclease-deficient DNA targeting mechanisms.

It is widely known in the art that promoters can be modified to contain DNA sequences targeted by pre-existing DNA targeting proteins, or can be specifically targetted using programmable methods (e.g. CRISPR) (e.g. Maximilian Hörner, Wilfried Weber, Molecular switches in animal cells, FEBS Letters, Volume 586, Issue 15, 2012, pages 2084-2096).

After testing a number of different systems and promoters using reporter genes and in AAV production assays, the inventors have found that a system based around a minimal promoter which comprises one or more cumate operator sites (CuOs) provides a high level of control over AAV gene transcription.

DESCRIPTION OF THE DRAWINGS

FIG. 3A. Position of CuO site in enhancer region (SEQ ID No: 21, and reverse complement is SEQ ID NO:23).

FIG. 3B. Positioning of second downstream CuO relative to transcription start site (SEQ ID No: 22, and reverse complement is SEQ ID NO:24).

DETAILED DESCRIPTION OF THE INVENTION

Cumate operator sites (abbreviated herein as "CuOs") are DNA elements which are capable of being bound by a cumate repressor protein (CymR). The CuO is therefore a DNA recognition sequence for CymRs.

In the absence of the cumate small molecule, the cumate-repressor protein (CymR) binds to cumate operator sites (CuO) within an associated promoter. Where the operator sites are proximal to the minimal/core promoter region, the CymR protein sterically blocks formation of the transcription initiation complex and thus prevents transcription.

In the presence of cumate, the CymR protein undergoes a conformational change, altering its DNA-binding properties and reducing its affinity for the CuO sites. Thus in the presence of cumate the repression of promoter activity via CymR binding is relieved and transcription proceeds.

4-Isopropylbenzoic Acid (Cumate)

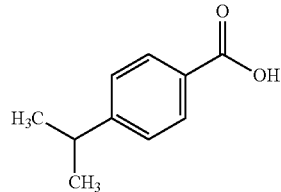

Uses of CuO sites and the CymR protein are known in the art (e.g. "High-level recombinant protein production in CHO cells using lentiviral vectors and the cumate gene-switch", Gaillet B, et al. Biotechnol. Bioeng. 2010 Jun. 1; 106(2): 203-15. doi: 10.1002/bit.22698).

Cumate-based systems have not, however, previously been used in the context of the regulation of AAV genes. This is in part because the genetics of AAV are complex, with all existing systems using the native promoters found within the AAV virus as it is in nature to drive Rep and Cap expression. The inventors determined that it was possible to change the expression context of both Rep and Cap such that they were controlled by a single polymerase II promoter to drive expression of the main AAV genes. Only once this had been achieved did it then become apparent that the expression of these genes could be regulated using an inducible system such as when using Cumate.

The invention does not, however, use cumate in the standard manner, i.e. to relieve repression due to the binding of a CymR polypeptide to a CuO site.

In one aspect, the invention relates to a packaging cell line wherein the AAV cap and rep genes—in reverse order compared to their wild type configuration—are placed under the control of a minimal promoter which comprises one or more CuO sites. Placing the cap and rep genes in this reverse order has the advantage of optimising the ratios and amounts of Rep and Cap proteins which are produced during the AAV vector production process. Induction of cap and rep expression, as a single transcript, is then achieved by induction with a CymR-transcriptional activator domain polypeptide. This may be provided from a plasmid which is transfected into the cell.

Figure 1A:
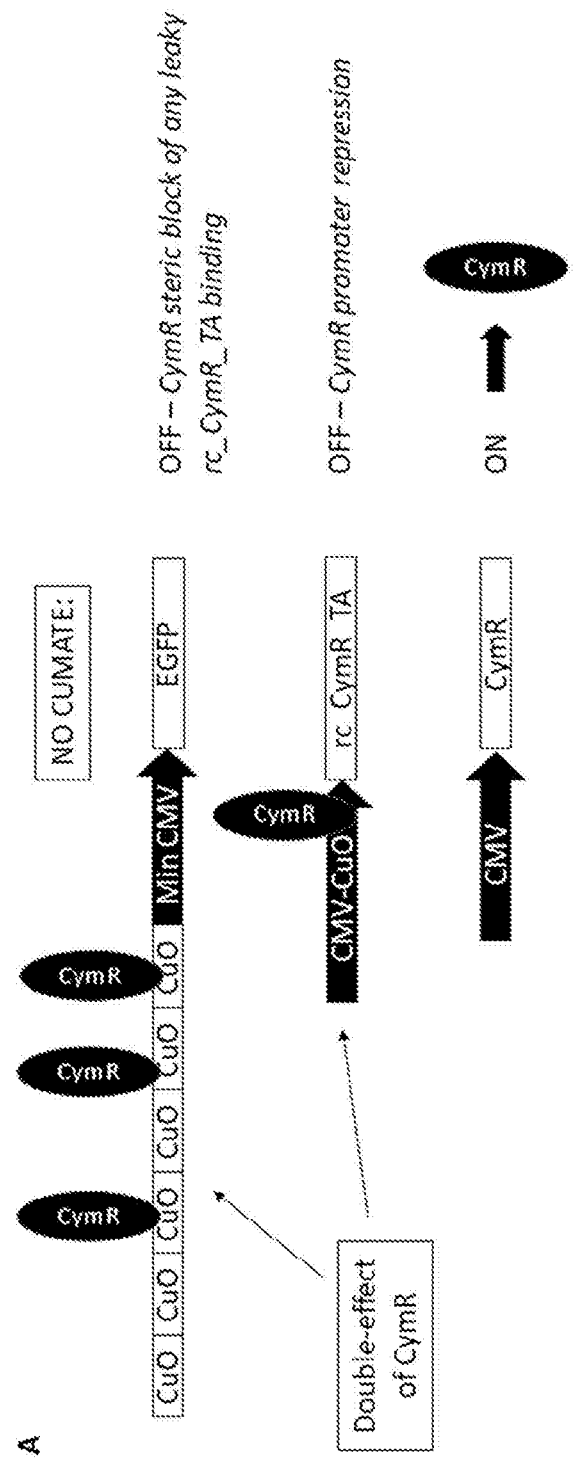
FIG. 1A. Schematic diagram of dual cumate control system in the absence of cumate where the target regulated gene is transcriptionally off.
Figure 1B:
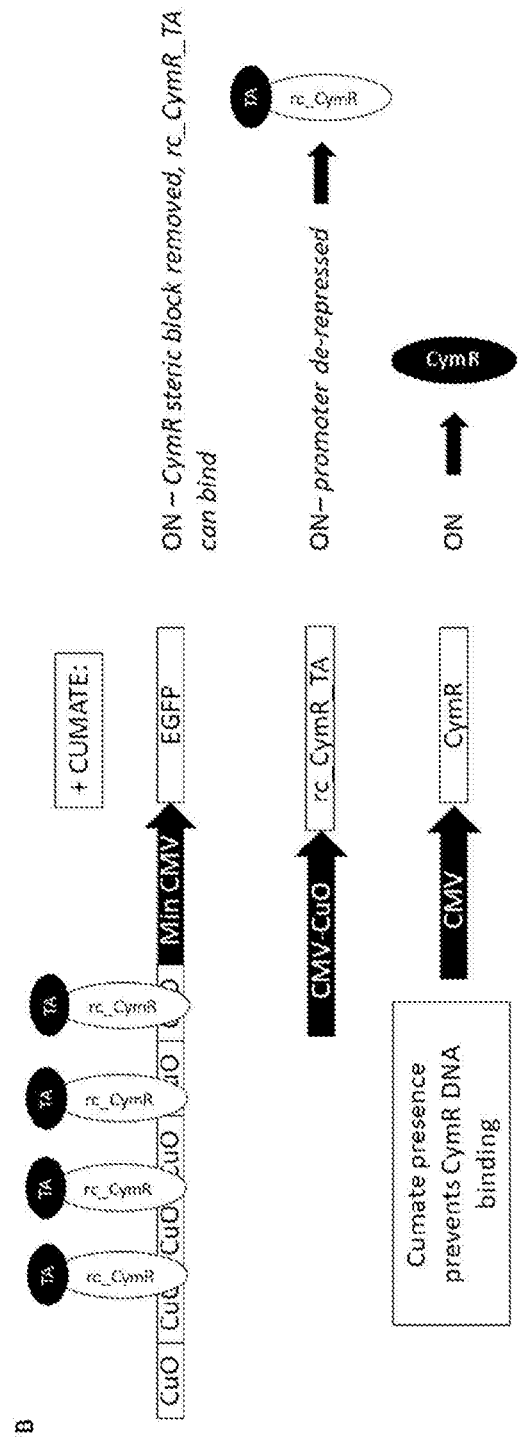
FIG. 1B. Schematic diagram of dual cumate control system where addition of cumate relieves all modes of repression allowing activation of target regulated gene.

In a further aspect, the invention relates to a complex dual-control system for controlling expression of AAV genes in a producer cell line. The producer cell line comprises a number of DNA constructs integrated into its genome: The first DNA construct comprises cap and rep genes under the control of a minimal promoter, wherein the promoter comprises one or more CuO sites. The second construct comprises a gene encoding a reverse cumate repressor (rcCymR) polypeptide linked to a transcriptional activator domain under the control of a promoter which comprises at least one CuO site. The third DNA construct comprises a gene encoding a CymR polypeptide under the control of a constitutive promoter. In this dual control aspect, in the absence of cumate, the CymR binds to the promoter region of the rcCymR gene and represses its transcription; the CymR also binds to the minimal promoters driving the cap-rep (and/or Adenoviral) genes, sterically blocking any residual rcCymR-TAD binding. In the presence of cumate, the repression of rcCymR-TAD transcription is relieved, as is the steric blocking, and the rcCymR-TAD is allowed to bind to the promoter of the cap-rep genes (and/or Adenoviral genes), and activates transcription—resulting in rAAV production. Cumate may be introduced into the cell by adding cumate into the media surrounding the cell, at the desired time. This aspect is illustrated in FIGS. 1A and 1B.

In addition to regulating expression of the Rep and Cap proteins, the same systems may be used to regulate the expression of Adenoviral proteins (e.g. E4) which may also be present in the packaging or producer cell lines, and which may have cytotoxic or cytostatic effects.

The invention also provides nucleic acid constructs for use with the cell packaging and producer cell lines.

The use of a cumate-based system has particular advantages over antibiotics-based systems in that the possibility of contaminating antibiotics being a carried over into the final AAV preparations is removed. Furthermore, in the context described here, the system allows for a genetic-based induction system in the packaging cell line (CymR-TAD is encoded on a transgene plasmid and transfected), and a chemical-based induction system in the producer cell line, without changing the underlying configuration of the integrated AAV and Adenoviral genes (i.e. a packaging cell line is used to make the producer cell line). All of these processes can be used in a Good Manufacturing Process (GMP) with reduced safety concerns.

The systems of the invention also provide a high level of control over AAV gene transcription, with reduced 'off' state expression levels and high cony state expression levels.

In one embodiment, the invention provides a nucleic acid molecule, vector or plasmid comprising:
 (i) a promoter comprising one or more cumate operator sites,
 (ii) a cap gene, and
 (iii) a rep gene, wherein the rep gene preferably encodes Rep78 and Rep68, in the above 5'-3' order, wherein the cap gene and the rep gene are both operably associated with the promoter.

In another embodiment, the invention provides a cell line, comprising:
 (A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order, wherein the cap gene and the rep gene are both operably associated with the promoter;
 and optionally one of more of the following:
 (B) a nucleic acid molecule, vector or plasmid comprising:
  (i) a promoter (preferably a minimal promoter) comprising one or more cumate operator sites, operably associated with
  (ii) a gene encoding a rc-CymR-TAD polypeptide;
 (C) a nucleic acid molecule, vector or plasmid comprising:
  (i) a promoter (preferably a constitutive promoter), operably associated with
  (ii) a gene encoding CymR;
 (D) a nucleic acid molecule, vector or plasmid comprising:
  (i) a promoter (preferably a constitutive promoter), operably associated with
  (ii) a gene encoding a CymR-TAD polypeptide;
 (E) a nucleic acid molecule, vector or plasmid comprising:
  (i) one or more promoters, which may or may not comprise one or more cumate operator sites, operably associated with
  (ii) one or more adenoviral genes which are competent to support AAV production, preferably E4 and/or VAI-RNA;
 (F) a nucleic acid molecule, vector or plasmid comprising:
  (i) a promoter, operably associated with
  (ii) a transgene,
 wherein the promoter and transgene are flanked by ITRs.

In a further embodiment, there is provided a process for producing an AAV cell line, the process comprising the steps of integrating into the genome of the cells of the cell line:
 (A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order,
  wherein the cap gene and the rep gene are both operably associated with the promoter, thereby producing a cell that inducibly expresses viral cap and rep genes; and optionally one of more of the following:
 (B) a nucleic acid molecule, vector or plasmid comprising:
  (i) a promoter (preferably a minimal promoter) comprising one or more cumate operator sites, operably associated with
  (ii) a gene encoding a rc-CymR-TAD polypeptide;
 (C) a nucleic acid molecule, vector or plasmid comprising:
  (i) a promoter (preferably a constitutive promoter), operably associated with
  (ii) a gene encoding CymR;
 (E) a nucleic acid molecule, vector or plasmid comprising:
  (i) one or more promoters, which may or may not comprise one or more cumate operator sites, operably associated with
  (ii) one or more adenoviral genes which are competent to support AAV production, preferably E4 and/or VAI-RNA.

The invention also provides a method of inducing transcription of cap and rep genes in a cell, the method comprising the steps:
 inducing the transcription of cap and rep genes in a cell which comprises in its genome:
 (A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order, wherein the cap gene and the rep gene are both operably associated with the promoter,
wherein the inducing is by the presence, in the cell, of a CymR-TAD polypeptide.

The invention also provides a method of inducing transcription of cap and rep genes in a cell, the method comprising the steps:
inducing the transcription of cap and rep genes in a cell which comprises in its genome:
(A) a nucleic acid molecule, vector or plasmid comprising:
 (i) a promoter comprising one or more cumate operator sites,
 (ii) a cap gene, and
 (iii) a rep gene, wherein the rep gene preferably encodes Rep78 and Rep68, in the above 5'-3' order, wherein the cap gene and the rep gene are both operably associated with the promoter;
(B) a nucleic acid molecule, vector or plasmid comprising:
 (i) a promoter comprising one or more cumate operator sites, operably associated with
 (ii) a gene encoding a rc-CymR-TAD polypeptide;
(C) a nucleic acid molecule, vector or plasmid comprising:
 (i) a promoter, operably associated with
 (ii) a gene encoding CymR;
and optionally
(D) a nucleic acid molecule, vector or plasmid comprising:
 (i) one or more promoters, which may or may not comprise one or more cumate operator sites, operably associated with
 (ii) one or more adenoviral genes which are competent to support AAV production, preferably E4 and/or VAI-RNA;
and/or
(E) a nucleic acid molecule, vector or plasmid comprising:
 (i) a promoter, operably associated with
 (ii) a transgene,
 wherein the promoter and transgene are flanked by ITRs,
wherein (A), (B), (C), (D) and (E), when present, are preferably all integrated into the genome of the cell, wherein the inducing is by the presence, in the cell, of cumate.

The nucleic acid molecule may be DNA or RNA, preferably DNA. The nucleic acid molecule may be single- or double-stranded, preferably double-stranded.

In one embodiment, the invention provides a nucleic acid molecule, vector or plasmid comprising:
 (i) a promoter comprising one or more cumate operator sites,
 (ii) a cap gene, and
 (iii) a rep gene, wherein the rep gene preferably encodes Rep78 and Rep68, in the above 5'-3' order, wherein the cap gene and the rep gene are both operably associated with the promoter.

In this embodiment, the promoter is preferably a minimal promoter. The cap gene and the rep gene are both operably associated with the promoter. This will result in a single primary transcript that comprises coding sequences from both cap and rep genes. As used herein, the term "minimal promoter" refers to any DNA sequence which is capable of recruiting the basal transcription complex to a DNA molecule. Preferably, the minimal promoter includes an InR box and/or a Downstream Promoter Element (DPE) box and/or a TATA box sequence. A minimal promoter excludes promoter elements which are normally found upstream of the TATA box, such as enhancer sequences. A minimal promoter is capable of initiating only low levels of transcription. The minimal promoter may also be called a basally inactive promoter (i.e. active only at a base level in the absence of other genetic elements).

Preferably, the minimal promoter is a minimal pol II promoter. Examples of minimal promoters include promoters which are derived from the CMV, SV40, PGK (human or mouse), HSV TK, SFFV, Ubiquitin, Elongation Factor Alpha, CHEF-1, FerH, Grp78, RSV, Adenovirus E1A, CAG or CMV-Beta-Globin promoter.

Preferably, the minimal promoter is derived from the cytomegalovirus immediate early (CMV) promoter, or a promoter of equal or increased strength compared to the CMV promoter in human cells and human cell lines (e.g. HEK-293 cells).

In some embodiments, the promoter comprises one or more cumate operator sites. As used herein, the term cumate operator site (which may be abbreviated herein as "CuO") refers to a DNA element which is capable of being bound by a cumate repressor protein (CymR). The CuO is therefore a DNA recognition sequence for CymR.

Preferably, the CuO site has the sequence: AGAAACAAACCAACCTGTCTGTATTA (SEQ ID NO: 12) or a variant thereof which is capable of being bound by CymR.

In some preferred embodiments, the promoter comprises a plurality of CuO sites, most preferably 6 CuO sites. Preferably, the sequence of the 6 CuO sites is: AGAAACAAACCAACCTGTCTGTATTAT-CAAAGAAACAAACCAACCTGTCTGTATTAT CAAAGAAACAAACCAACCTGTCTGTATTAT-CAAAGAAACAAACCAACCTGTCTGTAT TAT-CAAAGAAACAAACCAACCTGTCTGTATTAT-CAAAGAAACAAACCAACCTGTCTG TATTA (SEQ ID NO: 13) or a variant thereof which is capable of being bound by a plurality of CymR molecules.

In some embodiments, the promoter comprises 1, 2, 3, 4, 5, 6, 7, 8, 9 or 10 CuO sites. In some embodiments, the promoter preferably comprises 4, 5, 6, 7, 8 or 9 CuO sites, most preferably 6 CuO sites.

In other embodiments (e.g. the promoter which is operably associated with a gene encoding a rc-CymR-TAD polypeptide), the promoter comprises only 1, 2 or 3 CuO sites, preferably only 1 CuO site.

Preferably, the CuO site(s) in the promoter are placed upstream of both the TATA box and the +1 site.

The CuO site(s) may also be placed downstream of the +1 site at any distance up to the ATG start codon of the first coding sequence.

In embodiments of the invention which comprise more than one CuO site, the CuO sites may be joined contiguously or non-contiguously. Preferably, the CuO sites are separated by linker nucleotide sequences. The linker nucleotide sequences may, for example, be 5-20, preferably 7-15 and most preferably about 10 nucleotides. In some embodiments, the linker sequences are 4 nucleotides.

In some other embodiments (e.g. the promoter which is operably associated with a gene encoding a CymR or CymR-TAD polypeptide), the promoter is preferably a constitutive promoter.

Examples of constitutive promoters include the CMV, SV40, PGK (human or mouse), HSV TK, SFFV, Ubiquitin, Elongation Factor Alpha, CHEF-1, FerH, Grp78, RSV, Adenovirus E1A, CAG or CMV-Beta-Globin promoter, or a promoter derived therefrom. Preferably, the promoter is the cytomegalovirus immediate early (CMV) promoter, or a promoter which is derived therefrom, or a promoter of equal or increased strength compared to the CMV promoter in human cells and human cell lines (e.g. HEK-293 cells). Preferably, the promoter which is operably-associated with the cap and rep genes is not an AAV promoter, e.g. it is not an AAV p5, p19 or p40 promoter.

The nucleic acid molecule of the invention comprises a rep gene. The rep gene preferably encodes Rep78 and Rep68. As used herein, the term "rep gene" refers to a gene that encodes one or more open reading frames (ORFs), wherein each of said ORFs encodes an AAV Rep non-structural protein, or variant or derivative thereof. These AAV Rep non-structural proteins (or variants or derivatives thereof) are involved in AAV genome replication and/or AAV genome packaging.

Figure 2:
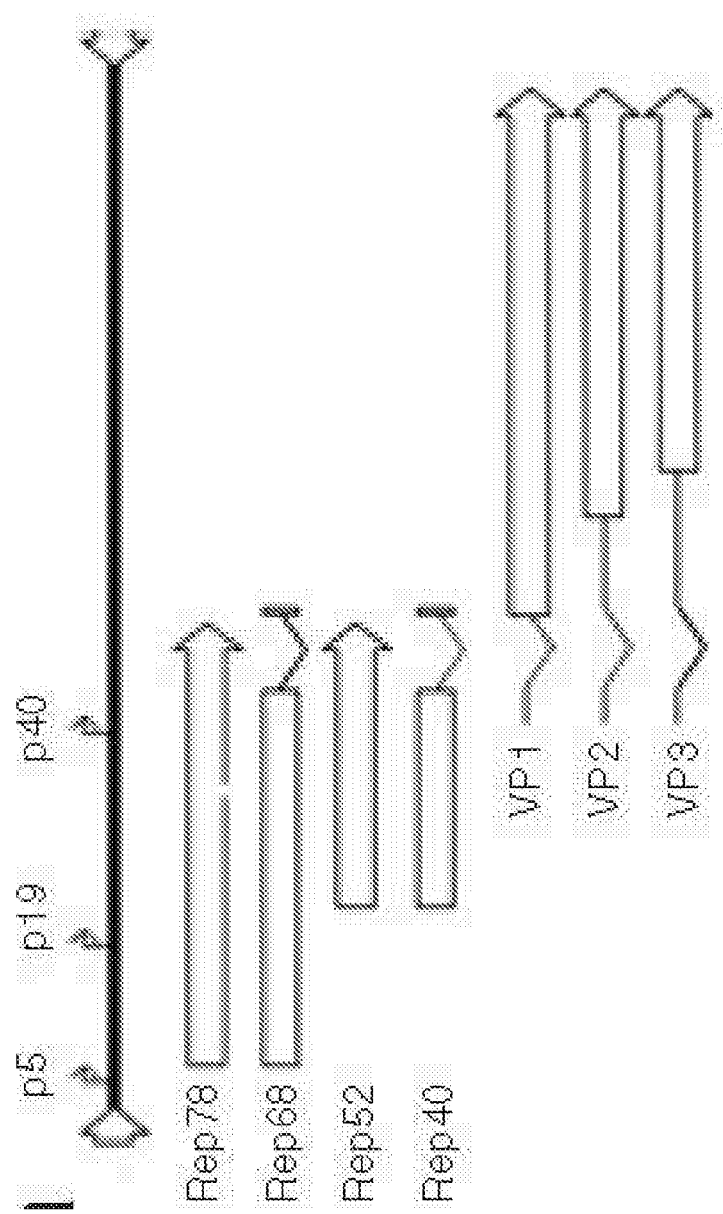
FIG. 2 shows the organisation of the Rep and Cap protein genes in the wild-type AAV genome.

The structure of the wild-type AAV genome, illustrating the organisation of the wild-type rep and cap genes, is shown in FIG. 2.

The wild-type rep gene comprises three promoters: p5, p19 and p40. Two overlapping messenger ribonucleic acids (mRNAs) of different lengths can be produced from p5 and from p19. Each of these mRNAs contains an intron which can be either spliced out or not using a single splice donor site and two different splice acceptor sites. Thus, six different mRNAs can be formed, of which only four are functional. The two mRNAs that fail to remove the intron (one transcribed from p5 and one from p19) read through to a shared terminator sequence and encode Rep78 and Rep52, respectively. Removal of the intron and use of the 5'-most splice acceptor site does not result in production of any functional Rep protein—it cannot produce the correct Rep68 or Rep40 proteins as the frame of the remainder of the sequence is shifted, and it will also not produce the correct C-terminus of Rep78 or Rep52 because their terminator is spliced out. Conversely, removal of the intron and use of the 3' splice acceptor will include the correct C-terminus for Rep68 and Rep40, whilst splicing out the terminator of Rep78 and Rep52. Hence the only functional splicing either avoids splicing out the intron altogether (producing Rep78 and Rep52) or uses the 3' splice acceptor (to produce Rep68 and Rep40). Consequently, four different functional Rep proteins with overlapping sequences can be synthesized from these promoters.

In the wild-type rep gene, the p40 promoter is located at the 3' end. Transcription of the Cap proteins (VP1, VP2 and VP3) is initiated from this promoter in the wild-type AAV genome.

The four wild-type Rep proteins are Rep78, Rep68, Rep52 and Rep40. Hence the wild-type rep gene is one which encodes the four Rep proteins Rep78, Rep68, Rep52 and Rep40.

Rep78 and 68 can specifically bind the hairpin formed by the ITR and cleave it at a specific region (i.e. the terminal resolution site) within the hairpin. In the wild-type virus, they are also necessary for the AAV-specific integration of the AAV genome. Rep 78 and Rep68 are transcribed under control of the p5 promoter in the wild type virus, and the difference between them reflects removal (or not) of an intron by splicing, hence they have different C terminal protein composition.

Rep52 and Rep40 are involved in genome packaging. Rep52 and Rep40 are transcribed under control of the p19 promoter in the wild type virus, and the difference between them reflects removal (or not) of an intron by splicing, hence they have different C terminal protein composition.

All four Rep proteins bind ATP and possess helicase activity. They up-regulate transcription from the p40 promoter, but down-regulate both p5 and p19 promoters.

As used herein, the term "rep gene" includes wild-type rep genes and derivatives thereof; and artificial rep genes which have equivalent functions.

In one embodiment, the rep gene encodes functional Rep78, Rep68, Rep52 and Rep40 proteins.

In a preferred example of this embodiment, Rep78 and Rep 68 are translated by ribosomes docking 5' to the Rep78 and Rep68 ATG start codon, thus allowing production of both of these proteins. In this example, the Rep78 and Rep68 open reading frames contain an active p40 promoter that provides the expression of both Rep52 and Rep40.

In some embodiments of the invention, the function of one or more of the p5, p19 and p40 promoters is removed/disabled, for example by codon-changing and/or removal of the TATA box, in order to prevent unwanted initiation of transcription from that promoter.

Preferably, the p5 promoter is non-functional (i.e. it cannot be used to initiate transcription). More preferably, the p5 promoter is replaced with the IRES (thus removing the function of the p5 promoter). This allows Rep78 or Rep68 to be transcribed in the same mRNA as the cap genes, but translation of the Rep78 and Rep68 proteins will be under the control of the IRES.

A further advantage of the removal of the p5 promoter is that, in the wild-type virus, the p5 promoter is bound by and is activated by the E2A DNA-binding protein (DBP). Hence the removal of the p5 promoter means that the E2A gene is not required (e.g. in a Helper Plasmid) to produce virus particles.

In one embodiment, the rep gene does not have a p5 promoter upstream. In another embodiment, the p5 promoter is not used in AAV packaging.

Preferably, the p19 promoter within the rep gene is functional.

In some embodiments, the function of the p40 promoter is removed/disabled within the Rep gene by one or more codon changes.

The cap gene is preferably relocated and its transcription is placed under control of an alternative promoter (e.g. CMV immediate early promoter).

There is a degree of redundancy between the function of the different Rep proteins and hence, in some embodiments of the invention, not all of the Rep proteins are required.

In some embodiments, the rep gene only encodes one, two, three or four of Rep78, Rep68, Rep52 and Rep40, preferably one, two or four of Rep78, Rep68, Rep52 and Rep40.

In some embodiments, the rep gene does not encode one or more of Rep78, Rep68, Rep52 and Rep40.

In some embodiments, the rep gene encodes Rep78 and Rep52, but does not encode Rep68 or Rep40. In this embodiment, the splice donor site remains in the DNA but both the 5' and 3' splice acceptor sites are removed. Hence the intron cannot be removed by splicing and transcription continues through to the terminator sequence for Rep78 and Rep52 (which is common to both). The Rep78 protein is transcribed in the same mRNA as the cap gene (hence is driven by the same promoter), and translation of Rep78 is driven by the IRES. Transcription of Rep52 is driven by the p19 promoter; hence it forms a separate mRNA and is translated by 5' m⁷G cap-dependent docking at the ribosome. Accordingly, Rep68 and Rep40 cannot be produced in this embodiment.

In other embodiments, the rep gene encodes Rep68 and Rep40, but does not encode Rep78 or Rep52. In this embodiment, the intronic sequence between the splice donor and 3' splice acceptor is removed at the DNA level, placing the C terminus of Rep68 and Rep40 in frame with the upstream coding sequence. Hence Rep68 and Rep40 (but not Rep78 and Rep52) are produced. For clarity, Rep68 is transcribed in the same mRNA as the Cap proteins and it is translated under control of the IRES. In contrast, Rep40 is transcribed into a separate mRNA by the p19 promoter and it is translated by 5' m⁷G cap docking at the ribosome.

In some preferred embodiments, the rep gene encodes Rep78 and Rep68, but does not encode Rep52 or Rep40. This may be achieved by mutating the p19 promoter (e.g. inserting a mutation at the p19 TATA box).

In some embodiments, the rep gene encodes Rep52 and Rep40, but does not encode Rep78 or Rep68. This may be achieved by including just the coding sequence from the ATG of Rep52/40.

Preferably, the rep gene encodes Rep78 and Rep68, but does not encode Rep52 or Rep40.

As used above, the term "encodes" means that the rep gene encodes a functional form of that Rep protein. Similarly, the term "does not encode" means that the rep gene does not encode a functional form of that Rep protein.

In the absence of sufficient Rep proteins, lower titres (e.g. genome copies) would be observed (which could be determined by qPCR), due to the fact that there is less ITR plasmid to be packaged and that it would not be effectively packaged. The observation might also include an exaggerated empty:full particle ratio; this could be determined by ELISA or optical density measurement.

The wild-type AAV (serotype 2) rep gene nucleotide sequence is given in SEQ ID NO: 1. The wild-type AAV (serotype 2) Rep78, Rep68, Rep52 and Rep40 amino acid sequences are given in SEQ ID NOs: 2, 3, 4 and 5, respectively. The wild-type AAV (serotype 2) nucleotide sequence encoding Rep78 is given in SEQ ID NO: 6. The wild-type AAV (serotype 2) nucleotide sequence encoding Rep68 is given in SEQ ID NO: 7.

The wild-type AAV (serotype 2) nucleotide sequence encoding Rep52 is given in SEQ ID NO: 8. The wild-type AAV (serotype 2) nucleotide sequence encoding Rep 40 is given in SEQ ID NO: 9.

In one embodiment, the term "rep gene" refers to a nucleotide sequence having at least 70%, 80%, 85%, 90%, 95%, 99% or 100% sequence identity to SEQ ID NO: 1 and which encodes one or more Rep78, Rep68, Rep52 and Rep40 polypeptides.

In another embodiment, the term "rep gene" refers to a nucleotide sequence having at least 70%, 80%, 85%, 90%, 95%, 99% or 100% sequence identity to SEQ ID NO: 6 and which encodes functional Rep78 and/or Rep52 polypeptides (and preferably does not encode functional Rep68 or Rep40 polypeptides).

In another embodiment, the term "rep gene" refers to a nucleotide sequence having at least 70%, 80%, 85%, 90%, 95%, 99% or 100% sequence identity to SEQ ID NO: 7 and which encodes functional Rep68 and/or Rep40 polypeptides (and preferably does not encode functional Rep78 or Rep52 polypeptides).

In another embodiment, the term "rep gene" refers to a nucleotide sequence having at least 70%, 80%, 85%, 90%, 95%, 99% or 100% sequence identity to SEQ ID NO: 8 and which encodes a functional Rep52 polypeptide (and preferably does not encode a functional Rep78 polypeptide).

In another embodiment, the term "rep gene" refers to a nucleotide sequence having at least 70%, 80%, 85%, 90%, 95%, 99% or 100% sequence identity to SEQ ID NO: 9 and which encodes a functional Rep40 polypeptide (and preferably does not encode functional Rep68 polypeptide).

In another embodiment, the term "rep gene" refers to a nucleotide sequence having at least 90%, 95%, 99% or 100% sequence identity to a nucleotide sequence which encodes SEQ ID NO: 2 and which encodes functional Rep78 and/or Rep52 polypeptides (and preferably does not encode functional Rep68 or Rep40 polypeptides).

In another embodiment, the term "rep gene" refers to a nucleotide sequence having at least 90%, 95%, 99% or 100% sequence identity to a nucleotide sequence which encodes SEQ ID NO: 3 and which encodes functional Rep68 and/or Rep40 polypeptides (and preferably does not encode functional Rep78 or Rep52 polypeptides).

In another embodiment, the term "rep gene" refers to a nucleotide sequence having at least 90%, 95%, 99% or 100% sequence identity to a nucleotide sequence which encodes SEQ ID NO: 4 and which encodes a functional Rep52 polypeptide (and preferably does not encode a functional Rep78 polypeptide).

In another embodiment, the term "rep gene" refers to a nucleotide sequence having at least 90%, 95%, 99% or 100% sequence identity to a nucleotide sequence which encodes SEQ ID NO: 5 and which encodes a functional Rep40 polypeptide (and preferably does not encode functional Rep68 polypeptide).

In some embodiments, the nucleic acid molecule of the invention does not encode a functional Rep78 polypeptide. In some embodiments, the nucleic acid molecule of the invention does not encode a functional Rep68 polypeptide. In some embodiments, the nucleic acid molecule of the invention does not encode a functional Rep52 polypeptide. In some embodiments, the nucleic acid molecule of the invention does not encode a functional Rep40 polypeptide.

The nucleic acid molecule also comprises a cap gene. As used herein, the term "cap gene" refers to a gene that encodes one or more open reading frames (ORFs), wherein each of said ORFs encodes an AAV Cap structural protein, or variant or derivative thereof. These AAV Cap structural proteins (or variants or derivatives thereof) form the AAV capsid.

The three Cap proteins must function to enable the production of an infectious AAV virus particle which is capable of infecting a suitable cell. The three Cap proteins are VP1, VP2 and VP3, which are generally 87 kDa, 72 kDa and 62 kDa in size, respectively. Hence the cap gene is one which encodes the three Cap proteins VP1, VP2 and VP3.

In the wild-type AAV, these three proteins are translated from the p40 promoter to form a single mRNA. After this mRNA is synthesized, either a long or a short intron can be excised, resulting in the formation of a 2.3 kb or a 2.6 kb mRNA.

Usually, especially in the presence of adenovirus, the long intron is excised. In this form the first AUG codon, from which the synthesis of VP1 protein starts, is cut out, resulting in a reduced overall level of VP1 protein synthesis. The first AUG codon that remains is the initiation codon for VP3 protein. However, upstream of that codon in the same open reading frame lies an ACG sequence (encoding threonine) which is surrounded by an optimal Kozak context. This contributes to a low level of synthesis of VP2 protein, which is actually VP3 protein with additional N terminal residues, as is VP1.

If the long intron is spliced out, and since in the major splice the ACG codon is a much weaker translation initiation signal, the ratio at which the AAV structural proteins are synthesized in vivo is about 1:1:10, which is the same as in the mature virus particle. The unique fragment at the N-terminus of VP1 protein has been shown to possess phospholipase A2 (PLA2) activity, which is probably required for the releasing of AAV particles from late endosomes.

The AAV capsid is composed of 60 capsid protein subunits (VP1, VP2, and VP3) that are arranged in an icosahedral symmetry in a ratio of 1:1:10, with an estimated size of 3.9 MDa.

As used herein, the term "cap gene" includes wild-type cap genes and derivatives thereof, and artificial cap genes which have equivalent functions.

The AAV (serotype 2) cap gene nucleotide sequence and Cap polypeptide sequences are given in SEQ ID NOs: 10 and 11, respectively.

As used herein, the term "cap gene" refers preferably to a nucleotide sequence having the sequence given in SEQ ID NO: 10 or a nucleotide sequence encoding SEQ ID NO: 11; or a nucleotide sequence having at least 70%, 80%, 85% 90%, 95% or 99% sequence identity to SEQ ID NO: 10 or at least 80%, 90%, 95% or 99% nucleotide sequence identity to a nucleotide sequence encoding SEQ ID NO: 11, and which encodes VP1, VP2 and VP3 polypeptides.

The rep and cap genes are preferably viral genes or derived from viral genes. More preferably, they are AAV genes or derived from AAV genes. In some embodiments, the AAV is an Adeno-associated dependoparvovirus A. In other embodiments, the AAV is an Adeno-associated dependoparvovirus B.

11 different AAV serotypes are known. All of the known serotypes can infect cells from multiple diverse tissue types. Tissue specificity is determined by the capsid serotype. The AAV may be from serotype 1, 2, 3, 4, 5, 6, 7, 8, 9, 10 or 11. Preferably, the AAV is serotype 1, 2, 5, 6, 7, 8 or 9. Most preferably, the AAV serotype is 5 (i.e. AAV5).

The rep and cap genes (and each of the protein-encoding ORFs therein) may be from one or more different viruses (e.g. 2, 3 or 4 different viruses). For example, the rep gene may be from AAV2, whilst the cap gene may be from AAV5.

It is recognised by those in the art that the rep and cap genes of AAV vary by clade and isolate. The sequences of these genes from all such clades and isolates are encompassed herein, as well as derivatives thereof.

The cap gene and rep gene are present in the nucleic acid in this cap-rep 5'→3' order. However, since Rep52 and/or Rep40 may be transcribed from their own p19 promoter, the position of the coding sequence which encodes Rep52 and/or Rep40 may be varied. For example, the coding sequence which encodes Rep52 and/or Rep40 may be placed upstream or downstream of the cap genes and rep genes which encode Rep78/68; or indeed on the reverse strand of the nucleic acid of the invention or on a different nucleic acid.

Translation of the cap gene is preferably initiated from the standard 5' m⁷G-cap at the 5' end of the mRNA.

A single mRNA transcript will be produced which encodes both the Cap and Rep polypeptides. Additional measures may be taken in order to promote appropriate levels of translation of the (downstream) Rep polypeptide. These measures include:

(a) inserting an IRES site between the cap and rep genes;
(b) production of a Cap-Rep fusion polypeptide and its subsequent cleavage into separate polypeptides; and
(c) use of alternative splicing to produce separate Cap and Rep polypeptides. Each of these measures are discussed further below.

The rep gene may be operably-associated with an Internal Ribosome Entry Site (IRES). The IRES regulates the translation of the rep mRNA. IRESs are distinct regions of nucleic acid molecules that are able to recruit eukaryotic ribosomes to the mRNA in a process which is known as cap-independent translation. IRESs are commonly located in the 5'-UTRs of RNA viruses. They facilitate translation of the viral RNAs in a cap-independent manner.

Examples of viral IRESs include Picornavirus IRES (Encephalomyocarditis virus, EMCV IRES), Aphthovirus IRES (Foot-and-mouth disease virus, FMDV IRES), Kaposi's sarcoma-associated herpes virus IRES, Hepatitis A IRES, Hepatitis C IRES, Pestivirus IRES, Cripavirus internal ribosome entry site (IRES), *Rhopalosiphum padi* virus internal ribosome entry site (IRES) and 5'-Leader IRES and intercistronic IRES in the 1.8-kb family of immediate early transcripts (IRES)1. The invention also encompasses non-natural derivatives of the above IRESs which retain the capacity to recruit eukaryotic ribosomes to the mRNA.

In some preferred embodiments, the IRES is an encephalomyocarditis virus (EMCV) IRES. In one embodiment of the invention, the nucleotide sequence of the EMCV IRES is as given in SEQ ID NO: 14 or a nucleotide sequence having at least 80%, more preferably at least 85%, 90% or 95% sequence identity thereto and which encodes an IRES.

In other embodiments, the IRES is a Foot-and-mouth disease virus (FMDV) IRES. In one embodiment of the invention, the nucleotide sequence of the FMDV IRES is as given in SEQ ID NO: 15 or a nucleotide sequence having at least 80%, more preferably at least 85%, 90% or 95% sequence identity thereto and which encodes an IRES.

The rep gene is operably-associated with the IRES. Preferably, the IRES is located downstream of the cap gene and upstream of the translation start site for Rep 78/68. In some embodiments, the IRES replaces the wild-type p5 promoter. A further advantage of the removal of the p5 promoter is that, in the wild-type virus, the p5 promoter is bound by and is activated by the E2A DNA-binding protein (DBP). Hence the removal of the p5 promoter means that the E2A gene is not required (e.g. in a Helper Plasmid) to produce virus particles.

In other embodiments, the Cap and Rep polypeptides are produced as fusion polypeptide. In this case, the stop codon at the end of the cap gene is replaced with one or more codons which encode linker amino acids, and it is ensured that the coding sequences of the cap and rep genes are in frame. A single polypeptide which comprises the amino acid sequences of both Cap and Rep polypeptides is therefore produced as a fusion polypeptide. If an appropriate cleavable amino acid linker sequence is used, then the fusion polypeptide may be cleaved into separate Cap and Rep polypeptides.

In other embodiments, the Cap and Rep polypeptides are produced by alternative splicing. In this case the cap gene(s) would contain a splice donor sequence upstream of the first cap gene ATG start codon but downstream of the promoter +1 position driving transcription of the cap gene(s). After the stop codon of the cap gene(s) a splice acceptor site would be added to allow splicing over the cap gene from the 5' donor splice site to the 3' acceptor splice site. After the splice acceptor site (i.e. downstream or 3'), the rep gene coding sequence(s) would be placed to allow expression from spliced mRNA transcripts. In the interest of clarity, in this model the cap gene(s) are placed within an intron that is spliced when rep gene expression is required.

Sequences known to mediate splicing are known to those in the art, and sequences would have to be selected based on their strength and propensity to induce splicing to ensure that an optimal level of cap gene(s) and rep genes were expressed to enable efficient viral particle production. Ensuring the optimal relative stoichiometry of the rep and cap mRNA encoding transcripts is therefore important.

In other embodiments, Cap and Rep polypeptides may be produced by encoding a 2A peptide between the main polypeptides. This 2A sequence could derive from porcine teschovirus-1 (P2A), *Thosea asigna* virus 2A (T2A), FMDV 2A (abbreviated herein as F2A) or equine rhinitis A virus (ERAV) 2A (E2A). When a polypeptide is produced that contains a 2A sequence, the polypeptide is cleaved into two polypeptides by the 2A sequence. As such, the two remaining proteins are at equal stoichiometries. This is undesirable in the case of AAV Rep and AAV Cap where excess expression of Cap is deemed to be advantageous. Therefore, although one embodiment of the invention may use a 2A sequence, it is not the preferred method.

The production of stable cell lines in mammalian culture typically requires a method of selection to promote the growth of cells containing any exogenously-added DNA. Preferably, one or more of the nucleic acid molecules of the invention additionally comprise a selection gene or an antibiotic resistance gene. To this end, a range of genes are known that provide resistance to specific compounds when the DNA encoding them is inserted into a mammalian cell genome. Preferably, the selection gene is puromycin N-acetyl-transferase (Puro), hygromycin phosphotransferase (Hygro), blasticidin s deaminase (Blast), Neomycin phosphotransferase (Neo), glutathione S-transferase (GS), zeocin resistance gene (Sh ble) or dihydrofolate reductase (DHFR). Each of these genes provides resistance to a small molecule known to be toxic to mammalian cells, or in the case of GS provides a method for cells to generate glutathione in the absence of glutathione in the growth media.

In a preferred embodiment of the invention, the resistance gene is Puro. This gene is particularly effective because many of the cell lines used in common tissue culture are not resistant to Puro; this cannot be said for Neo where many, particularly HEK 293 derivatives, are already Neo resistant due to previous genetic manipulations by researchers (e.g. HEK 293T cells). Puro selection also has the advantage of being toxic over a short time window (<72 hours), and hence it allows variables to be tested rapidly and cells that do not harbour the exogenous DNA to be inserted into the genome are rapidly removed from the culture systems. This cannot be said of some other selection methods such as Hygro, where toxicity is much slower onset.

The development of stable cell lines using selection genes (e.g. Puro) requires that the resistance gene must be expressed in the cells. This can be achieved through a variety of methods including, but not limited to, internal ribosome entry sites (IRES), 2A cleavage systems, alternative splicing, and dedicated promoters.

In a preferred embodiment of the invention, the selection gene will be expressed from a dedicated promoter. This promoter will preferably transcribe in human cells at lower levels than the dedicated promoters driving the rep or cap genes.

Each of the genes in the nucleic acid molecules which encode a polypeptide or RNA will preferably be operably-associated with one or more regulatory elements. This ensures that the polypeptide or RNA is expressed at the desired level and at the desired time. In this context, the term "regulatory elements" includes one or more of an enhancer, promoter, intron, polyA, insulator or terminator.

The genes used in the AAV plasmids or vectors disclosed herein are preferably separated by polyA signals and/or insulators in an effort to keep transcriptional read-through to other genes to a minimum.

While some advantages may be obtained by using copies of the same regulatory element (e.g. promoter sequence) with more than one polypeptide or RNA-encoding nucleotide sequence (in terms of their co-ordinated expression), in the context of this invention, it is highly desirable to use different regulatory elements with each polypeptide or RNA-encoding nucleotide sequence. In this way, the risk of homologous recombination between these regulatory elements is reduced.

In some embodiments, the nucleic acid molecule of the invention (or the vector or plasmid comprising it or cell) additionally comprises one or more genes encoding one or more Adenovirus E4 polypeptides. Preferably, the nucleic acid molecule (or the vector or plasmid comprising it or cell) additionally comprises an Adenovirus transcription unit which is required for AAV replication.

The promoter which is operably associated with the E4 gene(s) may be inducible, repressible or constitutive. In some preferred embodiments, the promoter which is operably associated with the E4 gene(s) is a minimal promoter which comprises one or more cumate operator sites.

Preferably, the promoter is activatable by the binding of the same CymR-TAD or reCymR-TAD which is capable of activating the promoter which is operably associated with the cap and rep genes. Most preferably, the promoter is the same promoter as that which is operably associated with the cap and rep genes.

The nucleic acid molecule of the invention will, most embodiments, be a plasmid or vector which is useful in the production of AAVs. In most embodiments, therefore, the nucleic acid molecule of the invention (or the vector or plasmid comprising it) will not comprise inverted terminal repeats (ITRs), except for the nucleic acid molecule comprising a transgene. In some embodiments, the nucleic acid molecule of the invention (or the vector or plasmid comprising it) will not comprise one or more genes selected from Adenovirus E1A, E1B, E4, E2a or VA.

In some preferred embodiments, the nucleic acid molecule of the invention (or the vector or plasmid or plasmid system or cell comprising it) does not comprise the Adenovirus E2A gene.

As used herein, the term "E2A" or "E2A gene" refers to a viral E2A gene or a variant or derivative thereof. Preferably, the E2A gene is from or derived from a human adenovirus, e.g. Ad5.

In one embodiment of the invention, the nucleotide sequence of the Adenovirus E2A gene is as given in SEQ ID NO: 16 or a nucleotide sequence having at least 80%, more preferably at least 85%, 90% or 95% sequence identity thereto and which encodes a DNA-binding protein which aids elongation of viral DNA replication.

In one embodiment of the invention, the nucleotide sequence for the AAV P5 promoter is absent.

In another embodiment, there is provided a plasmid or vector comprising a nucleic acid molecule of the invention.

Examples of preferred embodiments of the invention include nucleic acid molecules comprising the following elements in this order:

6×CuO+CMV minimal promoter-AAV2 cap gene-FMDV IRES-rep gene
6×CuO+p565 minimal promoter-AAV2 cap gene-EMCV IRES-rep gene
6×CuO+CMV minimal promoter-AAV2 cap gene-EMCV RES-rep gene Preferably, the term "rep gene" refers to a gene which encodes Rep78 and Rep68 polypeptides (but preferably does not encode functional Rep52 or Rep40 polypeptides).

In some embodiments, the invention involves a nucleic acid molecule comprising: (i) a promoter, operably associated with (ii) a gene encoding a CymR polypeptide. In this molecule, the promoter is preferably a constitutive promoter. In some embodiments, this nucleic acid molecule is integrated into the genome of a host cell or cell line.

In some embodiments, the invention involves a nucleic acid molecule, vector or plasmid comprising: (i) a promoter, operably associated with (ii) a gene encoding a CymR polypeptide. In this molecule, the promoter is preferably a constitutive promoter. This nucleic acid may be used to induce expression of Rep and Cap polypeptides from the CuO-cap-rep nucleic acid molecule of the invention. Preferably, this nucleic acid molecule is not integrated into the genome of a host cell or cell line.

In some embodiments, the invention involves a nucleic acid molecule, vector or plasmid comprising: (i) a promoter comprising one or more cumate operator sites, operably associated with (ii) a gene encoding a rc-CymR-TAD polypeptide. In this molecule, the promoter is preferably a minimal promoter (as defined herein). In some embodiments, this nucleic acid molecule is integrated into the genome of a host cell or cell line. The promoter preferably comprises 1, 2 or 3, most preferably only one CuO site.

The term "rc-CymR" refers to a reverse cumate-repressor protein. This is a mutant CymR polypeptide which binds CuO sites in the presence of cumate, but not in the absence of cumate. Such rcCymR mutants are known in the art. Compared to the wild-type CymR polypeptide sequence, one such mutant has the mutations Ala125Val, Glu142Gly and Met144Ile.

Preferably, the CymR and rcCymR polypeptides used in the context of the current invention have a deletion of the wild-type amino acids Met Val Ile at the N-terminal. The preferred CymR- and rcCymR-encoding nucleotide sequences also have corresponding deletions. Preferred examples of the CymR and rcCymR nucleotide and polypeptide sequences are given in SEQ ID NOs: 17-20.

The term "TAD" refers to a "transactivator domain". Transactivator domains act by recruiting elements of the pre-initiation complex, for example TFIID, to the TATA box.

TFIID is a composition of subunits including the TATA-binding protein (TBP) and TBP-associated factors (TAFs). TBP binding to the TATA-box is enough to initiate transcription in TATA-box containing promoters. Once TFIID is bound to the promoter, RNA polymerase II and the remainder of the pre-initiation complex is recruited, thus allowing initiation of transcription.

The TAD may therefore be a polypeptide or domain thereof which binds to at least one element of the transcription pre-initiation complex, e.g. to TFIID, to a TATA-binding protein (TBP) or to TBP-associated factor (TAF).

In the context of this invention, the minimal promoter contains the TATA-box and downstream promoter elements, but all upstream promoter elements and enhancer sequences have been removed. They are replaced with DNA-binding sites for a DNA-binding protein, i.e. CuO.

A transactivation domain (TAD) is a transcription factor scaffold which can bind either directly or indirectly with transcriptional co-activators (such as TAFs). By fusing these TADs to a DNA-binding protein (i.e. rcCymR), which itself is directed to the enhancer region (e.g. CuO) of a promoter by positioning of the DNA binding sites upstream of the TATA box, it is possible to target this transactivation activity to a promoter.

The transactivation domain (TAD) is preferably a polypeptide or domain or part thereof, e.g. a domain of a protein which has the desired activity. Examples of TADs include VP16 (and concatamers termed VP32, VP64), p53, rTa, p65 and combinations thereof. The TAD may comprise a plurality of TADs, which may be the same (e.g. VP16-VP16) or different. Preferably, the TAD is from VP16 or p53. Both of these domains directly contact key TAFs to recruit TFIID. These TADs are derived from VP16 or p53 proteins (i.e. they are part of the larger protein).

VP16 is a herpes simplex virus protein that normally induces immediate early gene transcription in the HSV. It can be multiplexed to form a stronger TAD.

p53 is a tumour suppressor protein which contains several domains for DNA binding, tetramerization, and transcriptional activation. The TAD domains (AD1 and AD2, which can be used separately or together) are found at the N-terminal of the p53 monomer.

The rcCymR-TAD may be fusion protein or the rcCymR and TAD may be joined by a linker (which may be an amino acid linker or non-amino acid linker, preferably an amino acid linker). They may also be joined, preferably at the C-terminus of the DNA targeting domain.

There are many established algorithms available to align two amino acid or nucleic acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid or nucleic acid sequences for comparison may be conducted, for example, by computer-implemented algorithms (e.g. GAP, BESTFIT, FASTA or TFASTA), or BLAST and BLAST 2.0 algorithms.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

In some embodiments, the BLASTP 2.5.0+ algorithm may be used (such as that available from the NCBI) using the default parameters.

In other embodiments, a BLAST Global Alignment program may be used (such as that available from the NCBI) using a Needleman-Wunsch alignment of two protein sequences with the gap costs: Existence 11 and Extension 1.

One method for the production of recombinant AAVs is based on the transfection of some or all elements that are required for AAV production into host cells, such as HEK293 cells, or engineered packaging cell lines as described elsewhere.

For HEK293 host cells, this generally involves co-transfection with 3 vectors or plasmids:
- (a) an AAV ITR-containing plasmid, carrying the gene (i.e. transgene) of interest;
- (b) a plasmid that carries the AAV rep-cap genes; and
- (c) a plasmid that provides the necessary helper genes isolated from adenovirus.

The invention therefore provides a kit comprising:
(A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order, wherein the cap gene and the rep gene are both operably associated with the promoter;
and optionally one of more of the following:
(B) a nucleic acid molecule, vector or plasmid comprising:
  (i) a promoter (preferably a minimal promoter) comprising one or more cumate operator sites, operably associated with
  (ii) a gene encoding a rc-CymR-TAD polypeptide;
(C) a nucleic acid molecule, vector or plasmid comprising
  (i) a promoter (preferably a constitutive promoter), operably associated with
  (ii) a gene encoding a CymR;
(D) a nucleic acid molecule, vector or plasmid comprising:
  (i) a promoter (preferably a constitutive promoter), operably associated with
  (ii) a gene encoding a CymR-TAD polypeptide;
(E) a nucleic acid molecule, vector or plasmid comprising:
  (i) one or more promoters, which may or may not comprise one or more cumate operator sites, operably associated with
  (ii) one or more adenoviral genes which are competent to support AAV production, preferably E4 and/or VAI-RNA;
(F) a nucleic acid molecule, vector or plasmid comprising:
  (i) a promoter, operably associated with
  (ii) a transgene,
wherein the promoter and transgene are flanked by ITRs.

The nucleic acid molecules may, for example, be plasmids or vectors.

In some embodiments, the kit comprises nucleic acid molecules (A), (D) and (F). In other embodiments, the kit comprises nucleic acid molecules (A), (B), (C) and (F). Nucleic acid molecule (E) may optionally be added to the above embodiments.

The kit may also comprise cumate.

In some embodiments, the selected nucleic acid molecules are present on the same vector or plasmid. This therefore reduces the number of separate vectors or plasmids to be used in the transfection process. Preferably, nucleic acid molecules (D) and (F) are present on the same nucleic acid molecule.

The kit may also additionally comprise a Helper Plasmid comprising one or more viral genes selected from adenovirus E1A, E1B, E4 and VA.

In some embodiments of the invention, the Helper Plasmid comprises an E2A gene. In other embodiments, the Helper Plasmid does not comprise an E2A gene. In the latter case, the omission of the E2A gene reduces considerably the amount of DNA which is needed in the Helper Plasmid.

The kit may also additionally comprise a mammalian host cell (e.g. HEK293), optionally comprising one or more viral genes selected from E1A, E1B, E4 and VA expressible from the host cell genome. In some embodiments of the invention, the mammalian host cell additionally comprises an E2A gene expressible from the host cell genome. In other embodiments, the mammalian host cell does not comprise an E2A gene.

In some embodiments, one or more of the nucleic acids may be delivered to the cell or cell lines using an Adenoviral vector. This will encode Adenoviral genes but may also encode the CymR-TAD and/or transgene. This may have advantages due to the efficiency of gene delivery to AAV-producing cells that can be achieved by an Adenoviral vector.

The kit may also contain reagents and/or materials for purification of the AAV particles such as those involved in the density banding and purification of viral particles, e.g. one or more of centrifuge tubes, Iodixanol, dialysis buffers and dialysis cassettes.

In another embodiment, the invention provides a cell line, comprising:
(A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order, wherein the cap gene and the rep gene are both operably associated with the promoter;
and optionally one of more of the following:
(B) a nucleic acid molecule, vector or plasmid comprising:
  (i) a promoter (preferably a minimal promoter) comprising one or more cumate operator sites, operably associated with
  (ii) a gene encoding a rc-CymR-TAD polypeptide;
(C) a nucleic acid molecule, vector or plasmid comprising:
  (i) a promoter (preferably a constitutive promoter), operably associated with
  (ii) a gene encoding a CymR;
(D) a nucleic acid molecule, vector or plasmid comprising:
  (i) a promoter (preferably a constitutive promoter), operably associated with
  (ii) a gene encoding a CymR-TAD polypeptide;
(E) a nucleic acid molecule, vector or plasmid comprising:
  (i) one or more promoters, which may or may not comprise one or more cumate operator sites, operably associated with
  (ii) one or more adenoviral genes which are competent to support AAV production, preferably E4 and/or VAI-RNA;
(F) a nucleic acid molecule, vector or plasmid comprising:
  (i) a promoter, operably associated with
  (ii) a transgene,
  wherein the promoter and transgene are flanked by ITRs.

The nucleic acid molecules may, for example, be plasmids or vectors.

In some embodiments, the cell line is a packaging cell line. In other embodiments, the cell line is a producer cell line.

In some preferred embodiments, the packaging cells comprise nucleic acid molecules, vectors or plasmids (A) and (E). In other preferred embodiments, the packaging cells comprise nucleic acid molecules, vectors or plasmids (A), (B), (C) and (E). In other preferred embodiments, the producer cells comprise nucleic acid molecules, vectors or plasmids (A), (B), (C), (E) and (F).

In some preferred embodiments, each of (A), (B), (C), (E), and (F), when present, are integrated into the genome of the cell line, wherein the specified genes are expressed or expressible therefrom.

The cells may be isolated cells, e.g. they are not situated in a living animal or mammal. Examples of mammalian cells include those from any organ or tissue from humans, mice, rats, hamsters, monkeys, rabbits, donkeys, horses, sheep, cows and apes. Preferably, the cells are human cells. The cells may be primary or immortalised cells.

Preferred cells include HEK-293 or a derivative thereof (e.g. HEK 293T, HEK-293E, HEK-293 FT, HEK-293S, HEK-293SG, HEK-293 FTM, HEK-293SGGD, HEK-293A), MDCK, C127, A549, HeLa, CHO, mouse myeloma, PerC6, 911 and Vero cell lines. HEK-293 cells have been modified to contain the E1A and E1B proteins and this obviates the need for these proteins to be supplied on a Helper Plasmid. Similarly, PerC6 and 911 cells contain a similar modification and can also be used. Most preferably, the human cells are HEK293, HEK293T, HEK293A, PerC6 or 911. Other preferred cells include CHO and VERO cells.

Preferably, the cells of the invention are capable of inducibly-expressing the rep and cap genes and/or inducibly-expressing the rcCymR-TAD.

In some preferred embodiments, the cells of the cell line are present in a suspension. This has major advantages in the development of scalable and regulatory-accepted manufacturing processes, due to compatibility with stirred-tank and wave bioreactors, and through facilitating absence of animal components required for growth (e.g. FBS).

The nucleic acid molecules, plasmids and vectors of the invention may be made by any suitable technique. Recombinant methods for the production of the nucleic acid molecules and packaging cells of the invention are well known in the art (e.g. "Molecular Cloning: A Laboratory Manual" (Fourth Edition), Green, M R and Sambrook, J., (updated 2014)).

The expression of the rep and cap genes from the nucleic acid molecules of the invention may be assayed in any suitable assay, e.g. by assaying for the number of genome copies per ml by qPCR (as described the Examples herein).

In a further embodiment, there is provided a process for producing an AAV cell line, the process comprising the steps of integrating into the genome of the cells of the cell line:
(A) a nucleic acid molecule, vector or plasmid comprising:
  (i) a promoter comprising one or more cumate operator sites,
  (ii) a cap gene, and
  (iii) a rep gene, wherein the rep gene preferably encodes Rep78 and Rep68, in the above 5'-3' order, wherein the cap gene and the rep gene are both operably associated with the promoter, thereby producing a cell that inducibly expresses viral cap and rep genes;
and optionally one of more of the following:
(B) a nucleic acid molecule, vector or plasmid comprising:
  (i) a promoter (preferably a minimal promoter) comprising one or more cumate operator sites, operably associated with
  (ii) a gene encoding a rc-CymR-TAD polypeptide;
(C) a nucleic acid molecule, vector or plasmid comprising:
  (i) a promoter (preferably a constitutive promoter), operably associated with
  (ii) a gene encoding CymR;

(E) a nucleic acid molecule, vector or plasmid comprising:
(i) one or more promoters, which may or may not comprise one or more cumate operator sites, operably associated with
(ii) one or more adenoviral genes which are competent to support AAV production, preferably E4 and/or VAI-RNA.

The nucleic acid molecules may, for example, be plasmids or vectors.

In some preferred embodiments, the cells comprise nucleic acid molecule, vector or plasmid (A) and optionally nucleic acid, vector or plasmid (E). In these embodiments, the expression of the cap and rep genes and optionally adenoviral genes may be induced in the cell by the presence, in the cell (e.g. by transient transfection), of a CymR-TAD polypeptide. This binds to the cumate operator site(s), thus promoting transcription of the cap and rep genes.

In other preferred embodiments, the cells comprise nucleic acid molecules, vectors or plasmids (A), (B), (C) and optionally nucleic acid, vector or plasmid (E). The expression of the cap and rep genes may be induced in the cell by the presence, in the cell, of cumate. This binds to the rcCymR-TAD, thus promoting transcription of the cap and rep genes. Cumate also binds to the CymR, thus preventing CymR from repressing transcription of the cap and rep genes.

Preferably, the AAVs are subsequently harvested and/or purified.

Each of the above nucleic acids, vectors and plasmids may be introduced into the cell. As used herein, the term "introducing" one or more nucleic acids, plasmids or vectors into the cell includes transformation, and any form of electroporation, conjugation, infection, transduction or transfection, inter alia. Processes for such introduction are well known in the art (e.g. Proc. Natl. Acad. Sci. USA. 1995 Aug. 1; 92 (16):7297-301).

The transgene is flanked by inverted terminal repeats (ITRs). In some preferred embodiments, the transgene encodes a CRISPR enzyme (e.g. Cas9, Cpf1) or a CRISPR sgRNA.

The invention also provides a method of inducing transcription of cap and rep genes in a cell, the method comprising the steps:
inducing the transcription of cap and rep genes in a cell which comprises in its genome:
(A) a nucleic acid molecule, vector or plasmid comprising:
(i) a promoter comprising one or more cumate operator sites,
(ii) a cap gene, and
(iii) a rep gene, wherein the rep gene preferably encodes Rep78 and Rep68, in the above 5'-3' order, wherein the cap gene and the rep gene are both operably associated with the promoter,
wherein the inducing is by the presence, in the cell, of a CymR-TAD polypeptide.

The transcription of the cap and rep genes is induced in the cell by the presence, in the cell, of a CymR-TAD polypeptide. This binds to the cumate operator site(s), thus promoting transcription of the cap and rep genes. The CymR-TAD may be introduced into the cell as a polypeptide. Preferably, however, the CymR-TAD is expressed in the cell, e.g. on a plasmid or vector (which may itself be introduced into the cell at a desired time). The CymR-TAD may be transiently expressed in the cell.

Preferably, the cell line is a packaging cell line or a producer cell line.

In some embodiments, the method additionally comprises the step of introducing:
(C) a nucleic acid molecule, vector or plasmid comprising:
(i) a promoter (preferably a constitutive promoter), operably associated with
(ii) a nucleotide sequence encoding a CymR-TAD;
and/or
(D) a nucleic acid molecule, vector or plasmid comprising:
(i) one or more promoters, which may or may not comprise one or more cumate operator sites, operably associated with
(ii) one or more adenoviral genes which are competent to support AAV production, preferably E4 and/or VAI-RNA;
and/or
(E) a nucleic acid molecule, vector or plasmid comprising:
(i) a promoter, operably associated with
(ii) a transgene,
wherein the promoter and transgene are flanked by ITRs, into the cell.

The presence of CymR-TAD in the cell induces expression of the cap and rep genes.

Nucleic acid molecules (C), (D) and (E) may be in the form of a plasmid or vector. In some embodiments, nucleic acid molecules (C) and (E) are on the same vector or plasmid. This therefore avoids the need for two separate transfection steps.

The invention also provides a method of inducing transcription of cap and rep genes in a cell, the method comprising the steps:
inducing the transcription of cap and rep genes in a cell which comprises in its genome:
(A) a nucleic acid molecule, vector or plasmid comprising:
(i) a promoter comprising one or more cumate operator sites,
(ii) a cap gene, and
(iii) a rep gene, wherein the rep gene preferably encodes Rep78 and Rep68, in the above 5'-3' order, wherein the cap gene and the rep gene are both operably associated with the promoter;
(B) a nucleic acid molecule, vector or plasmid comprising:
(i) a promoter comprising one or more cumate operator sites, operably associated with
(ii) a gene encoding a rc-CymR-TAD polypeptide;
(C) a nucleic acid molecule, vector or plasmid comprising:
(i) a promoter, operably associated with
(ii) a gene encoding CymR;
and optionally
(D) a nucleic acid molecule, vector or plasmid comprising:
(i) one or more promoters, which may or may not comprise one or more cumate operator sites, operably associated with
(ii) one or more adenoviral genes which are competent to support AAV production, preferably E4 and/or VAI-RNA;

and/or (E) a nucleic acid molecule, vector or plasmid comprising:
   (i) a promoter, operably associated with
   (ii) a transgene,
   wherein the promoter and transgene are flanked by ITRs,
wherein (A), (B), (C), (D) and (E), when present, are preferably all integrated into the genome of the cell, wherein the inducing is by the presence, in the cell, of cumate.

The expression of the cap and rep genes may be induced in the cell by the presence, in the cell, of cumate. In absence of cumate, the CymR binds to the promoter region of the rcCymR and represses transcription, and also binds to the minimal promoters driving the rep-cap (and/or Adenoviral) genes sterically blocking binding of residual rcCymR-TAD. In the presence of cumate, the repression of rcCymR-TAD transcription is relieved, as is the steric blocking, and the rcCymR-TAD is allowed to bind to the promoter of the cap-rep gene (and/or Adenoviral genes), and activates transcription—resulting in rAAV production. Cumate may be introduced into the cell by introducing cumate into the media surrounding the cell, at the desired time.

Preferably, the cell is a producer cell line.

The disclosure of each reference set forth herein is specifically incorporated herein by reference in its entirety.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: CMV Promoter Comprising CuO Site

Plasmid Design

A CMV promoter containing a CuO site was designed. Two variants were created: the first had one CuO site; the second had a second CuO site downstream of the +1 site to increase steric blocking effects on transcription. The variants are shown in FIGS. 3A and 3B.

Figures 3A, 3B:
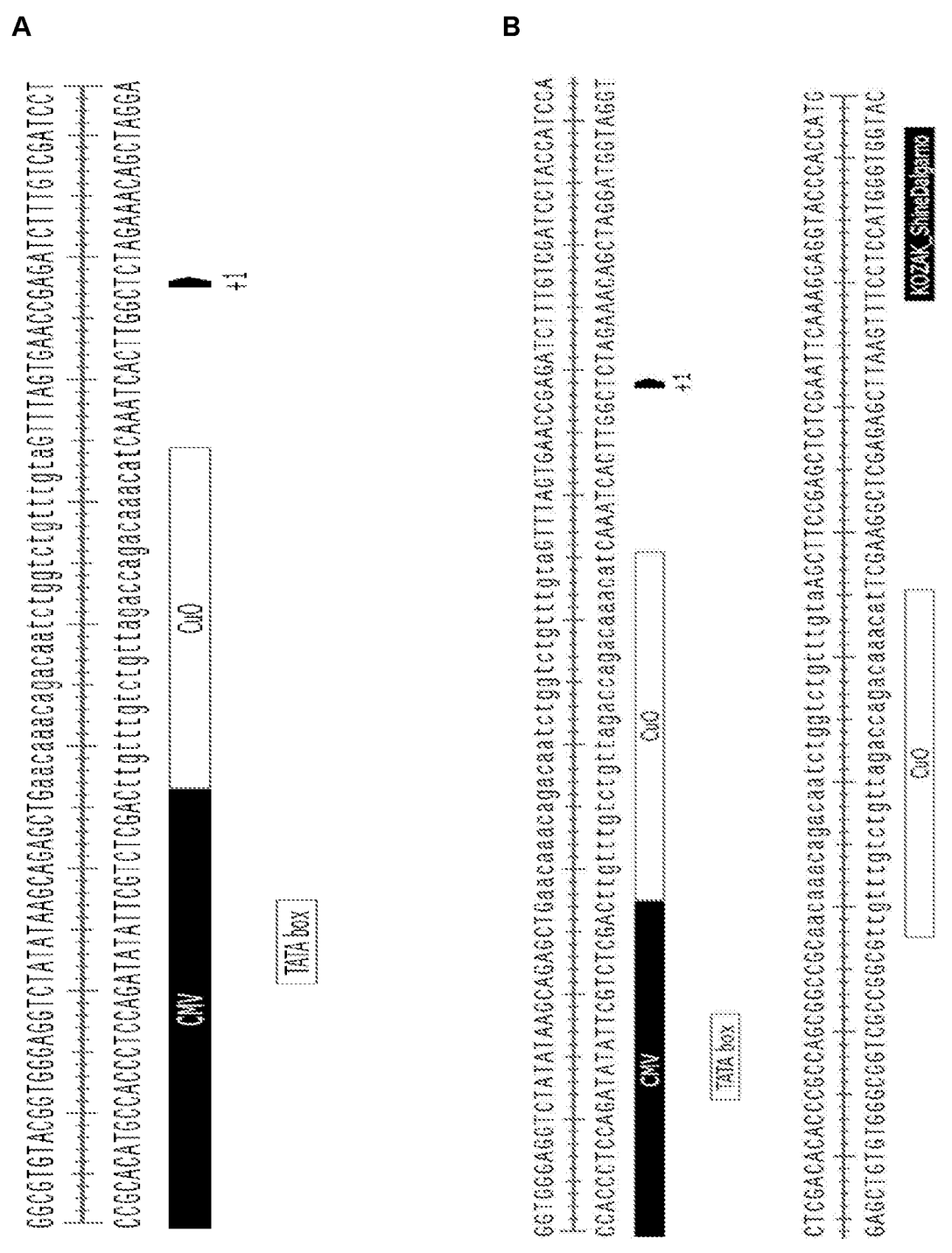

The CMV-CuO promoter was cloned into Q414 (pSF-CMV-EGFP), resulting in Q5422 (pSF-CMV_CuO-EGFP), with CuO in the position shown in FIG. 3A. A second CuO site was cloned into Q5422 resulting in Q5424 (pSF-CMV_CuOx2-EGFP), with the promoter and 5'UTR as shown in FIG. 3B.

The gene encoding the Cumate repressor protein (CymR—accession number: AB042509.1) was synthesized and cloned into OG10 (pSF-CMV-kan), resulting in Q4721 (pSF-CMV-CymR).

Each of the above EGFP plasmids were analyzed by transfection in a 96-well plate format, with and without Q4721, and with and without cumate (30 μg/mL in 95% EtOH).

Where Q4721 was omitted, OG10 was used as stuffer DNA. Where cumate was omitted, 95% EtOH was added.

Transfection Setup

Six DNA mixes were prepared as per Table 2. Transient transfections were carried out using a standard protocol for PEI transfection of Adherent cell lines, in HEK293 cells. DNA:PEI ratio 1:2.5 was used, with 0.14 μg total DNA transfected per well of 96 well plate. Plasmids were added in equimolar ratios, with each mix tested in triplicate.

For the cumate solution, a stock solution of 5 mg/mL was prepared by dissolving cumate (Sigma, 268402) in 95% EtOH (Honeywell, 24103). 3 μL of either cumate stock solution or 95% EtOH was added to 197 μL DMEM+10% FBS. Prior to addition of DNA:PEI complexes to cells, 5 μL of either cumate-DMEM or EtOH-DMEM was added to each well (final cumate concentration of 30 μg/mL).

48 hours post-transfection, cells were prepared for flow cytometry analysis using the Attune NxT Flow Cytometer.

TABLE 2

| DNA mixes for transfections | | |
|---|---|---|
| DNA mix | EGFP plasmid | Other |
| 1 - CMV-CuO + CymR | Q5422 | Q4721 |
| 2 - CMV-CuO − CymR | Q5422 | OG10 |
| 3 - CMV-CuOx2 + CymR | Q5424 | Q4721 |
| 4 - CMV-CuOx2 − CymR | Q5424 | OG10 |
| 5 - CMV + CymR | Q414 | Q4721 |
| 6 - CMV − CymR | Q414 | OG10 |

Results

Figure 4:
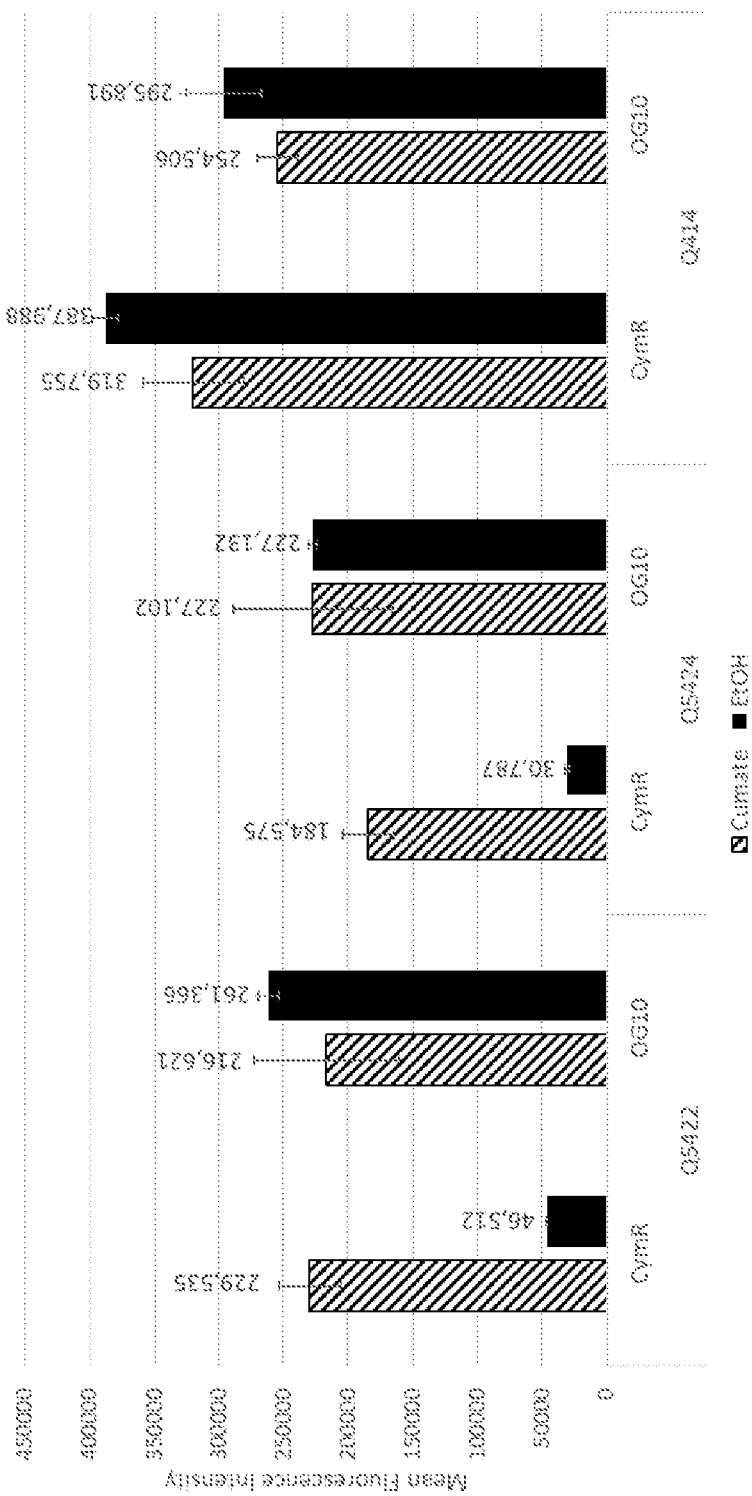
FIG. 4. Mean fluorescence intensity of HEK293 cells transfected with CymR and cumate regulated eGFP constructs. Error bars depict standard deviation (n=3, biological triplicate, analytical single).

FIG. 4 shows the Mean fluorescence Intensity of cells after 48 hours. Each biological triplicate was analyzed as a singlet, with 10,000 events counted from the live cell population. An EGFP negative sample was used to gate around non-fluorescent cells. The highest expression levels were observed for the constitutively-active CMV in Q414. The addition of cumate in these samples had a small impact on expression.

For Q5422, with one CuO in the CMV promoter, repression was observed where CymR was present without cumate. Compared to Q5422+OG10+EtOH, this was calculated to be 5.6-fold repression (17.7% of the constitutive equivalent). The induction when CymR was present with cumate was equivalent to the constitutive control.

As mirrored in the visual inspection of cells, Q5424 showed better repression than Q5422 (13.5% expression compared to the constitutive equivalent, 7.3-fold repression). The induction was lower, with 81% of the constitutive equivalent rather than the comparable expression seen with Q5422.

Internal target specifications for the inducible system were set whereby repression should be <5% of the constitutive, and induction >75% of the constitutive. Neither Q5422 nor Q5424 appeared to yield sufficient repression when CymR was present without cumate to meet these criteria. They do both, however, show sufficient induction when cumate is added. Without CymR present, both CuO containing promoters showed constitutive activity. This meant that the system relied on constitutive and sufficient expression of CymR such that the inducible promoter remained off until cumate was added.

Example 2: CymR-Transactivators

To resolve the issue of background expression of toxic proteins, a minimal promoter was designed which was basally inactive unless activated in some way. This minimal promoter can also be used with DNA-binding proteins fused to transcriptional activator domains (TADs, transactivators).

Plasmid Design

CymR-TAD fusion proteins were designed starting from Q4721 (pSF-CMV-CymR), the stop codon for CymR was removed and an oligo duplex of the TAD was cloned in-frame, with a new stop codon. To test additional TADs, several constructs were designed wherein TAD multimers were used. The resulting plasmids are listed in the table below. 'GS' in this instance refers to a glycine-serine linker motif.

TABLE

CymR-TAD plasmids generated

| Plasmid Identification | Plasmid Name |
| --- | --- |
| Q5622 | CymR_VP16 |
| Q5624 | CymR_p53 |
| Q5813 | CymR_p53_VP16 |
| Q5814 | CymR_p53_p53 |
| Q5866 | CymR_VP16_GS |

The CuO-based minimal promoter used was with six CuO sites placed with small spacers upstream of the TATA box of the minimal CMV. This promoter was cloned upstream of an EGFP, resulting in Q5868 (pSF-6xCuO_minCMV-EGFP).

This experiment was setup with positive promoter control conferred by Q414 (pSF-CMV-EGFP) and negative promoter control provided by Q437 (pSF-minCMV-EGFP). CymR-only plasmid Q4721 was not included, but a stuffer DNA control was included. This is because the key parameters are the promoter activity in the absence of any inducer (inducible EGFP+stuffer DNA) and the promoter activity in the presence of an inducer (inducible EGFP+CymR-TAD). Furthermore, the positive promoter control Q414 was not tested in combination with each CymR-TAD. It was anticipated that it would perform similarly with each.

Transfection Setup

Thirteen DNA mixes were prepared as per the table below. Transient transfections were carried out using a standard protocol for PEI transfection of Adherent cell lines, in HEK293 cells. DNA:PEI ratio 1:2.5 was used, with 0.14 µg total DNA transfected per well of 96 well plate. Plasmids were added in equimolar ratios, with each mix tested in triplicate. 48 hours post-transfection cells were prepared for flow cytometry analysis using the Attune NxT Flow Cytometer.

TABLE

DNA mixes for transfections

| DNA mix | EGFP plasmid | Other |
| --- | --- | --- |
| 1 - 6xCuO_minCMV-EGFP + CymR-VP16 | Q5868 | Q5622 |
| 2 - 6xCuO_minCMV-EGFP + CymR-p53 | Q5868 | Q5624 |
| 3 - 6xCuO_minCMV-EGFP + CymR-p53-VP16 | Q5868 | Q5813 |
| 4 - 6xCuO_minCMV-EGFP + CymR-p53x2 | Q5868 | Q5814 |
| 5 - 6xCuO_minCMV-EGFP + CymR-VP16_GS | Q5868 | Q5866 |
| 6 - 6xCuO_minCMV-EGFP + OG10 | Q5868 | OG10 |
| 7 - minCMV-EGFP + CymR-VP16 | Q437 | Q5622 |
| 8 - minCMV-EGFP + CymR-p53 | Q437 | Q5624 |
| 9 - minCMV-EGFP + CymR-p53-VP16 | Q437 | Q5813 |
| 10 - minCMV-EGFP + CymR-p53x2 | Q437 | Q5814 |
| 11 - minCMV-EGFP + CymR-VP16_GS | Q437 | Q5866 |
| 12 - minCMV-EGFP + OG10 | Q437 | OG10 |
| 13 - CMV-EGFP + OG10 | Q414 | OG10 |

Results

Figure 5:
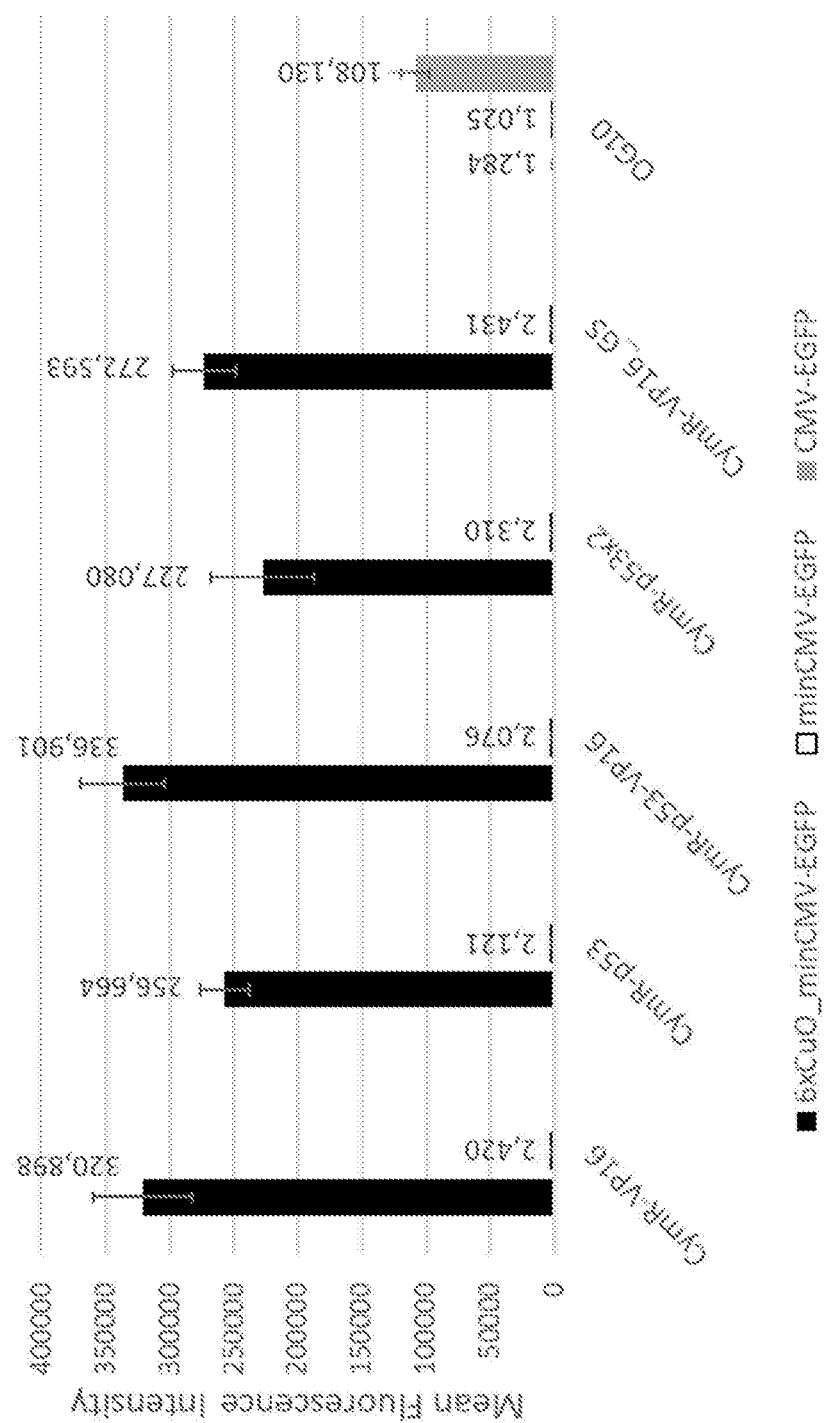
FIG. 5. Mean fluorescence intensity of HEK 293 cells. Error bars depict standard deviation (n=3, biological triplicate, analytical single). X-axis depicts the additional plasmid added (CymR-TAD or stuffer OG10).

FIG. 5 shows the mean fluorescence intensity as measured by flow cytometry. The first observation was that when there was a CymR-TAD present with the inducible EGFP plasmid, fluorescence was higher than with the positive promoter control (CMV-EGFP). This was unexpected; however, this was observed with CymR-TADs in subsequent experiments.

As expected, the negative promoter control (minCMV) showed very low basal activity. In this instance between 0.95% and 2.25% activation compared to the positive control (CMV). Comparatively low basal expression was seen with 6xCuO_minCMV-EGFP in the absence of induction: at 1.19% of the constitutive. This confirms that the promoter is transcriptionally inactive without inducers present and behaves as the negative control minCMV.

As all the CymR-TAs induced beyond the level of the constitutive control, it was concluded that all surpassed the 75% activation threshold. Additionally, conclusions were drawn about the relative transcriptional activation strength of each TAD or TAD-multimer. This data showed that the presence of VP16 conferred the highest activation, and the addition of a p53 TAD to the VP16 TAD gave no additional transcriptional activation activity. Similarly, the presence of a glycine-serine linker did not hinder the transcriptional activity of VP16. This meant that VP16 domains can be linked with linkers with minimal impact on function. On the other hand, p53 TAD did not appear to activate transcription as strongly as VP16. Two p53 TADs concurrently did not improve the activity.

Figure 6:
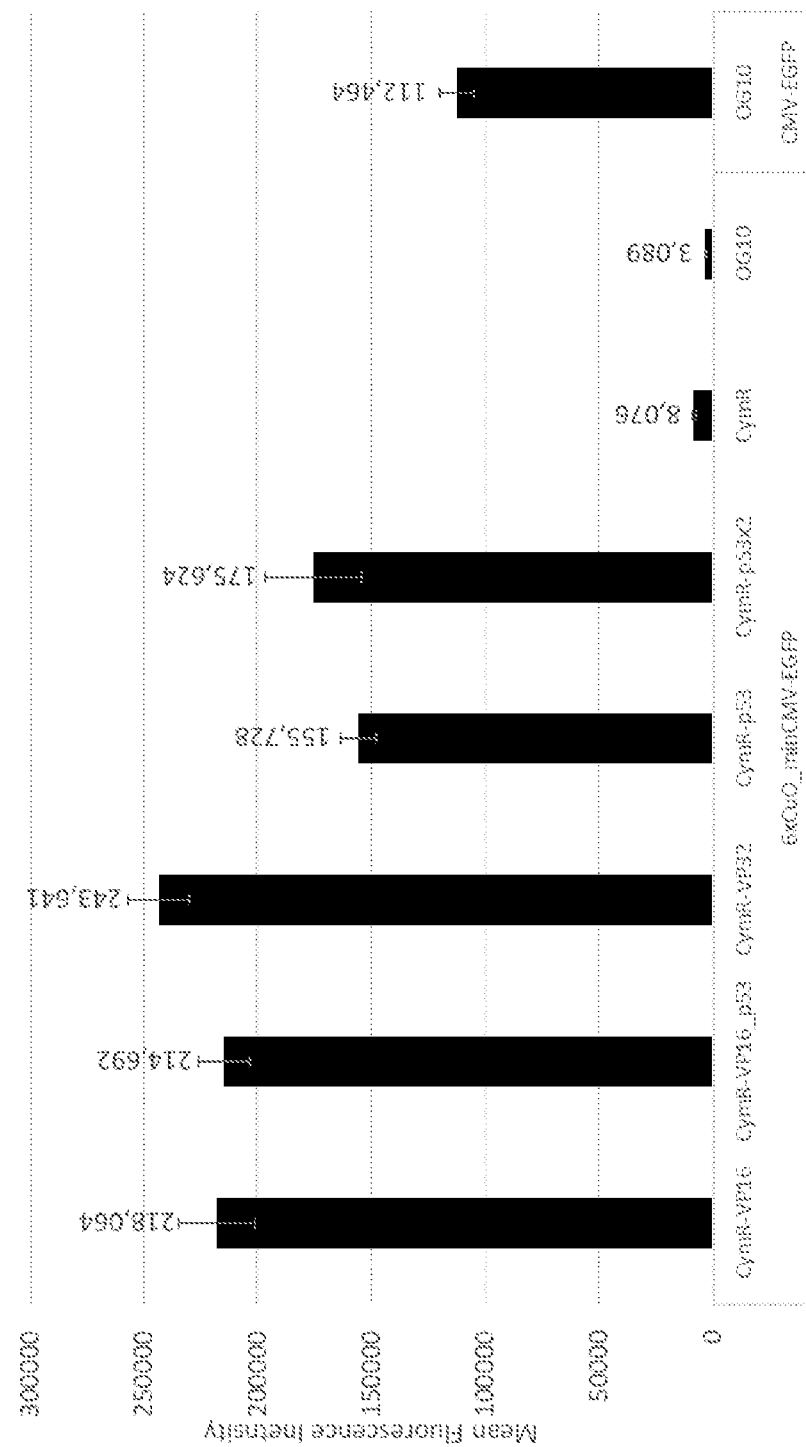
FIG. 6. Mean fluorescence intensity of HEK 293 cells in additional experiment. Error bars depict standard deviation (n=3, biological triplicate, analytical single). X-axis depicts the additional plasmid added (CymR-TAD or stuffer OG10).

In an identically set up experiment, a further set of TADs were compared, shown in FIG. 6. Experiment setup was identical as described in this Example, with the exception that the negative promoter minCMV control was not run in parallel—it was assumed that expression from this promoter would be negligibly low (as in FIG. 5). FIG. 6 shows again how the CymR-TADs allowed EGFP expression to exceed that driven by the constitutive CMV promoter and allowed comparison of two previously-uncharacterized TADs: VP16_p53 and VP32 (VP16-VP16). VP32 appeared to be the strongest TAD in this data, with p53 alone performing most weakly.

As previously observed, this data showed <5% expression from the uninduced inducible promoter (2.75% from 6xCuO_minCMV-EGFP+OG10 compared to the constitutive CMV-EGFP+OG10). Additionally, there was over 100% activation upon induction when compared to the constitutive.

Example 3: Further CymR-Transactivators

After initial testing of CymR-TADs using the simple EGFP expression experiment, the system was tested in the context of rAAV production. The CMV promoter in Q5220 (pSF-CMV-Cap5-EMCV-Rep) was replaced with the inducible 6xCuO_minCMV promoter resulting in Q5875 (pSF-6xCuO_minCMV-Cap5-EMCV-Rep).

Virus production was carried out using either the inducible packaging plasmid Q5875 or constitutive Q5220, standard helper plasmid Q1364 and standard EGFP transgene Q4346. In each instance, the CymR-TAD was delivered as for the EGFP experiment in Example 3: in the first rAAV experiment, only CymR-VP16 was tested, but in a subsequent experiment three other CymR-TADs were evaluated in their ability to induce viral production using the inducible promoter.

Transfection Setup

Five mixes of DNA were prepared for the first experiment, and seven for the second, as per the table below. Transient transfections were carried out with plasmids added in equimolar ratios. For each distinct DNA mix, three wells of a 6-well plate of adherent HEK293s were transfected. A total DNA mass of 2.5 µg was transfected per well. 72 hours post-transfection, the contents of each well was harvested using chemical lysis and crude AAV lysate obtained.

TABLE

DNA mixes for transfections

| Expt | DNA mix | Transgene Plasmid | Packaging Plasmid | Helper Plasmid | Other |
|---|---|---|---|---|---|
| 1 | 1 - Inducible RepCap + CymR-VP16 | Q4346 | Q5875 | Q1364 | Q5622 |
|   | 2 - Inducible RepCap | Q4346 | Q5875 | Q1364 | OG10 |
|   | 3 - Constitutive RepCap + CymR-VP16 | Q4346 | Q5220 | Q1364 | Q5622 |
|   | 4 - Constitutive RepCap | Q4346 | Q5220 | Q1364 | OG10 |
|   | 5 - RepCap5 production control | Q4346 | Q4658 | Q1364 | N/A |
| 2 | 1 - Inducible RepCap + CymR-VP16-p53 | Q4346 | Q5875 | Q1364 | Q5974 |
|   | 2 - Inducible RepCap + CymR-VP32 | Q4346 | Q5875 | Q1364 | Q5973 |
|   | 3 - Inducible RepCap + CymR-p53 | Q4346 | Q5875 | Q1364 | Q5624 |
|   | 4 - Inducible RepCap + CymR | Q4346 | Q5875 | Q1364 | Q4721 |
|   | 5 - Inducible RepCap | Q4346 | Q5875 | Q1364 | OG10 |
|   | 6 - Constitutive RepCap | Q4346 | Q5220 | Q1364 | OG10 |
|   | 7 - RepCap5 production control | Q4346 | Q4658 | Q1364 | N/A |

Results

Crude AAV samples were analyzed for titre values by qPCR, to ascertain if virus production could be controlled using the 6×CuO_minCMV promoter driving the RepCap cassette and with addition or absence of a CymR-TAD. The primers for qPCR targeted the UTR of the transgene plasmid, with plasmid Q4346 used as the standard in the assay. Vector genomes were calculated from qPCR data using standard approaches.

Figure 7:
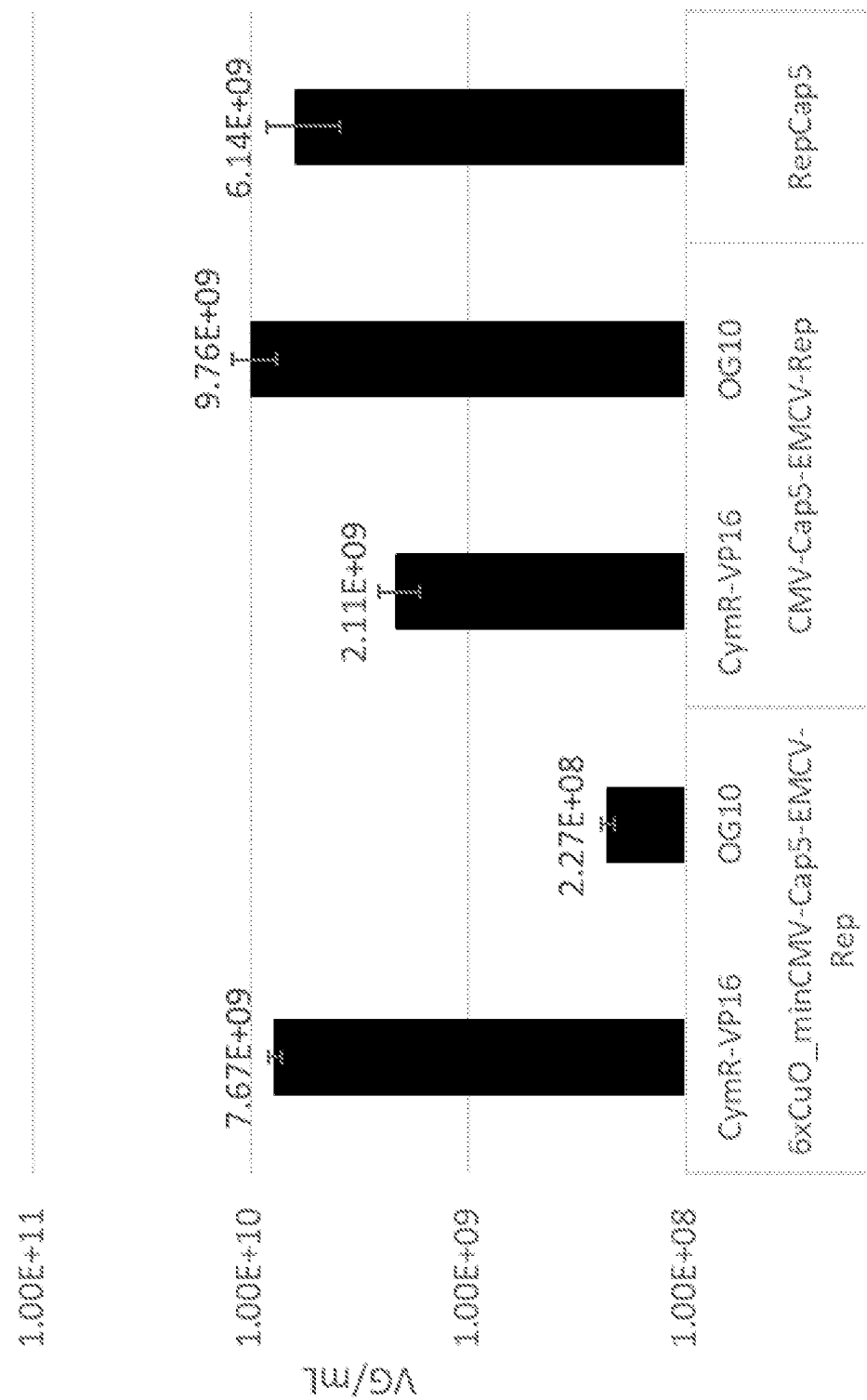
FIG. 7. qPCR data showing rAAV5 vector genomes per mL from the first rAAV production experiment. Error bars depict standard deviation, with n=3 (biological triplicate, analytical single).

FIG. 7 shows the viral genomes per mL from the first experiment. With no added activator, there was 2.35% activation compare to the constitutive equivalent packaging plasmid. This fell below the 5% threshold set, mirroring the data from the EGFP experiments. When activated (CymR-VP16 present), there was 78.5% viral production compared to the constitutive (if taking the constitutive+OG10). If comparing to the constitutive equivalent (+CymR-VP16) the viral production was over 100%. This would be consistent with the observations in the EGFP experiment also. In both scenarios however, observed promoter activation was over the target 75% threshold.

Figure 8:
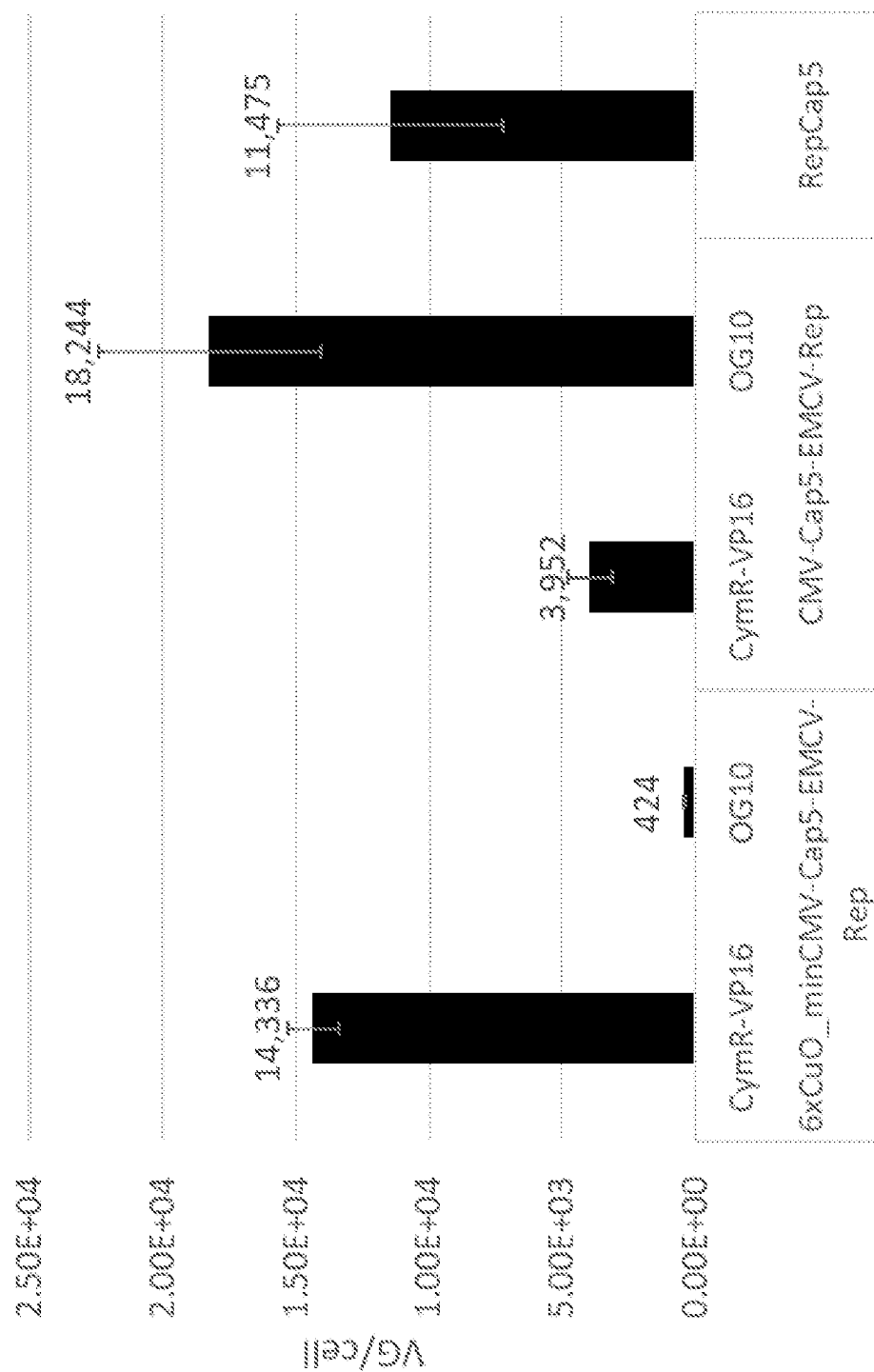
FIG. 8. Cell specific productivity from first rAAV production experiment, calculated using cell count at time of transfection, and viral genomes per mL. Error bars depict standard deviation, with n=3 (biological triplicate, analytical single).

FIG. 8 shows the viral genomes per cell, or cell specific productivity. For a viable packaging cell line, the ideal cell specific productivity (for an induced cell line) is >25,000 VG/cell, with <10,000 being the bottom cut-off. None of the samples in this experiment met the ideal 25,000 viral genomes per cell; however, the induced system was over the 10,000 VG/cell.

Example 4: rcCymR-Transactivators

In order to avoid using a DNA-based method of induction in a fully stable producer cell line, we investigated the use of a CymR mutant, rc-CymR, which can bind DNA only in the presence of cumate. By employing the same TAD-domain based transcriptional activation method, it may be possible to use a cumate-activated rc-CymR-TAD to regulate rAAV production.

The system would be used as follows: all AAV DNA genetic elements (inducible Rep and Cap genes, Ad5 helper genes, ITR-flanked transgene) would be stably integrated into the cell line, along with a constitutively expressed rc-CymR-TA. The rc-CymR-TAD protein would be unable to bind DNA unless cumate was present, preventing the TAD-mediated transcriptional activation. To induce rAAV production, cumate can be added, allowing the rc-CymR-TAD to bind the inducible promoters and initiate transcription of the AAV packaging genes and thus allowing viral production.

Plasmid Design

Three point mutations were introduced at amino acid positions A122V, E139G and M141I within the CymR sequence. This resulted in plasmid Q5812 (pSF-CMV-rc-CymR). From this, p53 and VP16 TADs were fused, resulting in Q5873 (pSF-CMV-rc-CymR-p53) and Q5874 (pSF-CMV-rc-CymR-VP16).

These plasmids were first tested with the inducible EGFP plasmid Q5868 (pSF-6×CuO_minCMV-EGFP) to assess whether or not the functionality with relation to cumate had changed.

Transfection Setup

Nine DNA mixes were prepared as in the table below. Transient transfections were carried out using a standard protocol for PEI transfection of Adherent cell lines, in HEK293 cells. DNA:PEI ratio 1:2.5 was used, with 0.14 µg total DNA transfected per well of 96 well plate. Plasmids were added in equimolar ratios, with each mix tested in triplicate.

For the cumate solution, a stock solution of 5 mg/mL was prepared by dissolving cumate (Sigma, 268402) in 95% EtOH (Honeywell, 24103). 3 µL of either cumate stock solution or 95% EtOH was added to 197 µL DMEM+10% FBS. Prior to addition of DNA:PEI complexes to cells, 5 µL of either cumate-DMEM or EtOH-DMEM was added to each well (final cumate concentration of 30 µg/mL). 72 hours post-transfection cells were prepared for flow cytometry analysis using the Attune NxT Flow Cytometer.

TABLE

DNA mixes for transfections

| DNA mix | EGFP plasmid | Other |
|---|---|---|
| 1 - 6xCuO_minCMV-EGFP + rc-CymR-VP16 | Q5868 | Q5874 |
| 2 - 6xCuO_minCMV-EGFP + rc-CymR-p53 | Q5868 | Q5873 |
| 3 - 6xCuO_minCMV-EGFP + rc-CymR | Q5868 | Q5812 |
| 4 - 6xCuO_minCMV-EGFP | Q5868 | OG10 |
| 5 - minCMV-EGFP + rc-CymR-VP16 | Q437 | Q5874 |

TABLE-continued

DNA mixes for transfections

| DNA mix | EGFP plasmid | Other |
|---|---|---|
| 6 - minCMV-EGFP + rc-CymR-p53 | Q437 | Q5873 |
| 7 - minCMV-EGFP + rc-CymR | Q437 | Q5812 |
| 8 - minCMV-EGFP | Q437 | OG10 |
| 9 - CMV-EGFP | Q414 | OG10 |

Results

Figure 9:
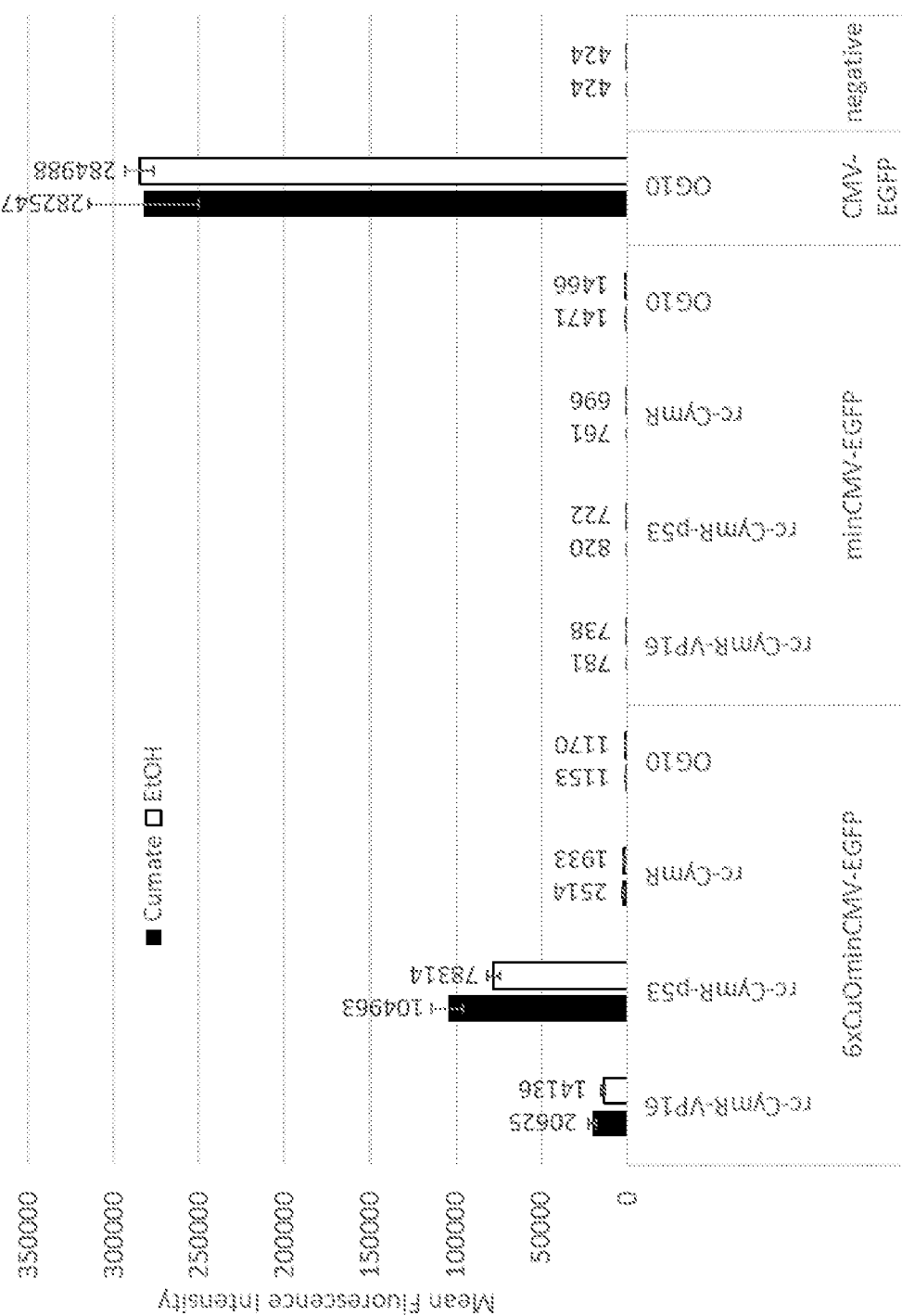
FIG. 9. Mean fluorescence intensity of HEK293 cells. Error bars depict standard deviation, n=3 (biological triplicate, analytical single).

FIG. 9 shows the mean fluorescence intensity after 72 hours. It is immediately clear that as observed previously, there was minimal background EGFP expression resulting from either the minimal CMV or the 6×CuO_minCMV promoter without induction. There was also no significant difference between the constitutive samples with and without cumate.

What was hypothesized was that with the inducible EGFPF+rc-CymR-TAD, EGFP expression would be observed with cumate but not without. However, although there was significantly higher EGFP expression with cumate than without, there was still significant observable EGFP expression without cumate. For rc-CymR-VP16, this amounted to approximately 19-fold more expression than the equivalent negative control. For rc-CymR-p53 this value is even higher, at over 100-fold more.

Upon induction with cumate, the EGFP expression was not as high as anticipated. For rc-CymR-VP16, induced EGFP was 7.3% of the constitutive, whilst rc-CymR-p53 performed better, at 37%. Neither, however, were close to the ideal 75% induction compared to the constitutive.

Overall, although rc-CymR was showing altered DNA binding properties with relation to cumate compared to CymR, there was high residual binding without cumate present. In a stable cell line context, this would lead to high basal expression of cytotoxic Rep proteins, and poor control upon induction of the system with cumate.

Corresponding experiments were performed in the context of rAAV production and similar results were obtained. Significant rc-CymR-VP16 binding was observed in the absence of cumate. In this instance, the inducible RepCap showed 2.5% viral production compared to the constitutive, when no rc-CymR-VP16 was present. However, when rc-CymR-VP16 was present, both with and without cumate there was no significant difference to the constitutive expression. Furthermore, there was very high rAAV production when no cumate was present. This indicated that the induction system would not work in a stable cell line in this form.

Example 5: Dual Control System

A new strategy was designed to reduce background rc-CymR DNA binding in the absence of cumate. This system involves what is known as 'dual cumate control', whereby there are two concurrent systems operating to prevent transcription of the target gene, which are both relieved by addition of cumate.

FIGS. 1A and 1B show schematics for how this system operates with and without cumate. For simplicity, the target regulated gene is EGFP; in a producer cell line, it would be the regulated AAV packaging elements. Three core DNA components of the system are required: a constitutively expressed CymR protein; a CymR-repressible rc-CymR-TAD protein; the target regulated gene driven by the 6×CuO_minCMV promoter (requiring CymR-TAD or rc-CymR-TAD binding for activation).

In the absence of cumate, only the CymR is expressed and this has two functions: First, the CymR binds to the CuO in the rc-CymR-TAD promoter, repressing transcription of rc-CymR-TAD—thereby preventing the background binding that was observed when rc-CymR was used alone. Second, CymR will bind to the 6×CuO_minCMV promoter and sterically block any rc-CymR-TAD that has been transcribed through leakiness of the CymR-repression. The constitutive expression of CymR is likely to greatly outcompete any rc-CymR-TAD for binding at these 6×CuO sites—thereby the target regulated gene is kept off.

When cumate is added, the CymR can no longer bind to DNA. This will remove the steric block at the 6×CuO sites and relieve repression of the rc-CymR-TAD promoter. Furthermore, the cumate should fully activate DNA binding abilities of rc-CymR-TAD—allowing the transcriptional activation of the target regulated gene through the single addition of cumate.

In a pilot experiment, EGFP expression from an inducible plasmid (Q5868, pSF-6×CuO_minCMV-EGFP) was tested using this dual cumate control system.

Plasmid Design

Most of the plasmids needed to test this system using an inducible EGFP were already available, with the exception of the repressible rc-CymR-TAD. This was cloned by placing a CMV_CuO promoter upstream of a rc-CymR-VP16 coding sequence, resulting in Q6440 (pSF-CMV_CuO-rc-CymR-VP16).

Transfection Setup

Six DNA mixes were prepared as per the table below. Transient transfections were carried out using a standard protocol for PEI transfection of Adherent cell lines, in HEK293 cells. DNA:PEI ratio 1:2.5 was used, with 0.14 μg total DNA transfected per well of 96 well plate. Plasmids were added in equimolar ratios, with each mix tested in triplicate.

For the cumate solution, a stock solution of 5 mg/mL was prepared by dissolving cumate (Sigma, 268402) in 95% EtOH (Honeywell, 24103). 3 μL of either cumate stock solution or 95% EtOH was added to 197 μL DMEM+10% FBS. Prior to addition of DNA:PEI complexes to cells, 5 μL of either cumate-DMEM or EtOH-DMEM was added to each well (final cumate concentration of 30 μg/mL).

TABLE

DNA mixes for transfections

| DNA mix | EGFP plasmid | Other | |
|---|---|---|---|
| 1 - 6×CuO_minCMV-EGFP + CMV_CuO-rc-CymR-VP16 + CymR | Q5868 | Q6440 | Q4721 |
| 2 - 6×CuO_minCMV-EGFP + CMV_CuO-rc-CymR-VP16 | Q5868 | Q6440 | T176 |
| 3 - 6×CuO_minCMV-EGFP + CMV-rc-CymR-VP16 + CymR | Q5868 | Q5874 | Q4721 |
| 4 - 6×CuO_minCMV-EGFP + CMV-rc-CymR-VP16 | Q5868 | Q5874 | T176 |
| 5 - minCMV-EGFP +CMV-rc-CymR-VP16 + CymR | Q437 | Q5874 | Q4721 |
| 6 - CMV-EGFP + CMV-rc-CymR-VP16 + CymR | Q414 | Q5874 | Q4721 |

Results

Figure 10A:
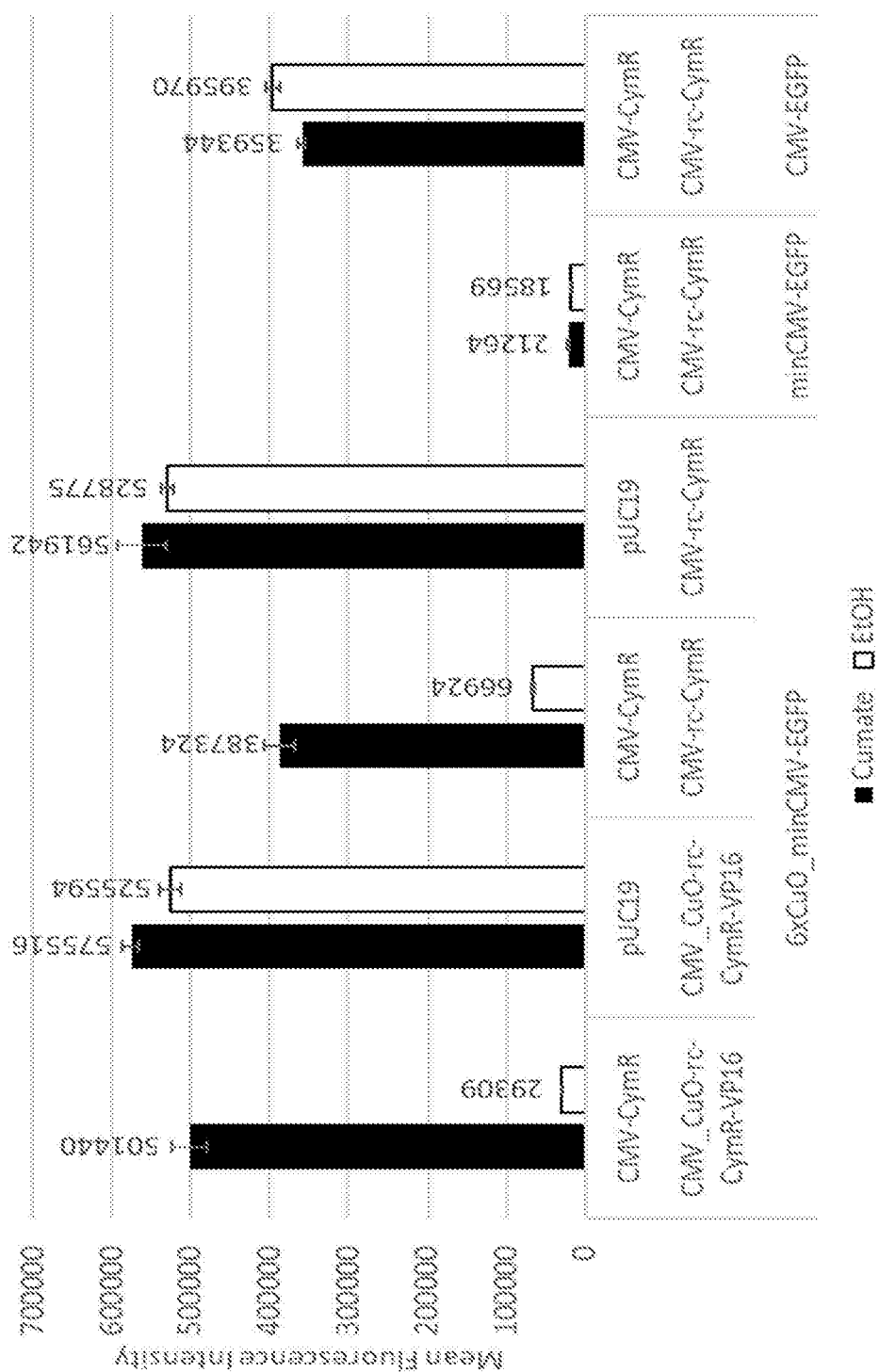
FIG. 10A. Flow cytometry data from eGFP expression using dual cumate system-mean fluorescence intensity. Error bars depict standard deviation (n=3, biological triplicate, analytical single).
Figure 10B:
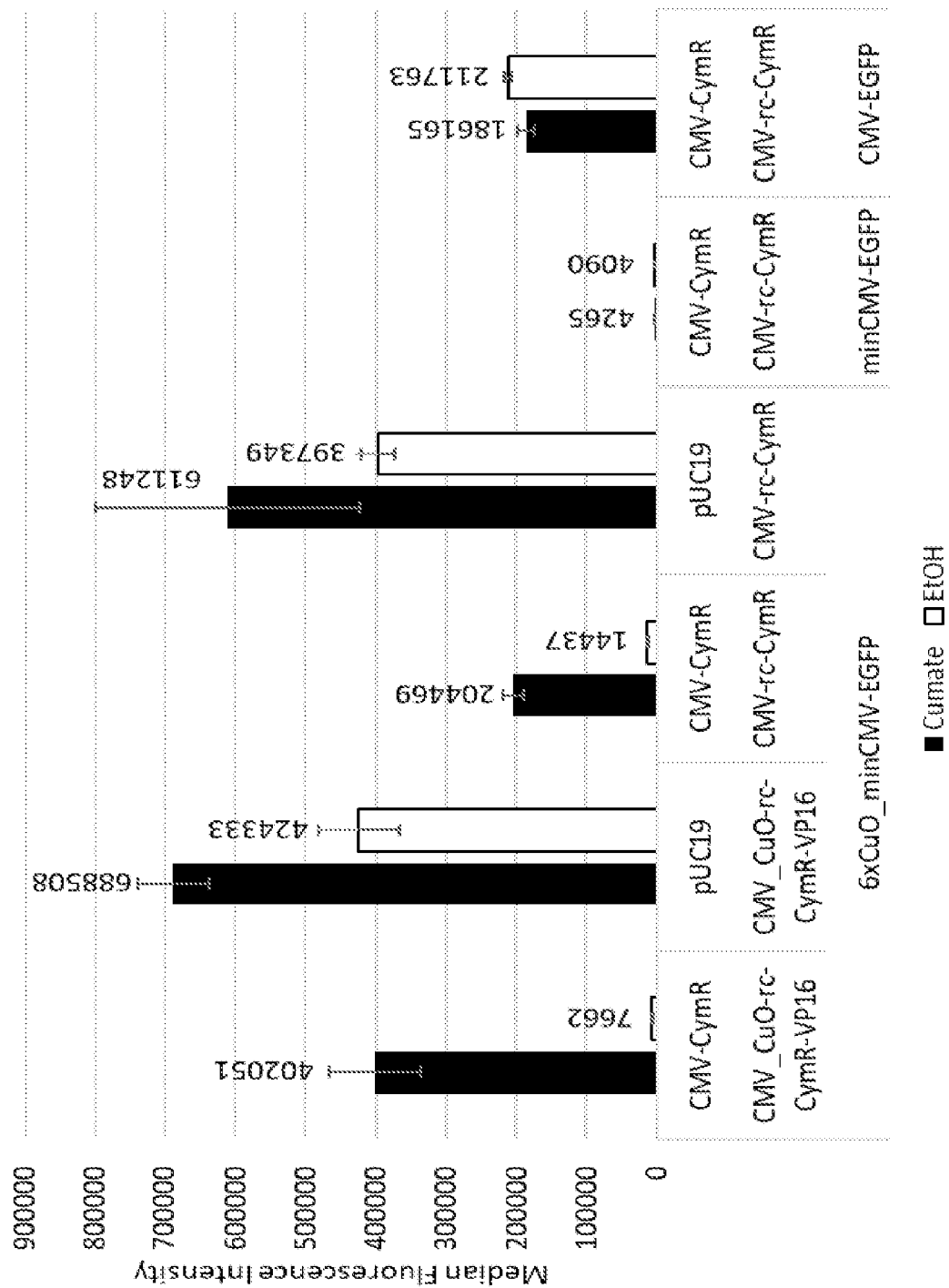
FIG. 10B. Flow cytometry data from eGFP expression using dual cumate system-median fluorescence intensity. Error bars depict standard deviation (n=3, biological triplicate, analytical single).

FIGS. 10A and 10B show the flow cytometry data for samples after 72 hours. From the mean fluorescence intensity, it was apparent that the dual control system has restored stringency to the system of using cumate to activated rc-CymR-TAD DNA binding as the activation of the target regulated gene (EGFP).

Where the system was fully present (6×CuO_minCMV-EGFP+CMV_CuO-rc-CymR-VP16+CMV-CymR), there were significant differences between the samples with cumate and without. Without cumate, with the system intended to be "off", there was 7.4% fluorescence compared to the constitutive, and just 1.6-fold more than the negative minCMV control. Conversely, upon addition of cumate, there was over 100% fluorescence compared to the constitutive, with induction giving a 17-fold increase.

As previously observed above, when no CMV-CymR was present (6×CuO_minCMV-EGFP+CMV_CuO-rc-CymR-VP16) there was little difference between samples with and without cumate. This correlated with previous observations that there was high rc-CymR DNA binding even in the absence of cumate. In this scenario, the CMV CuO was basally active, unless repressed by CymR protein.

The dual effect of the control was observable when the rc-CymR-VP16 was not regulated, but CMV-CymR was present (6×CuO_minCMV-EGFP+CMV_CuO-rc-CymR-VP16+CMV-CymR). The rc-CymR-VP16 was not being repressed by CymR, but it was facing competition for binding at the 6×CuO sites. Without cumate, when CymR was able to bind CuO sites, there was significantly lower EGFP intensity than the induced when CymR was prevented from binding due to presence of cumate. The repression was 16.9% of the constitutive equivalent. Upon induction, EGFP fluorescence intensity increased over 5-fold.

There was no significant difference between samples with and without cumate for the negative promoter control and positive promoter control (minCMV-EGFP and CMV-EGFP respectively).

Example 6: Reverse Cumate Dual Control System Using CymR and Rc_CymR-VP16 Present on a Transgene Cassette Plasmid CymR and rc_CymR-VP16 were cloned from Q4721 (pSF-CMV-CymR) and Q6440 (pSF-CMV-CuO-rc_CymR-VP19 respectively into the vector backbone of Q6794 (pSF-AAV-ITR-CMV-EGFP-ITR), generating Q9003 (pSF-AAV-CMV-CuO-rc_CymR-VP16-CMV-EGFP-CMV-CymRSalIMluI).

293 baseline suspension cells were transfected by PEIPro (1 µg DNA:2p1 PEIPro) in 24 deep well format, 3 µg DNA per well. Enough transfection mix was prepared for four well per test plasmid condition, giving 2 vehicle control wells and 2 cumate treated wells. Final concentration of cumate added to each well was 30 µg/ml, with the equivalent volume of 95% ethanol (EtOH) applied to vehicle control wells. Treatment applied to each well by addition of 100 µl BalanCD media after application of transfection mix. Positive control transfections for standard AA5 production (Q6794+Q5220+Q1364) were also performed alongside test conditions as well as the negative controls: no genome (OG590+Q5220+Q1364) and no RepCap (Q6794+OG590+Q1364). OG590 (pUC19) used as stuffer in control transfections using the equivalent volume of DNA as the positive control in each instance.

Q7981 is pSF-AAV-6×CuO-Cap5-EMCV-Rep-E4VAI-UB-loxP-Puro-loxP.

Q7951 is pSF-AAV-6×CuO-Cap5-EMCV-Rep-6×CuO-E4VAI-UB-Puro.

Q6794 pSF-ITR-CMV-EGFP-ITR.

| 24DWP Well # | Experiment Description | Plasmid codes |
|---|---|---|
| 1-2 | All-in-one transactivator + inducible Cap + Vehicle control | Q9003 + Q7981 |
| 3-4 | All-in-one transactivator + inducible Cap + Cumate | Q9003 + Q7981 |
| 5-6 | All-in-one transactivator + inducible Cap/inducible VAIE4 + Vehicle control | Q9003 + Q7951 |
| 7-8 | All-in-one transactivator + inducible Cap/inducible VAIE4 + Cumate | Q9003 + Q7951 |
| 9-10 | Triple Transfection | Q6794 + Q1364 + Q5220 |
| 11-12 | No RepCap control | Q6794 + Q1364 + OG590 |
| 13-14 | No genome control | OG590 + Q5220 + Q1364 |
| 15-16 | EGFP control | Q414 |
| 17 | Cumate control | — |
| 18 | Vehicle control (95% EtoH) | — |

Cells were harvested 3 days post transfection by standard chemical lysate. Samples were process for qPCR using the standard DNaseI and proteinase K treatment. qPCR performed using the UTR primer/probe mix with linear Q6794 used as a serially-diluted standard for quantification of sample viral genomes (VG)/ml.

Figure 11:
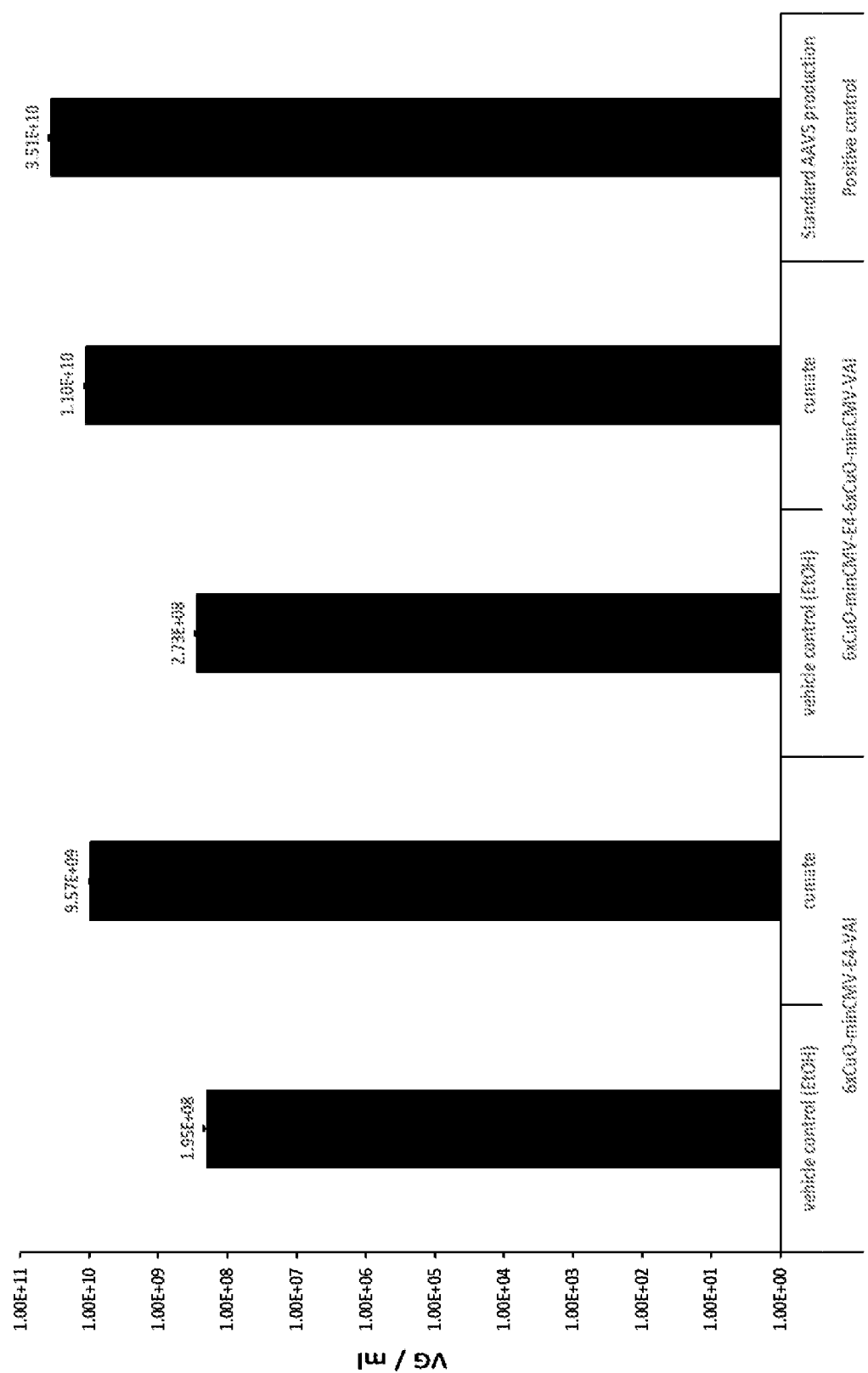
FIG. 11. qPCR data showing vector genomes per ml (VG/mL).
Figure 12:
FIG. 12. qPCR data showing vector genomes per ml (VG/mL).

The results are shown in FIGS. 11-12. In the absence of cumate, basal virus production was <2.5% of cumate-induced production. Cumate-induced production yielded 27-31% of the VG/ml compared to standard triple transfection. Data is shown as the average VG/ml from the two biological replicates from the single transfection; errors bars are for the combined standard error.

Example 7: Validation of CymR-Transactivators in rAAV Production in Suspension HEK293 Cells Validation of the proposed induction system for a stable packaging cell line involved a screen of all CymR-TAD plasmids with various "all-in-one" plasmids.
Experiment Design and Setup
24 hours prior to transfection, two 24 deep-well plates were seeded with 1.0E+06 cells/mL of HEK 293-OX (parental cell line) with a total of 3 mL per well, in BalanCD media. Cells were seeded at passage number 14. Fourteen DNA mixes were set up according to the Table below.

TABLE

DNA mixes for transfections

| | DNA mix | Transgene Plasmid | Packaging Plasmid | Other Plasmid |
|---|---|---|---|---|
| 1 | Inducible RepCap | CymR-VP16 | Q4346 | Q6297 | Q5622 |
| 2 | Inducible RepCap | CymR-p53 | Q4346 | Q6297 | Q5624 |
| 3 | Inducible RepCap | Cym R-VP32 | Q4346 | Q6297 | Q5973 |
| 4 | Inducible RepCap | CymR-p53x2 | Q4346 | Q6297 | Q5814 |
| 5 | Inducible RepCap | CymR-VP16-p53 | Q4346 | Q6297 | Q5974 |
| 6 | Inducible RepCap | CymR-p53-VP16 | Q4346 | Q6297 | Q5813 |
| 7 | Inducible RepCap | CymR-VP16-GS | Q4346 | Q6297 | Q5866 |
| 8 | Inducible RepCap | N/A | Q4346 | Q6297 | T176 |
| 9 | Constitutive RepCap | N/A | Q4346 | Q6295 | N/A |

TABLE-continued

DNA mixes for transfections

| | DNA mix | Transgene Plasmid | Packaging Plasmid | Other Plasmid |
|---|---|---|---|---|
| 10 | RepCap 5 production control 1 | N/A | Q4346 | Q4658 | Q1364 |
| 11 | RepCap 5 production control 2 | N/A | Q4346 | Q5220 | Q1364 |
| 12 | No RepCap control | N/A | Q4346 | T176 | Q1364 |
| 13 | No Genome control | N/A | T176 | Q5220 | Q1364 |
| 14 | EGFP Transfection control | N/A | N/A | N/A | Q414 |

Results

Crude AAV samples were analyzed for titre values by qPCR, to ascertain how the inducible plasmid performs in a suspension HEK293 system, and to compare each CymR-TAD against one another. The primers for qPCR targeted the UTR of the transgene plasmid, with plasmid Q4346 used as the standard.

Figure 13:
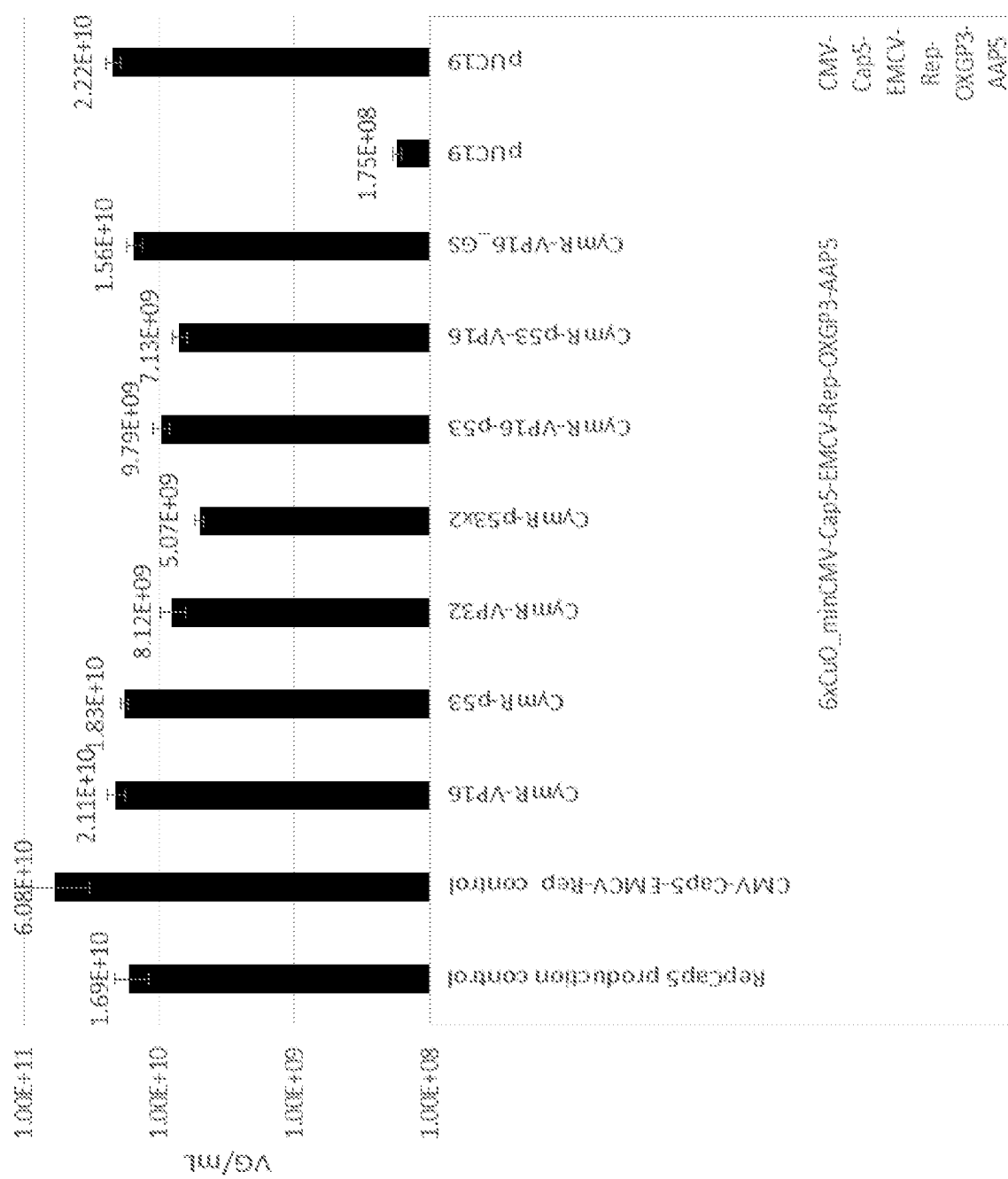
FIG. 13. qPCR data showing rAV5 vector genomes per mL. Error bars depict standard deviation, with n=4 (biological duplicate, analytical duplicate).

FIG. 13 shows the viral genomes per mL. Immediately apparent is that with no transactivator there is very low viral production (1.75E+08 VG/m L). This corresponds to 0.8% of the constitutive equivalent; this shows very stringent repression. This result shows that the inducible promoter is sufficiently inactive, in a suspension HEK293 cells.

The constitutive "re-configured" control (CMV-Cap5-EMCV-Rep control) is the highest performer. This is not surprising as it has superior helper functions supplied by Q1364 (containing E2A, E4 and VAI regions). Similarly, Q4658 (pSF-RepCap5) also was tested in combination with Q1364. These two served as production controls to ensure that production itself is within the expected range. Therefore, these two values cannot be compared to the rest of the data—but indicate that the experimental setup was a success. Similarly, the no-genome and no-repcap controls are not depicted on the graphs as they fell outside the range of the standard curve and can be considered negligible.

Comparing each CymR-TA, we see that the top three are CymR-VP16, CymR-p53 and CymR-VP16_GS. These give 95%, 82% and 70% viral titre compared to the constitutive.

Overall, these data demonstrate that the proposed induction system for use in a stable AAV packaging cell line meets both criteria for repression and activation in suspension HEK293 cells. Less than 1% viral production is observed in the "off" state, and up to 95% activation is seen upon addition of the DNA activator CymR-TA.

```
SEQUENCES
Rep nucleotide sequence (AAV serotype 2)
                                               SEQ ID NO: 1
atgccggggttttacgagattgtgattaaggtccccagcgaccttgacgagcatctgcccgca tttctgacagctttgtgaactgggtggccgagaaggaatgggagttgccgccagattctgacat ggatctgaatctgattgagcaggcaccctgaccgtggccgagaagctgcagcgcgactttctg acggaatggcgccgtgtgagtaaggccccggaggcccttttctttgtgcaatttgagaagggag agagctacttccacatgcacgtgctcgtggaaaccaccggggtgaaatccatggttttgggacg tttcctgagtcagattcgcgaaaaactgattcagagaatttaccgcgggatcgagccgactttg ccaaactggttcgcggtcacaaagaccagaaatggcgccggaggcgggaacaaggtggtggatg agtgctacatcccaattacttgctcccaaaacccagcctgagctccagtgggcgtggactaa tatggaacagtatttaagcgcctgtttgaatctcacggagcgtaaacggttggtggcgcagcat ctgacgcacgtgtcgcagacgcaggagcagaacaaagagaatcagaatcccaattctgatgcgc cggtgatcagatcaaaaacttcagccaggtacatggagctggtcgggtggctcgtggacaaggg gattacctcggagaagcagtggatccaggaggaccaggcctcatacatctccttcaatgcggcc tccaactcgcggtcccaaatcaaggctgccttggacaatgcgggaaagattatgagcctgacta aaaccgccccgactacctggtgggccagcagcccgtggaggacatttccagcaatcggattta taaaattttggaactaaacgggtacgatccccaatatgcggcttccgtctttctgggatgggcc acgaaaaagttcggcaagaggaacaccatctggctgtttgggcctgcaactaccgggaagacca acatcgcggaggccatagcccacactgtgcccttctacgggtgcgtaaactggaccaatgagaa ctttcccttcaacgactgtgtcgacaagatggtgatctggtgggaggaggggaagatgaccgcc aaggtcgtggagtcggccaaagccattctcggaggaagcaaggtgcgcgtggaccagaaatgca agtcctcggcccagatagacccgactcccgtgatcgtcacctccaacaccaacatgtgcgccgt gattgacgggaactcaacgaccttcgaacaccagcagccgttgcaagaccggatgttcaaattt gaactcacccgccgtctggatcatgactttgggaaggtcaccaagcaggaagtcaaagactttt tccggtgggcaaaggatcacgtggttgaggtggagcatgaattctacgtcaaaaagggtggagc caagaaaagacccgcccccagtgacgcagatataagtgagcccaaacgggtgcgcgagtcagtt
```

-continued

```
gcgcagccatcgacgtcagacgcggaagcttcgatcaactacgcagacaggtaccaaaacaaat gttctcgtcacgtgggcatgaatctgatgctgtttccctgcagacaatgcgagagaatgaatca gaattcaaatatctgcttcactcacggacagaaagactgtttagagtgctttcccgtgtcagaa tctcaacccgtttctgtcgtcaaaaaggcgtatcagaaactgtgctacattcatcatatcatgg gaaaggtgccagacgcttgcactgcctgcgatctggtcaatgtggatttggatgactgcatctt tgaacaaTAG
```

Rep78 amino acid sequence (AAV serotype 2)
                                                    SEQ ID NO: 2
MPGFYEIVIKVPSDLDGHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGITSEKQWIQEDQASYISFNAA

SNSRSQIKAALDNAGKIMSLIKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVISNINMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*

Rep68 amino acid sequence (AAV serotype 2)
                                                    SEQ ID NO: 3
MPGFYEIVIKVPSDLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGITSEKQWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYAD*

Rep52 amino acid sequence (AAV serotype 2)
                                                    SEQ ID NO: 4
MELVGWLVDKGITSEKQWIQEDQASYISFNAASNSRSQIKAALDNAGKIMSLTKTAPDYLVGQQ

PVEDISSNRIYKILELNGYDPQYAASVFLGWATKKFGKRNTIWLFGPATTGKTNIAEAIAHTVP

FYGCVNWTNENFPFNDCVDKMVIWWEEGKMTAKVVESAKAILGGSKVRVDQKCKSSAQIDPTPV

IVTSNTNMCAVIDGNSTTFEHQQPLQDRMFKFELTRRLDHDFGKVTKQEVKDFFRWAKDHVVEV

EHEFYVKKGGAKKRPAPSDADISEPKRVRESVAQPSTSDAEASINYADRYQNKCSRHVGMNLML

FPCRQCERMNQNSNICFTHGQKDCLECFPVSESQPVSVVKKAYQKLCYIHHIMGKVPDACTACD

LVNVDLDDCIFEQ*

Rep40 amino acid sequence (AAV serotype 2)
                                                    SEQ ID NO: 5
MELVGWLVDKGITSEKQWIQEDQASYISFNAASNSRSQIKAALDNAGKIMSLTKTAPDYLVGQQ

PVEDISSNRIYKILELNGYDPQYAASVFLGWATKKFGKRNTIWLFGPATTGKTNIAEAIAHTVP

FYGCVNWTNENFPFNDCVDKMVIWWEEGKMTAKVVESAKAILGGSKVRVDQKCKSSAQIDPTPV

IVTSNTNMCAVIDGNSTTFEHQQPLQDRMFKFELTRRLDHDFGKVTKQEVKDFFRWAKDHVVEV

EHEFYVKKGGAKKRPAPSDADISEPKRVRESVAQPSTSDAEASINYADRLARGHSL*

Rep78 nucleotide sequence (AAV serotype 2)
SEQ ID NO: 6 atgccggggttttacgagattgtgattaaggtccccagcgaccttgacgggcatctgcccggca tttctgacagctttgtgaactgggtggccgagaaggaatgggagttgccgccagattctgacat ggatctgaatctgattgagcaggcacccctgaccgtggccgagaagctgcagcgcgactttctg acggaatggcgccgtgtgagtaaggccccggaggccttttctttgtgcaatttgagaagggag agagctacttccacatgcacgtgctcgtggaaaccaccggggtgaaatccatggttttgggacg tttcctgagtcagattcgcgaaaaactgattcagagaatttaccgcgggatcgagccgactttg ccaaactggttcgcggtcacaaagaccagaaatggcgccggaggcgggaacaaggtggtggatg agtgctacatccccaattacttgctccccaaaacccagcctgagctccagtgggcgtggactaa tatgaacagtacctcagcgcctgtttgaatctcacggagcgtaaacggttggtggcgcagcat ctgacgcacgtgtcgcagacgcaggagcagaacaaagagaatcagaatcccaattctgatgcgc cggtgatcagatcaaaaacttcagccaggtacatggagctggtcgggtggctcgtggacaaggg gattacctcggagaagcagtggatccaggaggaccaggcctcatacatctccttcaatgcgcc tccaactcgcggtcccaaatcaaggctgccttggacaatgcgggaaagattatgagcctgacta aaaccgcccccgactacctggtgggccagcagcccgtggaggacatttccagcaatcggattta taaaattttggaactaaacgggtacgatccccaatatgcggcttccgtctttctgggatgggcc acgaaaaagttcggcaagaggaacaccatctggctgtttgggcctgcaactaccgggaagacca acatcgcggaggccatagcccacactgtgcccttctacgggtgcgtaaactggaccaatgagaa ctttcccttcaacgactgtgtcgacaagatggtgatctggtggaggaggggaagatgaccgcc aaggtcgtggagtcggccaaagccattctcggaggaagcaaggtgcgcgtggaccagaaatgca agtcctcggcccagatagacccgactcccgtgatcgtcacctccaacaccaacatgtgcgccgt gattgacgggaactcaacgaccttcgaacaccagcagccgttgcaagaccggatgttcaaattt gaactcacccgcgtctggatcatgactttgggaaggtcaccaagcaggaagtcaaagacttt tccggtgggcaaaggatcacgtggttgaggtggagcatgaattctacgtcaaaaagggtggagc caagaaaagacccgccccagtgacgcagatataagtgagcccaaacgggtgcgcgagtcagtt gcgcagccatcgacgtcagacgcggaagcttcgatcaactacgcagacaggtaccaaaacaaat gttctcgtcacgtgggcatgaatctgatgctgtttccctgcagacaatgcgagagaatgaatca gaattcaaatatctgcttcactcacggacagaaagactgtttagagtgctttcccgtgtcagaa tctcaacccgtttctgtcgtcaaaaaggcgtatcagaaactgtgctacattcatcatatcatgg gaaaggtgccagacgcttgcactgcctgcgatctggtcaatgtggatttggatgactgcatctt tgaacaaTAG Rep68 nucleotide sequence (AAV serotype 2)
SEQ ID NO: 7

ATGCCGGGGTTTTACGAGattgtgattaaggtccccagcgaccttgacgagcatctgcccggca tttctgacagctttgtgaactgggtggccgagaaggaatgggagttgccgccagattctgacat ggatctgaatctgattgagcaggcacccctgaccgtggccgagaagctgcagcgcgactttctg acggaatggcgccgtgtgagtaaggccccggaggccttttctttgtgcaatttgagaagggag agagctacttccacatgcacgtgctcgtggaaaccaccggggtgaaatccatggttttgggacg tttcctgagtcagattcgcgaaaaactgattcagagaatttaccgcgggatcgagccgactttg ccaaactggttcgcggtcacaaagaccagaaatggcgccggaggcgggaacaaggtggtggatg

```
agtgctacatccccaattacttgctccccaaaacccagcctgagctccagtgggcgtGGACTAA

TATGGAACAGTACCTCAGCGCCTGTTTGAATCTCACGGagcgtaaacggttggtggcgcagcat ctgacgcacgtgtcgcagacgcaggagcagaacaaagagaatcagaatcccaattctgatgcgc cggtgatcagatcaaaaacttcagccaggtacatggagctggtcgggtggctcgtggacaaggg gattacctcggagaagcagtggatccaggaggaccaggcctcatacatctccttcaatgcggcc tccaactcgcggtcccaaatcaaggctgccttggacaatgcgggaaagattatgagcctgacta aaaccgccccgactacctggtgggccagcagcccgtggaggacatttccagcaatcggattta taaaattttggaactaaacgggtacgatccccaatatgcggcttccgtctttctgggatgggcc acgaaaaagttcggcaagaggaacaccatctggctgtttgggcctgcaactaccgggaagacca acatcgcggaggccatagcccacactgtgcccttctacgggtgcgtaaactggaccaatgagaa ctttcccttcaacgactgtgtcgacaagatggtgatctggtggggaggaggggaagatgaccgcc aaggtcgtggagtcggccaaagccattctcggaggaagcaaggtgcgcgtggaccagaaatgca agtcctcggcccagatagacccgactcccgtgatcgtcacctccaacaccaacatgtgcgccgt gattgacgggaactcaacgaccttcgaacaccagcagccgttgcaagaccggatgttcaaattt gaactcacccgccgtctggatcatgactttgggaaggtcaccaagcaggaagtcaaagactttt tccggtgggcaaaggatcacgtggttgaggtggagcatgaattctacgtcaaaaagggtggagc caagaaaagacccgcccccagtgacgcagatataagtgagcccaaacgggtgcgcgagtcagtt gcgcagccatcgacgtcagacgcggaagcttcgatcaactacgcagacagTAG Rep52 nucleotide sequence:
                                                SEQ ID NO: 8
CATGGAGCTGGTCGGGTGGctcgtggacaaggggattacctcggagaagcagtggatccaggag gaccaggcctcatacatctccttcaatgcggcctccaactcgcggtcccaaatcaaggctgcct tggacaatgcgggaaagattatgagcctgactaaaaccgccccgactacctggtgggccagca gcccgtggaggacatttccagcaatcggatttataaaattttggaactaaacgggtacgatccc caatatgcggcttccgtctttctgggatgggccacgaaaaagttcggcaagaggaacaccatct ggctgtttgggcctgcaactaccgggaagaccaacatcgcggaggccatagcccacactgtgcc cttctacgggtgcgtaaactggaccaatgagaactttcccttcaacgactgtgtcgacaagatg gtgatctggtggggaggaggggaagatgaccgccaaggtcgtggagtcggccaaagccattctcg gaggaagcaaggtgcgcgtggaccagaaatgcaagtcctcggcccagatagacccgactcccgt gatcgtcacctccaacaccaacatgtgcgccgtgattgacgggaactcaacgaccttcgaacac cagcagccgttgcaagaccggatgttcaaatttgaactcacccgccgtctggatcatgactttg ggaaggtcaccaagcaggaagtcaaagacttttttccggtgggcaaaggatcacgtggttgaggt ggagcatgaattctacgtcaaaaagggtggagccaagaaaagacccgcccccagtgacgcagat ataagtgagcccaaacgggtgcgcgagtcagttgcgcagccatcgacgtcagacgcggaagctt cgatcaactacgcagacaggtaccaaaacaaatgttctcgtcacgtgggcatgaatctgatgct gtttccctgcagacaatgcgagagaatgaatcagaattcaaatatctgcttcactcacggacag aaagactgtttagagtgctttcccgtgtcagaatctcaacccgtttctgtcgtcaaaaaggcgt atcagaaactgtgctacattcatcatatcatgggaaaggtgccagacgcttgcactgcctgcga tctggtcaatgtggatttggatgaCTGCATCTTTGAACAATAG
```

-continued

Rep40 nucleotide sequence:
SEQ ID NO: 9

ATGGAGCTGGTCGGGTGGctcgtggacaaggggattacctcggagaagcagtggatccaggagg
accaggcctcatacatctccttcaatgcggcctccaactcgcggtcccaaatcaaggctgcctt
ggacaatgcgggaaagattatgagcctgactaaaaccgcccccgactacctggtgggccagcag
cccgtggaggacatttccagcaatcggatttataaaattttggaactaaacgggtacgatcccc
aatatgcggcttccgtctttctgggatgggccacgaaaaagttcggcaagaggaacaccatctg
gctgtttgggcctgcaactaccgggaagaccaacatcgcggaggccatagcccacactgtgccc
ttctacgggtgcgtaaactggaccaatgagaactttcccttcaacgactgtgtcgacaagatgg
tgatctggtgggaggaggggaagatgaccgccaaggtcgtggagtcggccaaagccattctcgg
aggaagcaaggtgcgcgtggaccagaaatgcaagtcctcggcccagatagacccgactcccgtg
atcgtcacctccaacaccaacatgtgcgccgtgattgacgggaactcaacgaccttcgaacacc
agcagccgttgcaagaccggatgttcaaatttgaactcacccgccgtctggatcatgactttgg
gaaggtcaccaagcaggaagtcaaagacttttttccggtgggcaaaggatcacgtggttgaggtg
gagcatgaattctacgtcaaaaagggtggagccaagaaaagacccgcccccagtgacgcagata
taagtgagcccaaacgggtgcgcgagtcagttgcgcagccatcgacgtcagacgcggaagcttc
gatcaactacgcagacagattggctcgaggacactctctcTAG Cap nucleotide sequence (AAV serotype 2)
SEQ ID NO: 10

Cagttgcgcagccatcgacgtcagacgcggaagcttcgatcaactacgcagacaggtaccaaaa
caaatgttctcgtcacgtgggcatgaatctgatgctgtttccctgcagacaatgcgagagaatg
aatcagaattcaaatatctgcttcactcacggacagaaagactgtttagagtgctttcccgtgt
cagaatctcaacccgtttctgtcgtcaaaaaggcgtatcagaaactgtgctacattcatcatat
catgggaaaggtgccagacgcttgcactgcctgcgatctggtcaatgtggatttggatgactgc
atctttgaacaataaatgatttaaatcaggt
atggctgccgatggttatcttccagattggctcgaggacactctctctgaaggaataagacagt
ggtgaagctcaaacctggcccaccaccaccaaagcccgcagagcggcataaggacgacagcag
gggtcttgtgcttcctgggtacaagtacctcggacccttcaacggactcgacaagggagagccg
gtcaacgaggcagacgccgcggccctcgagcacgacaaagcctacgaccggcagctcgacagcg
gagacaacccgtacctcaagtacaaccacgccgacgcggagtttcaggagcgccttaaagaaga
tacgtcttttgggggcaacctcggacgagcagtcttccaggcgaaaaagagggttcttgaacct
ctgggcctggttgaggaacctgttaagacggctccgggaaaaaagaggccggtagagcactctc
ctgtggagccagactcctcctcgggaaccggaaaggcgggccagcagcctgcaagaaaaagatt
gaattttggtcagactggagacgcagactcagtacctgaccccagcctctcggacagccacca
gcagccccctctggtctgggaactaatacgatggctacaggcagtggcgcaccaatggcagaca
taacgagggcgccgacggagtgggtaattcctcgggaaattggcattgcgattccacatggat
gggcgacagagtcatcaccaccagcacccgaacctgggccctgcccacctacaacaaccacctc
tacaaacaaattccagccaatcaggagcctcgaacgacaatcactactttggctacagcaccc
cttgggggtattttgacttcaacagattccactgccacttttcaccacgtgactggcaaagact
catcaacaacaactggggattccgacccaagagactcaacttcaagctctttaacattcaagtc
aaagaggtcacgcagaatgacggtacgacgacgattgccaataaccttaccagcacggttcagg
tgtttactgactcggagtaccagctcccgtacgtcctcggctcggcgcatcaaggatgcctccc
gccgttcccagcagacgtcttcatggtgccacagtatggataccctcaccctgaacaacgggagt -continued

```
caggcagtaggacgctcttcattttactgcctggagtactttccttctcagatgctgcgtaccg gaaacaactttaccttcagctacacttttgaggacgttcctttccacagcagctacgctcacag ccagagtctggaccgtctcatgaatcctctcatcgaccagtacctgtattacttgagcagaaca aacactccaagtggaaccaccacgcagtcaaggcttcagttttctcaggccggagcgagtgaca ttcgggaccagtctaggaactggcttcctggaccctgttaccgccagcagcgagtatcaaagac atctgcggataacaacaacagtgaatactcgtggactggagctaccaagtaccacctcaatggc agagactctctggtgaatccgggcccggccatggcaagccacaaggacgatgaagaaaagtttt ttcctcagagcggggttctcatctttgggaagcaaggctcagagaaaacaaatgtggacattga aaaggtcatgattacagacgaagaggaaatcaggacaaccaatcccgtggctacggagcagtat ggttctgtatctaccaacctccagagaggcaacagacaagcagctaccgcagatgtcaacacac aaggcgttcttccaggcatggtctggcaggacagagatgtgtaccttcaggggcccatctgggc aaagattccacacacggacggacattttcaccctctccctcatgggtggattcggacttaaa cacctcctccacagattctcatcaagaacaccccggtacctgcgaatccttcgaccaccttca gtgcggcaaagtttgcttccttcatcacacagtactccacgggacaggtcagcgtggagatcga gtgggagctgcagaaggaaaacagcaaacgctggaatcccgaaattcagtacacttccaactac aacaagtctgttaatgtggactttactgtggacactaatggcgtgtattcagagcctcgcccca ttggcaccagatacctgactcgtaatctgtaA
```

Cap amino acid sequence (AAV serotype 2)
SEQ ID NO: 11

MAADGYLPDWLEDTLSEGIRQWWKLKPGPPPPKPAERHKDDSRGLVLPGYKYLGPFNGLDKGEP

VNEADAAALEHDKAYDRQLDSGDNPYLKYNHADAEFQERLKEDTSFGGNLGRAVFQAKKRVLEP

LGLVEEPVKTAPGKKRPVEHSPVEPDSSSGTGKAGQQPARKRLNFGQTGDADSVPDPQPLGQPP

AAPSGLGTNTMATGSGAPMADNNEGADGVGNSSGNWHCDSTWMGDRVITTSTRTWALPTYNNHL

YKQISSQSGASNDNHYFGYSTPWGYFDFNRFHCHFSPRDWQRLINNNWGFRPKRLNFKLFNIQV

KEVTQNDGTTTIANNLTSTVQVFTDSEYQLPYVLGSAHQGCLPPFPADVFMVPQYGYLTLNNGS

QAVGRSSFYCLEYFPSQMLRTGNNFTFSYTFEDVPFHSSYAHSQSLDRLMNPLIDQYLYYLSRT

NTPSGTTTQSRLQFSQAGASDIRDQSRNWLPGPCYRQQRVSKTSADNNNSEYSWTGATKYHLNG

RDSLVNPGPAMASHKDDEEKFFPQSGVLIFGKQGSEKTNVDIEKVMITDEEEIRTTNPVATEQY

GSVSTNLQRGNRQAATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKENSKRWNPEIQYTSNY

NKSVNVDFTVDTNGVYSEPRPIGTRYLTRNL*

EMCV IRES
SEQ ID NO: 14

CGTTACTGGCCGAAGCCGCTTGGAATAAGGCCGGTGTGCGTTTGTCTATATGTTATTTTCCACC

ATATTGCCGTCTTTTGGCAATGTGAGGGCCCGGAAACCTGGCCCTGTCTTCTTGACGAGCATTC

CTAGGGGTCTTTCCCCTCTCGCCAAAGGAATGCAAGGTCTGTTGAATGTCGTGAAGGAAGCAGT

TCCTCTGGAAGCTTCTTGAAGACAAACAACGTCTGTAGCGACCCTTTGCAGGCAGCGGAACCCC

CCACCTGGCGACAGGTGCCTCTGCGGCCAAAAGCCACGTGTATAAGATACACCTGCAAAGGCGG

CACAACCCCAGTGCCACGTTGTGAGTTGGATAGTTGTGGAAAGAGTCAAATGGCTCCCCTCAAG

CGTATTCAACAAGGGGCTGAAGGATGCCCAGAAGGTACCCCATTGTATGGGATCTGATCTGGGG

CCTCGGTGCACATGCTTTACATGTGTTTAGTCGAGGTTAAAAAACGTCTAGGCCCCCCGAACCA

CGGGGAC

-continued

FMDV IRES

SEQ ID NO: 15

AGCAGGTTTCCCCAACTGACACAAAACGTGCAACTTGAAACTCCGCCTGGTCTTTCCAGGTCTA

GAGGGGTAACACTTTGTACTGCGTTTGGCTCCACGCTCGATCCACTGGCGAGTGTTAGTAACAG

CACTGTTGCTTCGTAGCGGAGCATGACGGCCGTGGGAACTCCTCCTTGGTAACAAGGACCCACG

GGGCCAAAAGCCACGCCCACACGGGCCCGTCATGTGTGCAACCCCAGCACGGCGACTTTACTGC

GAAACCCACTTTAAAGTGACATTGAAACTGGTACCCACACACTGGTGACAGGCTAAGGATGCCC

TTCAGGTACCCCGAGGTAACACGCGACACTCGGGATCTGAGAAGGGGACTGGGGCTTCTATAAA

AGCGCTCGGTTTAAAAAGCTTCTATGCCTGAATAGGTGACCGGAGGTCGGCACCTTTCCTTTGC

AATTACTGACCAC

Ad5 E2A

SEQ ID NO: 16

GGTACCCAACTCCATGCTCAACAGTCCCCAGGTACAGCCCACCCTGCGTCGCAACCAGGAACAG

CTCTACAGCTTCCTGGAGCGCCACTCGCCCTACTTCCGCAGCCACAGTGCGCAGATTAGGAGCG

CCACTTCTTTTTGTCACTTGAAAAACATGTAAAAATAATGTACTAGAGACACTTTCAATAAAGG

CAAATGCTTTTATTTGTACACTCTCGGGTGATTATTTACCCCCACCCTTGCCGTCTGCGCCGTT

TAAAAATCAAAGGGGTTCTGCCGCGCATCGCTATGCGCCACTGGCAGGGACACGTTGCGATACT

GGTGTTTAGTGCTCCACTTAAACTCAGGCACAACCATCCGCGGCAGCTCGGTGAAGTTTTCACT

CCACAGGCTGCGCACCATCACCAACGCGTTTAGCAGGTCGGGCGCCGATATCTTGAAGTCGCAG

TTGGGGCCTCCGCCCTGCGCGCGCGAGTTGCGATACACAGGGTTGCAGCACTGGAACACTATCA

GCGCCGGGTGGTGCACGCTGGCCAGCACGCTCTTGTCGGAGATCAGATCCGCGTCCAGGTCCTC

CGCGTTGCTCAGGGCGAACGGAGTCAACTTTGGTAGCTGCCTTCCCAAAAAGGGCGCGTGCCCA

GGCTTTGAGTTGCACTCGCACCGTAGTGGCATCAAAAGGTGACCGTGCCCGGTCTGGGCGTTAG

GATACAGCGCCTGCATAAAAGCCTTGATCTGCTTAAAAGCCACCTGAGCCTTTGCGCCTTCAGA

GAAGAACATGCCGCAAGACTTGCCGGAAAACTGATTGGCCGGACAGGCCGCGTCGTGCACGCAG

CACCTTGCGTCGGTGTTGGAGATCTGCACCACATTTCGGCCCCACCGGTTCTTCACGATCTTGG

CCTTGCTAGACTGCTCCTTCAGCGCGCGCTGCCCGTTTTCGCTCGTCACATCCATTTCAATCAC

GTGCTCCTTATTTATCATAATGCTTCCGTGTAGACACTTAAGCTCGCCTTCGATCTCAGCGCAG

CGGTGCAGCCACAACGCGCAGCCCGTGGGCTCGTGATGCTTGTAGGTCACCTCTGCAAACGACT

GCAGGTACGCCTGCAGGAATCGCCCCATCATCGTCACAAAGGTCTTGTTGCTGGTGAAGGTCAG

CTGCAACCCGCGGTGCTCCTCGTTCAGCCAGGTCTTGCATACGGCCGCCAGAGCTTCCACTTGG

TCAGGCAGTAGTTTGAAGTTCGCCTTTAGATCGTTATCCACGTGGTACTTGTCCATCAGCGCGC

GCGCAGCCTCCATGCCCTTCTCCCACGCAGACACGATCGGCACACTCAGCGGGTTCATCACCGT

AATTTCACTTTCCGCTTCGCTGGGCTCTTCCTCTTCCTCTTGCGTCCGCATACCACGCGCCACT

GGGTCGTCTTCATTCAGCCGCCGCACTGTGCGCTTACCTCCTTTGCCATGCTTGATTAGCACCG

GTGGGTTGCTGAAACCCACCATTTGTAGCGCCACATCTTCTCTTTCTTCCTCGCTGTCCACGAT

TACCTCTGGTGATGGCGGGCGCTCGGGCTTGGGAGAAGGGCGCTTCTTTTTCTTCTTGGGCGCA

ATGGCCAAATCCGCCGCCGAGGTCGATGGCCGCGGGCTGGGTGTGCGCGGCACCAGCGCGTCTT

GTGATGAGTCTTCCTCGTCCTCGGACTCGATACGCCGCCTCATCCGCTTTTTTGGGGGCGCCCG

GGGAGGCGGCGGCGACGGGACGGGGACGACACGTCCTCCATGGTTGGGGGACGTCGCGCCGCA

CCGCGTCCGCGCTCGGGGGTGGTTTCGCGCTGCTCCTCTTCCCGACTGGCCATTTCCTTCTCCT

ATAGGCAGAAAAAGATCATGGAGTCAGTCGAGAAGAAGGACAGCCTAACCGCCCCCTCTGAGTT

CGCCACCACCGCCTCCACCGATGCCGCCAACGCGCCTACCACCTTCCCCGTCGAGGCACCCCCG

-continued

```
CTTGAGGAGGAGGAAGTGATTATCGAGCAGGACCCAGGTTTTGTAAGCGAAGACGACGAGGACC

GCTCAGTACCAACAGAGGATAAAAAGCAAGACCAGGACAACGCAGAGGCAAACGAGGAACAAGT

CGGGCGGGGGGACGAAAGGCATGGCGACTACCTAGATGTGGGAGACGACGTGCTGTTGAAGCAT

CTGCAGCGCCAGTGCGCCATTATCTGCGACGCGTTGCAAGAGCGCAGCGATGTGCCCCTCGCCA

TAGCGGATGTCAGCCTTGCCTACGAACGCCACCTATTCTCACCGCGCGTACCCCCAAACGCCA

AGAAAACGGCACATGCGAGCCCAACCCGCGCCTCAACTTCTACCCCGTATTTGCCGTGCCAGAG

GTGCTTGCCACCTATCACATCTTTTTCCAAAACTGCAAGATACCCCTATCCTGCCGTGCCAACC

GCAGCCGAGCGGACAAGCAGCTGGCCTTGCGGCAGGGCGCTGTCATACCTGATATCGCCTCGCT

CAACGAAGTGCCAAAAATCTTTGAGGGTCTTGGACGCGACGAGAAGCGCGCGGCAAACGCTCTG

CAACAGGAAAACAGCGAAAATGAAAGTCACTCTGGAGTGTTGGTGGAACTCGAGGGTGACAACG

CGCGCCTAGCCGTACTAAAACGCAGCATCGAGGTCACCCACTTTGCCTACCCGGCACTTAACCT

ACCCCCCAAGGTCATGAGCACAGTCATGAGTGAGCTGATCGTGCGCCGTGCGCAGCCCCTGGAG

AGGGATGCAAATTTGCAAGAACAAACAGAGGAGGGCCTACCCGCAGTTGGCGACGAGCAGCTAG

CGCGCTGGCTTCAAACGCGCGAGCCTGCCGACTTGGAGGAGCGACGCAAACTAATGATGGCCGC

AGTGCTCGTTACCGTGGAGCTTGAGTGCATGCAGCGGTTCTTTGCTGACCCGGAGATGCAGCGC

AAGCTAGAGGAAACATTGCACTACACCTTTCGACAGGGCTACGTACGCCAGGCCTGCAAGATCT

CCAACGTGGAGCTCTGCAACCTGGTCTCCTACCTTGGAATTTTGCACGAAAACCGCCTTGGGCA

AAACGTGCTTCATTCCACGCTCAAGGGCGAGGCGCGCCGCGACTACGTCCGCGACTGCGTTTAC

TTATTTCTATGCTACACCTGGCAGACGGCCATGGGCGTTTGGCAGCAGTGCTTGGAGGAGTGCA

ACCTCAAGGAGCTGCAGAAACTGCTAAAGCAAAACTTGAAGGACCTATGGACGGCCTTCAACGA

GCGCTCCGTGGCCGCGCACCTGGCGGACATCATTTTCCCCGAACGCCTGCTTAAAACCCTGCAA

CAGGGTCTGCCAGACTTCACCAGTCAAAGCATGTTGCAGAACTTTAGGAACTTTATCCTAGAGC

GCTCAGGAATCTTGCCCGCCACCTGCTGTGCACTTCCTAGCGACTTTGTGCCCATTAAGTACCG

CGAATGCCCTCCGCCGCTTTGGGGCCACTGCTACCTTCTGCAGCTAGCCAACTACCTTGCCTAC

CACTCTGACATAATGGAAGACGTGAGCGGTGACGGTCTACTGGAGTGTCACTGTCGCTGCAACC

TATGCACCCCGCACCGCTCCCTGGTTTGCAATTCGCAGCTGCTTAACGAAAGTCAAATTATCGG

TACCTTTGAGCTGCAGGGTCCCTCGCCTGACGAAAAGTCCGCGGCTCCGGGGTTGAAACTCACT

CCGGGGCTGTGGACGTCGGCTTACCTTCGCAAATTTGTACCTGAGGACTACCACGCCCACGAGA

TTAGGTTCTACGAAGACCAATCCCGCCCGCCTAATGCGGAGCTTACCGCCTGCGTCATTACCCA

GGGCCACATTCTTGGCCAATTGCAAGCCATCAACAAAGCCCGCCAAGAGTTTCTGCTACGAAAG

GGACGGGGGTTTACTTGGACCCCCAGTCCGGCGAGGAGCTCAACCCAATCCCCCCGCCGCCGC

AGCCCTATCAGCAGCAGCCGCGGGCCCTTGCTTCCCAGGATGGCACCCAAAAAGAAGCTGCAGC

TGCCGCCGCCACCCACGGACGAGGAGGAATACTGGGACAGTCAGGCAGAGGAGGTTTTGGACGA

GGAGGAGGAGGACATGATGGAAGACTGGGAGAGCCTAGACGAGGAAGCTTCCGAGGTCGAAGAG

GTGTCAGACGAAACACCGTCACCCTCGGTCGCATTCCCCTCGCCGGCGCCCCAGAAATCGGCAA

CCGGTTCCAGCATGGCTACAACCTCCGCTCCTCAGGCGCCGCCGGCACTGCCCGTTCGCCGACC

CAACCGTAGATGGGACACCACTGGAACCAGGGCCGGTAAGTCCAAGCAGCCGCCGCCGTTAGCC

CAAGAGCAACAACAGCGCCAAGGCTACCGCTCATGGCGCGGGCACAAGAACGCCATAGTTGCTT

GCTTGCAAGACTGTGGGGGCAACATCTCCTTCGCCCGCCGCTTTCTTCTCTACCATCACGGCGT

GGCCTTCCCCCGTAACATCCTGCATTACTACCGTCATCTCTACAGCCCATACTGCACCGGCGGC
```

-continued

```
AGCGGCAGCAACAGCAGCGGCCACACAGAAGCAAAGGCGACCGGATAGCAAGACTCTGACAAAG

CCCAAGAAATCCACAGCGGCGGCAGCAGCAGGAGGAGGAGCGCTGCGTCTGGCGCCCAACGAAC

CCGTATCGACCCGCGAGCTTAGAAACAGGATTTTTCCCACTCTGTATGCTATATTTCAACAGAG

CAGGGGCCAAGAACAAGAGCTGAAAATAAAAAACAGGTCTCTGCGATCCCTCACCCGCAGCTGC

CTGTATCACAAAAGCGAAGATCAGCTTCGGCGCACGCTGGAAGACGCGGAGGCTCTCTTCAGTA

AATACTGCGCGCTGACTCTTAAGGACTAGTTTCGCGCCCTTTCTCAAATTTAAGCGCGAAAACT

ACGTCATCTCCAGCGGCCACACCCGGCGCCAGCACCTGTTGTCAGCGCCATTATGAGCAAGGAA

ATTCCCACGCCCTACATGTGGAGTTACCAGCCACAAATGGGACTTGCGGCTGGAGCTGCCCAAG

ACTACTCAACCCGAATAAACTACATGAGCGCGGGACCCCACATGATATCCCGGGTCAACGGAAT

ACGCGCCCACCGAAACCGAATTCCCTTGGAACAGGCGGCTATTACCACCACACCTCGTAATAAC

CTTAATCCCCGTAGTTGGCCCGCTGCCCTGGTGTACCAGGAAAGTCCCGCTCCCACCACTGTGG

TACTTCCCAGAGACGCCCAGGCCGAAGTTCAGATGACTAACTCAGGGGCGCAGCTTGCGGGCGG

CTTTCGTCACAGGGTGCGGTCGCCCGGGC
```

CymR *Pseudomonas putida*  
SEQ ID NO: 17
```
atgagtccaaagagaagaacacaggcagagcgcgcaatggagacccagggcaagttgattgcag cggccctgggggttttacgggaaaaaggttacgcgggattccggatcgcagatgtgcccggtgc tgcaggtgtctcgagaggagcgcagagccatcatttcccgacaaagcttgagcttctgcttgcc actttt gaatggctttacgaacagatcaccgaacgcagtcgggctcgattagcgaaattgaagc cagaggatgacgtcatccagcaaatgctggacgacgccgccgaattttt cctcgacgatgactt ctctatcagccttgatttgattgtggctgccgaccgggatccagcgttacgcgagggtattcag cgcacggtagagaggaatcggtttgtcgtcgaggatatgtggcttggtgttctggtgagccgtg gtctttcgcgtgatgatgcagaagatatcctttggttgatattcaattcggtgcgtgggcttgc tgttcgtagcctatggcagaaggacaaagaacgctttgagcgtgtcaggaactcgacactcgaa attgcgcgagagcggtacgcgaaattcaagcgctag
```

CymR Protein *Pseudomonas putida*  
SEQ ID NO: 18
```
MSPKRRTQAERAMETQGKLIAAALGVLREKGYAGFRIADVPGAAGVSRGAQSHHFPTKLE

LLLATFEWLYEQITERSRARLAKLKPEDDVIQQMLDDAAEFFLDDDFSISLDLIVAADRD

PALREGIQRTVERNRFVVEDMWLGVLVSRGLSRDDAEDILWLIFNSVRGLAVRSLWQKDK

ERFERVRNSTLEIARERYAKFKR
``` rcCymR  
(In the following sequence, the mutations compared to CymR are highlighted.)  
SEQ ID NO: 19
```
atgagtccaaagagaagaacacaggcagagcgcgcaatggagacccagggcaagttgattgcag cggccctgggggttttacgggaaaaaggttacgcgggattccggatcgcagatgtgcccggtgc tgcaggtgtctcgagaggagcgcagagccatcatttcccgacaaagcttgagcttctgcttgcc actttt gaatggctttacgaacagatcaccgaacgcagtcgggctcgattagcgaaattgaagc cagaggatgacgtcatccagcaaatgctggacgacgccgccgaattttt cctcgacgatgactt ctctatcagccttgatttgattgtggctgccgaccgggatccaGTCttacgcgagggtattcag cgcacggtagagaggaatcggtttgtcgtcGGCgatATCtggcttggtgttctggtgagccgtg gtctttcgcgtgatgatgcagaagatatcctttggttgatattcaattcggtgcgtgggcttgc tgttcgtagcctatggcagaaggacaaagaacgctttgagcgtgtcaggaactcgacactcgaa attgcgcgagagcggtacgcgaaattcaagcgctag
```

-continued rcCymR protein
SEQ ID NO: 20

MSPKRRTQAERAMETQGKLIAAALGVLREKGYAGFRIADVPGAAGVSRGAQSHHFPTKLE

LLLATFEWLYEQITERSRARLAKLKPEDDVIQQMLDDAAEFFLDDDFSISLDLIVAADRD

PVLREGIQRTVERNRFVVGDIWLGVLVSRGLSRDDAEDILWLIFNSVRGLAVRSLWQKDK

ERFERVRNSTLEIARERYAKFKR

FIG. 3A sequence
SEQ ID NO: 21

GGCGTGTACGGTGGGAGGTCTATATAAGCAGAGCTGaacaaacagacaatctggtctgtttgta

GTTTAGTGAACCGAGATCTTTGTCGATCCT

FIG. 3B sequence
SEQ ID NO: 22

GGCGTGTACGGTGGGAGGTCTATATAAGCAGAGCTGaacaaacagacaatctggtctgtttgta

GTTTAGTGAACCGAGATCTTTGTCGATCCTACCATCCACTCGACACACCCGCCAGCGGCCGCaa caaacagacaatctggtctgtttgtaAGCTICCGAGCTCTCGAATTCAAAGGAGGTACCCACCA

TG

---

The invention claimed is:

1. A nucleic acid molecule comprising:
   (i) a minimal promoter comprising 1, 2, 3, 4, 5 or 6 cumate operator (CuO) sites,
   (ii) a cap gene, and
   (iii) a rep gene,
in the above 5'-3' order, wherein the cap gene and the rep gene are both operably-associated with the promoter.

2. The nucleic acid molecule as claimed in claim 1, wherein the promoter is a minimal pol II promoter.

3. The nucleic acid molecule as claimed in claim 1, wherein the promoter comprises 4, 5 or 6 CuO sites.

4. The nucleic acid molecule as claimed in claim 1, wherein the CuO site(s) in the promoter are placed upstream of both the TATA box and the +1 site.

5. The nucleic acid molecule as claimed in claim 1, wherein the rep gene encodes Rep78 and Rep68, but not Rep 52 or Rep 40.

6. The nucleic acid molecule as claimed in claim 1, wherein the rep gene is operably-associated with an Internal Ribosome Entry Site (IRES) which is placed between the cap and rep genes.

7. The nucleic acid molecule as claimed in claim 1, wherein the rep gene encodes Rep78 and Rep68.

8. The nucleic acid molecule as claimed in claim 1, wherein the promoter comprises 6 CuO sites.

9. A vector or plasmid comprising the nucleic acid molecule of claim 1.

10. A kit comprising:
   (A) a nucleic acid molecule as claimed in claim 1;
and optionally one or more of the following:
   (B) a nucleic acid molecule, vector or plasmid comprising:
      (i) a promoter or a minimal promoter comprising one or more cumate operator sites, operably-associated with
      (ii) a gene encoding a rc-CymR-TAD polypeptide;
   (C) a nucleic acid molecule, vector or plasmid comprising
      (i) a promoter or a constitutive promoter, operably-associated with
      (ii) a gene encoding CymR;
   (D) a nucleic acid molecule, vector or plasmid comprising:
      (i) a promoter or a constitutive promoter, operably-associated with
      (ii) a gene encoding a CymR-TAD polypeptide;
   (E) a nucleic acid molecule, vector or plasmid comprising:
      (i) one or more promoters, which may or may not comprise one or more cumate operator sites, operably-associated with
      (ii) one or more adenoviral genes which are competent to support AAV production;
   (F) a nucleic acid molecule, vector or plasmid comprising:
      (i) a promoter, operably-associated with
      (ii) a transgene,
   wherein the promoter and transgene are flanked by ITRs.

11. A cell line, comprising:
   (A) a nucleic acid molecule as claimed in claim 1;
and optionally one or more of the following:
   (B) a nucleic acid molecule, vector or plasmid comprising:
      (i) a promoter or a minimal promoter comprising one or more cumate operator sites, operably-associated with
      (ii) a gene encoding a rc-CymR-TAD polypeptide;
   (C) a nucleic acid molecule, vector or plasmid comprising:
      (i) a promoter or a constitutive promoter, operably-associated with
      (ii) a gene encoding CymR;
   (D) a nucleic acid molecule, vector or plasmid comprising:
      (i) a promoter or a constitutive promoter, operably-associated with
      (ii) a gene encoding a CymR-TAD polypeptide;
   (E) a nucleic acid molecule, vector or plasmid comprising:
      (i) one or more promoters, which may or may not comprise one or more cumate operator sites, operably-associated with
      (ii) one or more adenoviral genes which are competent to support AAV production;
   (F) a nucleic acid molecule, vector or plasmid comprising:
      (i) a promoter, operably-associated with
      (ii) a transgene,
   wherein the promoter and transgene are flanked by ITRs.

12. The cell line as claimed in claim 11, wherein the cell line is a packaging cell line or a producer cell line.

13. The cell line as claimed in claim 11, wherein the each of (A), (B), (C), (E), and (F), when present, are integrated into the genome of the cell line, and wherein the specified genes are expressed or expressible therefrom.

14. The cell line as claimed in claim 11, wherein the cells of the cell line are HEK293, HEK293T, HEK293A, PerC6 or 911 cells.

15. A process for producing an AAV cell line, the process comprising the steps of integrating into the genome of the cells of the cell line:
   (A) a nucleic acid molecule as claimed in claim 1, thereby producing a cell line that inducibly expresses viral cap and rep genes;
and optionally one or more of the following:
(B) a nucleic acid molecule, vector or plasmid comprising:
(i) a promoter or a minimal promoter comprising one or more cumate operator sites, operably-associated with
(ii) a gene encoding a rc-CymR-TAD polypeptide;
(C) a nucleic acid molecule, vector or plasmid comprising:
(i) a promoter or a constitutive promoter, operably-associated with
(ii) a gene encoding a CymR;
(D) a nucleic acid molecule, vector or plasmid comprising:
(i) one or more promoters, which may or may not comprise one or more cumate operator sites, operably-associated with
(ii) one or more adenoviral genes which are competent to support AAV production.

16. A method of inducing transcription of cap and rep genes in a cell, the method comprising:
inducing the transcription of cap and rep genes in a cell which comprises in its genome:
(A) a nucleic acid molecule as claimed in claim 1,
wherein the inducing is by the presence, in the cell, of a CymR-TAD polypeptide or by the expression or transient expression, in the cell, of a nucleic acid molecule which encodes a CymR-TAD polypeptide.

17. The method as claimed in claim 16, wherein the method additionally comprises the step of introducing into the cell:
(B) a nucleic acid molecule, vector or plasmid comprising:
(i) a promoter or a constitutive promoter, operably-associated with
(ii) a nucleotide sequence encoding a CymR-TAD;
and/or
(C) a nucleic acid molecule, vector or plasmid comprising:
(i) one or more promoters, which may or may not comprise one or more cumate operator sites, operably-associated with
(ii) one or more adenoviral genes which are competent to support AAV production;
and/or
(D) a nucleic acid molecule, vector or plasmid comprising:
(i) a promoter, operably-associated with
(ii) a transgene,
wherein the promoter and transgene are flanked by ITRs.

18. A method of inducing transcription of cap and rep genes in a cell, the method comprising:
inducing the transcription of cap and rep genes in a cell which comprises:
(A) a nucleic acid molecule as claimed in claim 1;
(B) a nucleic acid molecule, vector or plasmid comprising:
(i) a promoter comprising one or more cumate operator sites, operably-associated with
(ii) a gene encoding a rc-CymR-TAD polypeptide; and
(C) a nucleic acid molecule, vector or plasmid comprising:
(i) a promoter, operably-associated with
(ii) a gene encoding a CymR;
and optionally
(D) a nucleic acid molecule, vector or plasmid comprising:
(i) one or more promoters, which may or may not comprise one or more cumate operator sites, operably-associated with
(ii) one or more adenoviral genes which are competent to support AAV production;
and/or
(E) a nucleic acid molecule, vector or plasmid comprising:
(i) a promoter, operably-associated with
(ii) a transgene, wherein the promoter and transgene are flanked by ITRs,
wherein the inducing is by the presence of or introduction into the cell of cumate.

19. The method of inducing transcription of cap and rep genes in a cell as claimed in claim 18, wherein (A), (B), (C), (D) and (E), when present, are all integrated into the genome of the cell.

* * * * *